US010172567B2

(12) United States Patent
Moxon et al.

(10) Patent No.: US 10,172,567 B2
(45) Date of Patent: Jan. 8, 2019

(54) SYSTEM AND METHOD OF DETECTING AND PREDICTING SEIZURES

(75) Inventors: Karen A. Moxon, Collingswood, NJ (US); Dane Grasse, Richardson, TX (US)

(73) Assignee: Drexel University, Philadelphia, PA (US)

(*) Notice: Subject to any disclaimer, the term of this patent is extended or adjusted under 35 U.S.C. 154(b) by 417 days.

(21) Appl. No.: 14/122,906

(22) PCT Filed: Jun. 1, 2012

(86) PCT No.: PCT/US2012/040540
§ 371 (c)(1),
(2), (4) Date: Mar. 7, 2014

(87) PCT Pub. No.: WO2012/167140
PCT Pub. Date: Dec. 6, 2012

(65) Prior Publication Data
US 2014/0257128 A1    Sep. 11, 2014

Related U.S. Application Data

(60) Provisional application No. 61/492,173, filed on Jun. 1, 2011, provisional application No. 61/568,404, filed on Dec. 8, 2011.

(51) Int. Cl.
*A61B 5/04* (2006.01)
*A61B 5/00* (2006.01)
(Continued)

(52) U.S. Cl.
CPC ........ *A61B 5/7275* (2013.01); *A61B 5/04001* (2013.01); *A61B 5/0476* (2013.01);
(Continued)

(58) Field of Classification Search
None
See application file for complete search history.

(56) References Cited

U.S. PATENT DOCUMENTS

2008/0077039 A1* 3/2008 Donnett .............. A61B 5/0006
600/544
2010/0204748 A1* 8/2010 Lozano .............. A61B 5/04001
607/45
(Continued)

FOREIGN PATENT DOCUMENTS

WO    WO 2009/135092 A2    11/2009

OTHER PUBLICATIONS

Grasse et al. Correcting the Bias of Spike Field Coherence Estimators Due to a Finite Number of Spikes. J Neurophysiol 104: 548-558, 2010.*

(Continued)

*Primary Examiner* — Etsub Berhanu
(74) *Attorney, Agent, or Firm* — Saul Ewing Arnstein & Lehr LLP; Kathryn Doyle; Brian Landry

(57) ABSTRACT

The present invention describes systems and methods for predicting and detecting a seizure in a subject. The methods of the invention comprise measuring interneuron synchrony in terms of the coherence between interneuron action potentials and local field potential oscillations. In one embodiment, the detection of specific patterns of coherence, correlation and firing rate of interneurons predicts an upcoming seizures.

10 Claims, 26 Drawing Sheets

(51) Int. Cl.
 A61B 5/0476 (2006.01)
 A61N 1/36 (2006.01)
(52) U.S. Cl.
 CPC .......... *A61B 5/4094* (2013.01); *A61B 5/6868* (2013.01); *A61B 5/7282* (2013.01); *A61N 1/3606* (2013.01); *A61N 1/36064* (2013.01)

(56) References Cited

U.S. PATENT DOCUMENTS

| 2010/0292602 | A1* | 11/2010 | Worrell | A61B 5/0478 600/544 |
|---|---|---|---|---|
| 2011/0130797 | A1* | 6/2011 | Talathi | A61B 5/0476 607/3 |
| 2011/0224752 | A1* | 9/2011 | Rolston | A61B 5/04001 607/45 |
| 2012/0089004 | A1* | 4/2012 | Hsu | A61B 5/726 600/407 |

OTHER PUBLICATIONS

Lindsey, B. G., et al., 1989, "Gravitational representation of simultaneously recorded brainstem respiratory neuron spike trains" Brain Research, 483, 373-378.
Martinerie, J., et al., 1998, "Epileptic seizures can be anticipated by non-linear analysis", Nature Med, 4, 1173-1176.
Mathern, G. W., et al., 1993, Hippocampal EEG excitability and chronic spontaneous seizures are associated with aberrant synaptic reorganization in the rat intrahippocampal kainate model, Electroencephalogy, 87, 326-339.
Matsumoto, H., et al., 1964, "Cortical Cellular Phenomena in Experimental Epilepsy: Ictal Manifestations", Exp. Neurol., 9, 305-326.
McCloskey, D. P., et al., "Progressive, potassium-sensitive epileptiform activity in hippocampal area CA3 of pilocarpine-treated rats with recurrent seizures", 2011, Epilepsy, 97, 92-102.
Mendell, L. M., et al., 1971, "Terminals of Single Ia Fibers: Location, Density, and Distribution Within a Pool of 300 Homonymous Motoneurons", Neurophysiol., 34, 171-187.
Montgomery, S. M., et al., "Behavior-Dependent Coordination of Multiple Theta Dipoles in the Hippocampus", 2009, J. Neurosci., 29(5), 1381-1394.
Mormann, F., et al., 2007, "Seizure prediction: the long and winding road", Brain, 130, 314-333.
Morrell, M. J., 2011, "Responsive cortical stimulation for the treatment of medically intractable partial epilepsy", Neurology, 77, 1295-1304.
Moxon, K. A., et al., 1999, "Multiple single units and population responses during inhibitory gating of hippocampal auditory response in freely-moving rats", Brain Research, 825, 75-85.
Murthy, V. N., et al., 1999, "Oscillatory Activity in Sensorimotor Cortex of Awake Monkeys: Synchronization of Local Field Potentials and Relation to Behavior", J. Neurophysiology, 76, 3949-3967.
Nicolelis, M. A. L., et al., 2003, "Chronic, multisite, multielectrode recordings in macaque monkeys", PNAS, 100, 11041-11046.
O'Keefe, J., et al., 1993, "Phase Relationship Between Hippocampal Place Units and the EEG Theta Rhythm", Hippocampus, 3, 317-330.
Fries, P., et al., 1997, "Synchronization of oscillatory responses in visual cortex correlates with perception in interocular rivalry", PNAS, 94, 12699-12704.
Kopell, N., et al., 2000, "Gamma rhythms and beta rhythms have different synchronization properties", PNAS, 97, 1867-1872.
Queiroz, C. M., et al., 2009, "Dynamics of Evoked Local Field Potentials in the Hippocampus of Epileptic Rats With Spontaneous Seizures", Neurophysiol., 101, 1588-1597.
Le Van Quyen, M., 2000, "Spatio-temporal characterizations of non-linear changes in intracranial activities prior to human temporal lobe seizures", European Journal of Neuroscience, 12, 2124-2134.

Rancine, R. J., 1972, "Modification of Seizure Activity by Electrical Stimulation: II. Motor Seizure", Electroencephalogr. 32, 281-2.
Ribeiro, S., et al., 2004, "Reverberation, storage, and postsynaptic propagation of memories during sleep", Learning & Memory, 11, 686-696.
Rogowski, Z., et al., 1981, "On the Prediction of Epileptic Seizures", Biol. Cybern. 42, 9-15.
Scaglione, A., et al., 2011, "Trial-to-trial variability in the responses of neurons carries information about stimulus location in the rat whisker thalamus", PNAS, 108, 14956-61.
Mendell, L. M., et al., 1968, Terminals of Single Ia Fibers: Distribution within a Pool of 300 Homonymous Motor Neurons, Science, 160, 96-98.
Shin, D. S., et al., 2010, "Characterizing the persistent CA3 interneuronal spiking activity in elevated extracellular potassium in the young rat hippocampus", Brain Res., 1331, 39-50.
Bragin, A., et al., 1999, "Hippocampal and Entorhinal Cortex High-Frequency Oscillations (100-500 Hz) in Human Epileptic Brain and in Kainic Acid-Treated Rats with Chronic Seizures", Epilepsia, 40(2), 127-137.
Spencer, S. S., et al., 1992, Morphological Patterns of Seizures Recorded Intracranially, Epilepsia, 3393), 537-545.
Bragin, A., et al., 2002, "Interictal High-Frequency Oscillations (80-500Hz) in the Human Epileptic Brain: Entorhinal Cortex", Annals of Neurology, 52, 407-415.
Stewart, M., et al., 1990, "Do septal neurons pace the hippocampal theta rhythm?" Trends Neurosci, 13, 163-168.
Timofeev, I., et al., 2002, "The Role of Chloride-dependent Inhibition and the Activity of Fast-Spiking Neurons During Cortical Spike-wave Electrographic Seizures", Neuroscience, 114, 1115-1132.
Traub, R. D., et al., 1996, "Analysis of gamma rhythms in the rat hippocampus in vitro" J. Physiol., 493.2, 471-484.
Traub, R. D., et al., 2001, "Gap Junctions between Interneuron Dendrites Can Enhance Synchrony of Gamma Oscillations in Distributed Networks", J. Neurosci., 21(23), 9478-9486.
Traub, R. D., et al., 2001, "A Possible Role for Gap Junctions in Generation of Very Fast EEG Oscillations Preceding the Onset of, and Perhaps Initiating, Seizures", Epilepsia, 42(2), 153-170.
Truccolo, W., et al., 2011, "Single-neuron dynamics in human focal epilepsy", Nat. Neurosci., 14, 635-641.
Valezquez, J. L. P., et al., 1999, "Synchronization of GABAergic interneuronal networks during seizure-like activity in the rat horizontal hippocampal slice", Eur. Neurosci., 11, 4110-4118.
Vinck, M., et al., 2010, "Gamma-Phase Shifting in Awake Monkey Visual Cortex", J. Neurosci., 30(4), 1250-1257.
Vinck, M., et al., 2010, "The pairwise phase consistency: A bias-free measure of rhythmic neuronal synchronization", NeuroImage, 51, 112-122.
Wendling, F., et al., 2002, "Epileptic fast activity can be explained by a model of impaired BABAergic dendritic inhibition", Euro. J. Neurosci., 15, 1499-1508.
Wittner, L., et al., 2007, "Factors defining a pacemaker region for synchrony in the hippocampus", J. Physiol., 584.3, 867-883.
Wong, S., et al., 2007, "A Stochastic Framework for Evaluating Seizure Prediction Algorithms Using Hidden Markov Models", Neurophysiol., 97, 2525-2532.
Ylinen, A., et al., 1995, "Intracellular Correlates of Hippocampal Theta Rhythm in Identified Pyramidal Cells, Granule Cells, and Basket Cells", Hippocampus, 5, 78-90.
Ziburkus, J., et al., 2006, "Interneuron and Pyramidal Cell Interplay During In Vitro Seizure-Like Events", Neurophysiol., 95, 3948-3954.
Allen, P.J., et al., "Very high-frequency rhythmic activity during SEEG suppression in frontal lobe epilepsy", 1992, Electroencephalogr. 82, 155-159.
Ayala, G. F., et al., "Excitability Changes and Inhibitory Mechanisms in Neocortical Neurons During Seizures", 1970, Neurophysiol. 33, 73-85.
Babb, T. L., et al., 1987, "Firing patterns of human limbic neurons during stereoencephalography (SEEG) and clinical temporal lobe seizures", Electroencephalogr. 66, 467-482.

(56) References Cited

OTHER PUBLICATIONS

Babb, T. L., et al., 1976, "Epileptogenesis of Human Limbic Neurons in Psychomotor Epileptics", Electroencephalogr. 40, 225-243.
Bartolomei, F., et al., 2005, "Entorhinal Cortex Involvement in Human Mesial Temporal Lobe—Epilepsy: An Electrophysiologic and Volumetric Study", Epilepsia, 46(5), 677-687.
Bower, M. R., et al., 2008, "Changes in Granule Cell Firing Rates Precede Locally Recorded Spontaneous Seizures by Minutes in an Animal Model of Temporal Lobe Epilepsy", Neurophysio. 99, 2431-2442.
Bragin, A., et al., 1997, "Epileptic Afterdischarge in the Hippocampal-entorhinal System: Current Source Density and Unit Studies", Neuroscience, 76, 1187-1203.
Bragin, A., et al., 1999, "High-Frequency Oscillations in Human Brain", Hippocampus, 9, 137-142.
Bragin, A., et al., 1999, "Electrophysiologic Analysis of a Chronic Seizure Model After Unilateral Hippocampal KA Injection", Epilepsia, 40(9), 1210-1221.
Bragin, A., et al., 2000, "Chronic Epileptogenesis Requires Development of a Network of Pathlogically Interconnected Neuron Clusters: A Hypothesis", Epilepsia, 41(Suppl. 6), S144-S152.
Bragin, A., et al., 2005, "Analysis of Chronic Seizure Onsets after Intrahippocampal Kainic Acid Injection in Freely Moving Rats", Epilepsia, 46(10), 1592-1598.
Bragin, A., et al., 2007, "Analysis of Initial Slow Waves (ISWs) at the Seizure Onset in Patients with Drug Resistant Temporal Lobe Epilepsy", Epilepsia, 48(10), 1883-1894.
Butuzova, M. V., et al., 2008, "Repeated blockade of GABAa receptors in the medial septal region induces epileptiform activity in the hippocampus", Neurosci. 434, 133-138.
Cappaert, N. L. M., et al., 2009, "Spatio-Temporal Dynamics of Theta Oscillations in Hippocampal-Entorhinal Slices", Hippocampus 19, 1065-1077.
Chapin, J. K., et al., 1999, "Real-time control of a robot arm using simultaneously recorded neurons in the motor cortex", Nature Neuroscience 2, 664-670.
Colom, L. V., et al., 2006, "Septo-Hippocampal Networks in Chronically Epileptic Rats: Potential Antiepileptic Effects of Theta Rhythm Generation", Neurophysiol. 95, 3645-3653.
Courtemanche, R., et al., 2002, "Local Field Potential Oscillations in Primate Cerebellar Cortex: Modulation During Active and Passive Expectancy", Neurophysiol., 88, 771-782.
Csicsvari, J. et al., 1998, "Reliability and State Dependence of Pyramidal Cell-Interneuron Synapses in the Hippocampus: an Ensemble Approach in the Behaving Rat", Neuro., 21, 179-189.
Csicsvari, J., et al., "Ensemble Patterns of Hippocampal CA3-CA1 Neurons during Sharp Wave-Associated Population Events", 2000, Neuron., 28, 585-594.
Derchansky, M., et al., 2006, "Bidirectional multisite seizure propagation in the intact isolated hippocampus: The multifocality of the seizure "focus"", Neurobiol. 23, 312-328.
Dichter, M., et al., 1969, "Penicillin-Induced Interictal Discharges from the Cat Hippocampus. II. Mechanisms Underlying Origin and Restriction", Neurophysiol. 3, 663-687.
Donoghue, J. P., et al., 1998, "Neural Discharge and Local Field Potential Oscillations in Primate Motor Cortex During Voluntary Movements", Neurophysiol., 32, 159-173.
Dzhala, V. I., et al., 2003, "Transition from Interictal to Ictal Activity in Limbic Networks In Vitro", J. Neurosci., 23(21), 7873-7880.
Eggermont, J. J., 1992, "Neural Interaction in Cat Primary Auditory Cortex. Dependence on Recording Depth, Electrode Separation, and Age", Neurophysiol., 68, 1216-1228.
Eggermont, J. J., et al., 1995, "Synchrony Between Single-Unit Activity and Local Field Potentials in Relation to Periodicity Coding in Primary Auditory Cortex", Neurophysiol., 73, 227-245.
Eid, T., et al., 2004, "Loss of glutamine synthetase in the human epileptogenic hippocampus: possible mechanism for raised extracellular glutamate in mesial temporal lobe epilepsy", Lancet, 363, 28-37.
Emondi, A. A., et al., 2004, "Tracking neurons recorded from tetrodes across time", Neurosci Methods, 135, 95-105.
Engel, Jr., J., 1990, "The Hans Berger lecture—Functional explorations of the human epileptic brain and their therapeutic implications", Electroencephalogr. 76, 296-316.
Fisher, R. S., et al., 2000, "The impact of epilepsy from the patient's perspective I. Descriptions and subjective perceptions", Epilepsy, 41, 39-51.
Foffani, G., et al., 2007, "Reduced Spike-Timing Reliability Correlates with the Emergence of Fast Ripples in the Rat Epileptic Hippocampus", Neuron, 55, 930-941.
Foffani, G., et al., 2004, "Role of Spike Timing in the Forelimb Somatosensory Cortex of the Rat", J. Neurosci., 24(33), 7266-7271.
Fries, P., et al., 2001, "Modulation of Oscillatory Neuronal Synchronization by Selective Visual Attention", Science, 291, 1560-1563.
Fries, P., et al., 2008, "The Effects of Visual Stimulation and Selective Visual Attention on Rhythmic Neuronal Synchronization in Macaque Area V4", J. Neurosci, 28(18), 4823-4835.
Fujiwara-Tsukamoto, Y., et al., 2010, "Prototypic Seizure Activity Driven by Mature Hippocampal Fast-Spiking Interneurons", J. Neurosci, 30(41), 13679-13689.
Gnatkovsky, V., et al., 2008, Fast Activity at Seizure Onset Is Medicated by Inhibitory Circuits in the Entorhinal Cortex In Vitro, Annals of Neurology, 64, 674-686.
Goldberg, J. A., et al., 2004, "Spike Synchronization in the Cortex-Basal Ganglia Networks of Parkinsonian Primates Reflects Global Dynamics of the Local Field Potentials", J. Neurosci., 24(25), 6003-6010.
Gotman, J., et al., 1989, "Interictal spiking increases after seizures but does not after decrease in medication", Clin. Neurophys., 72, 7-15.
Grasse, D. W., et al., 2010, "Correcting the Bias of Spike Field Coherence Estimators Due to a Finite Number of Spikes", Neurophysiolgoy, 104, 548-558.
Gray, C. M., et al., 1995, "Tetrodes markedly improve the reliability and yield of multiple single-unit isolation from multi-unit recordings in cat striate cortex", Neuroscience, 63, 43-54.
Gray, C. M., et al., 1989, "Stimulus-specific neuronal oscillations in orientation columns of cat visual cortex", Proc. Natl. Acad. Sci., 86, 1698-1702.
Harris, K. D., 2002, "Spike train dynamics predicts theta-related phase precession in hippocampal pyramidal cells", Nature, 417, 738-741.
Huerta, P. T., et al., 1993, "Heightened synaptic plasticity of hippocampal CA1 neurons during a cholinergically induced rhythmic state", Nature, 364, 723-725.
Iasemidis, L, D., et al., 1990, "Phase Space Topography and the Lyapunov Exponent of Electrocorticograms in Partial Seizures", Brain Topography, 2, 187-201.
Kispersky, T., et al., 2010, "The Mechanism of Abrupt Transition between Theta and Hyper-Excitable Spiking Activity in Medial Entorhinal Cortex Layer II Stellate Cells", PloS One, 2, 1-21.
Kitchigina, V. F., et al., 2009, "Theta activity of septal neurons during different epileptic phases: The same frequency but different signifiance?", Exp. Neurol., 216, 449-458.
Kossoff, E. H., et al., 2004, "Effect of an External Responsive Neurostimulator on Seizures and Electrographic Discharges during Subdural Electrode Monitoring", Epilepsia, 45(12), 1560-1567.
Larson, J., et al., 1986, "Patterned stimulation at the theta frequency is optimal for the induction of hippocampal long-term potentiation", Brain Research, 368, 347-350.
Le Van Quyen, M., et al., 2008, "Cell Type-Specific Firing during Ripple Oscillations in the Hippocampal Formation of Humans", J. Neurosci., 28(24), 6104-6110.
Lee, H., et al., 2005, "Phase Locking of Single Neuron Activity to Theta Oscillations during Working Memory in Monkey Extrastriate Visual Cortex", Neuron, 45, 147-156.
Leiser, S. C., et al., 2007, "Responses of Trigeminal Ganglion Neurons during Natural Whisking Behaviors in the Awake Rat", Neuron, 53, 117-133.

(56) References Cited

OTHER PUBLICATIONS

Fujiwara-Tsukamoto, Y., et al., "Synaptic interactions between pyramidal cells and interneurone subtypes during seizure-like activity in the rat hippocampus", J. Physiol. 557.3 (2004), 961-979.

* cited by examiner

SYSTEM AND METHOD OF DETECTING AND PREDICTING SEIZURES

CROSS-REFERENCE TO RELATED APPLICATIONS

This application is the U.S. national phase application filed under 35 U.S.C. § 371 claiming benefit to International Patent Application No. PCT/US2012/040540, filed on Jun. 1, 2012, which is entitled to priority under 35 U.S.C. § 119(e) to U.S. Provisional Patent Application No. 61/492,173, filed on Jun. 1, 2011 and U.S. Provisional Patent Application No. 61/568,404, filed Dec. 8, 2011, each of which is hereby incorporated by reference in its entirety.

BACKGROUND OF THE INVENTION

Epilepsy is a disorder that is prevalent in approximately 0.5-1% of the world's population (Sander, 2003, Curr Opin Neurol 16:165-170) and as many as 30% of these patients do not respond to currently available anti-epileptic drugs (AEDs) (Kwan and Brodie, 2000, N Engl J Med 342:314-319; Kwan and Sander, 2004, J Neurol Neurosurg Psychiatry 75:1376-1381). In patients with temporal lobe epilepsy, the most common form of epilepsy (Engel, J. J., and Pedley, T. A. (2008). Epilepsy: A Comprehensive Textbook 2nd ed. (Philadelphia: Lippincott Williams & Wilkins)), surgical resection of the epileptic focus can be a treatment option. However, controlled evaluations of surgical effectiveness indicate that seizures can be abolished in 60-80% of patients with TLE (Engel, 1996, N Engl J Med 334:647-652; Wiebe, et al., 2001, N Engl J Med 345:311-318), leaving a significant population of patients still affected by seizures. In addition, AEDs typically have adverse side effects since the mechanisms of action affect a wide variety of normal brain processes. Such short and long term side effects include psychomotor slowing, decreased cognition, sleepiness, gait disorders, osteoporosis, neuropathies, cerebellar atrophy, retinal damage, as well as liver, pancreas and bone marrow problems (Loyd et al., 2006, Pharmacoeconomics 23:1167-1181). Moreover, these drugs are not recommended for women of child bearing age, as they are known to be a potential cause of birth defects.

One of the most problematic and frustrating aspects of epilepsy, from the patient's perspective, is the uncertainty about if and when a seizure event will occur (Fisher et al., 2000, Epilepsy Res. 41:39-51). The earliest attempts to find seizure precursors that could be used to predict seizure onset used linear approaches to examine changes in the electroencephalograph ("EEG") before seizure onset. Other approaches included power spectrum analysis of the EEG (Rogowski et al., 1981, Biological Cyberkinetics 42:9-15) or the occurrence rates of interictal spikes (Gotman and Koffler, 1989, Clin. Neurophysiol. 72:7-15), but these were not effective at predicting seizures. In the early 1990's nonlinear techniques began to be applied, including estimates of the largest Lyapunov exponent (Iasemidis et al., 1990, Brain Topography 2:187-201), correlation density (Martinerie et al., 1998, Nature Med. 4:1173-1176), and the dynamic similarity index (Quyen et al., 2000, Eur. J. Neurosci. 12:2124-2134). Therefore, to date, there remains a need for an effective method of detecting and predicting a seizure event. The present invention meets this need.

SUMMARY OF THE INVENTION

In one embodiment, the present invention provides a method for predicting a seizure in a subject. The method comprises recording single neuron activity for a plurality of interneurons, recording the local field potential (LFP), and measuring interneuron synchrony. In one embodiment, detection of a specific pattern of interneuron activity and interneuron synchrony signifies increased likelihood of a seizure. In one embodiment, the method comprises detecting the correlation of interneuron-interneuron pairs. In one embodiment, the method comprises detecting the coherence of interneurons with LFP oscillations.

In one embodiment, the specific pattern includes an increased interneuron firing rate. In another embodiment, the specific pattern includes increased coherence between interneuron action potentials and theta wave oscillations. In one embodiment increased coherence between interneuron action potentials and theta wave oscillations occurs between 1 and 10 minutes prior to a predicted seizure.

In yet another embodiment, the specific pattern includes increased coherence between interneuron action potentials and gamma wave oscillations. In one embodiment increased coherence between interneuron action potentials and gamma wave oscillations occurs between 5 and 30 seconds prior to a predicted seizure.

In one embodiment, the measurement of coherence comprises constructing a spike triggered average of the LFP. In one embodiment, the measurement of coherence is bias corrected.

In one embodiment, the method of predicting a seizure further comprises recording single neuron activity for a plurality of excitatory neurons, for example from pyramidal cell neurons. In one embodiment, single neuron activity is measured in the hippocampus of the subject.

In one embodiment, the detecting of a specific pattern is carried out by an algorithm, where the parameters of the algorithm are automatically generated.

In another aspect, the present invention provides a method of detecting the onset of a seizure. The method comprises recording single neuron activity for a plurality of interneurons, recording the local field potential (LFP), and measuring interneuron synchrony. In one embodiment, detection of a specific pattern of interneuron activity and interneuron synchrony signifies the onset of a seizure. In one embodiment, the pattern comprises increased coherence between interneuron action potentials and ictal spiking. In one embodiment increased coherence between interneuron action potentials and ictal spiking occurs within 30 seconds after the onset of seizure.

In one embodiment, the method comprises detecting a specific pattern of excitatory neuron activity, which includes an increased firing rate of excitatory neurons occurring within 30 seconds after the onset of a seizure. In another embodiment, the specific pattern of excitatory activity includes increased coherence between excitatory action potentials and ictal spiking occurring within 30 seconds after the onset of seizure.

In another aspect, the invention provides methods of preventing a seizure in a subject. The method comprises recording single neuron activity for a plurality of interneurons, recording the local field potential (LFP), and measuring interneuron synchrony. In one embodiment, detection of a specific pattern of interneuron activity and interneuron synchrony signifies increased likelihood of a seizure. The method further comprises administering a therapeutically effective intervention to the subject to prevent the seizure. In one embodiment the intervention is an electrical stimulation. In another embodiment, the intervention is the delivery of a drug.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 7A depicts the means and standard deviations of the uncorrected estimates over all trials for each number of spikes evaluated. FIG. 7B is similar to FIG. 7A, but for the bias corrected estimates. FIG. 7C depicts the variance and bias (inset) of the uncorrected (triangles) and corrected (circles) estimates. Applying the correction does remove the bias, but also adds some variance to the estimate. FIG. 7D depicts the mean squared error in the uncorrected and corrected estimates. Applying the correction can increase the MSE for cases of strong coherence and very few spikes, but for most cases MSE is either reduced or is not affected.

FIG. 8A depicts the means and standard deviations of the uncorrected estimates over all trials for each number of spikes evaluated. FIG. 8B is similar to FIG. 8A, but for the bias corrected estimates. FIG. 8C depicts the variance and bias (inset) of the uncorrected (triangles) and corrected (circles) estimates. Applying the correction does remove the bias, but also adds some variance to the estimate. FIG. 8D depicts the mean squared error in the uncorrected and corrected estimates.

FIG. 9A depicts the means and standard deviations of the uncorrected estimates over all trials for each number of spikes evaluated. FIG. 9B is similar to FIG. 9A, but for the bias corrected estimates. FIG. 9C depicts the variance and bias (inset) of the uncorrected (triangles) and corrected (circles) estimates. Applying the correction does remove the bias, but also adds some variance to the estimate. FIG. 9D depicts the mean squared error in the uncorrected and corrected estimates. In this case, when using a real LFP signal to model coherence, MSE of the corrected PS-SFC estimate is either reduced or is unaffected in nearly all cases.

FIG. 10A depicts the means and standard deviations of the uncorrected estimates over all trials for each number of spikes evaluated. FIG. 10B is similar to FIG. 10A, but for the bias corrected estimates. FIG. 10C depicts the variance and bias (inset) of the uncorrected (triangles) and corrected (circles) estimates. Applying the correction does remove the bias, but also adds some variance to the estimate. FIG. 10D depicts the mean squared error in the uncorrected and corrected estimates. These results are similar to those presented for PS-SFC applied to a sine wave with Gaussian distributed spikes (FIG. 9), and to the FB-SFC for the same model (data not shown).

FIG. 11A depicts the change to the MSE after bias correction for the first 20 spikes. MSE is reduced for all neurons and all numbers of spikes, except for the FB-SFC method when using 2 or 3 spikes. FIG. 11B depicts the change in MSE when divided by the asymptotic coherence to show the change as a percentage of the coherence value.

FIG. 12B depicts the spectrum from the PS-SFC method showing that the frequency band of greatest coherence is different for these different windows. Small windows emphasize high frequencies and depress low frequencies, while the opposite is true of large windows. As depicted in FIG. 12C, for the FB-SFC method, STA's were constructed from filtered signals and all the spikes from the neuron in FIG. 12A. For the STA's shown, the central frequency of the band is 6 Hz, while the fractional bandwidth is 0.67 (solid line), 0.33 (dashed line), or 0.2 (dotted line). FIG. 12D depicts the wideband FB-SFC spectrum, constructed with these same fractional bandwidths. Smaller fractional bandwidths allow for greater frequency resolution, but produce intrinsically lower coherence values. However, varying this parameter does not have the same frequency-dependent effect as the window size for the PS-SFC method.

FIG. 13A illustrates an example of wideband signals collected from four channels of a single tetrode, including action potential waveforms from an interneuron and a pyramidal cell. FIG. 13B depicts a larger collection of waveforms (800 μs duration) from the same interneuron and pyramidal cell as in FIG. 13A, along with these neuron's autocorrelograms normalized to the expected number of counts in a bin. Bin size=1 ms. FIG. 13C depicts the average firing rate, mean autocorrelation lag, and repolarization amplitude of all interneurons and pyramidal cells used in this study. The repolarization amplitude is the amplitude of the waveform 300 μs after the negative peak, normalized to the overall waveform amplitude (max-min). These parameters were used to aid in discriminating putative interneurons from pyramidal cells.

FIG. 14A and FIG. 14B, is a set of graphs illustrating the LFP patterns during the transition to spontaneous seizure. FIG. 14A depicts five examples of spontaneous seizures recorded from 5 different rats. Various diverse types of LFP activity are visible before the onset of sustained ictal spiking (0 s). Initial LFP spikes appear in the first, third and fourth seizure, with slow waves following in the first and fourth seizures. LVF activity and high frequency oscillations are present to some degree or other in all seizures. Horizontal dashed lines in the first seizure symbolize the spike amplitude threshold used to determine the ictal spiking onset. Vertical lines indicate the final resting place of the reverse sliding window used for the same purpose. FIG. 14B is a LFP power spectrogram, computed by estimating the power spectrum in consecutive 2 s bins for each seizure, normalizing to the total power in each bin, smoothing, and averaging over all seizures (n=25). Events a, b, and c (arrows) represent dominant seizure related oscillations, not observed in the background average. White boxes indicate boundaries of time-frequency oscillation windows.

FIG. 15A is an action potential (spike) raster plot of pyramidal cells (dark) and interneurons (light) simultaneously recorded during some example spontaneous seizures (LFP in black trace under each set of neurons). FIG. 15B depicts the average interneuron PETH, using all interneurons and all seizures. Horizontal dashed lines indicate 3 SD significance thresholds. Average firing rate of the interneuron population becomes significantly greater than background beginning 2 seconds before the ictal spiking onset. FIG. 15C depicts the average pyramidal cell PETH is significantly decreased at this same time, but significantly increases at a latency of 8 seconds.

FIG. 16A depicts an example of the normalized firing rate histogram of one interneuron with respect to the ictal spiking onset. (*) denotes bins that have been detected as times of significantly increased firing rate for this neuron. Activation windows of interneurons and pyramidal cells are indicated by the bold vertical dashed lines. Background windows are an extension of this series of 10 s windows occurring at an earlier time, as seen in FIG. 16B and FIG. 16C. FIG. 16B illustrates the fraction of interneurons with detected increases in firing rate in background windows compared to the activation window. The time scale changes in order to visualize activation windows more easily. The horizontal dashed line indicates a significance threshold. FIG. 16C illustrates the fraction of pyramidal cells with increased firing rates in each window, similar to FIG. 16B. FIG. 16D depicts the normalized peak magnitude and duration of firing rate increases for interneurons (light bars) and pyramidal cells (dark bars) measured in background (BG) and activation (ACT) windows. (*) indicates a significant difference between background and activation.

FIG. 17A is the average interneuron coherence spectrogram. Boundaries of the time-frequency oscillation windows (a, b, c) are shown as white rectangles. FIG. 17B illustrates the fraction of all interneurons with significant increases in coherence within the oscillation window boundaries, compared to equivalent duration background windows. The time scale changes from the background (left) to closer to ictal spiking onset (middle). Windows that exceed the significance thresholds (horizontal dashed lines) are considered significant compared to background. Bold vertical lines indicate temporal boundaries of the oscillation windows. FIG. 17C depicts average bias corrected coherence over all interneurons, using only APs occurring within the oscillation windows (OSC) and the average over all background windows (BG). The three panels in FIG. 17C correspond to the coherence estimated in windows a, b, and c. Bold vertical lines in this case represent frequency boundaries of the oscillation windows. FIG. 17D depicts an example of the neuronal firing pattern of two simultaneously recorded interneurons (green and blue) in the transition to seizure. FIG. 17E depicts enlarged one-second samples (horizontal lines under LFP trace) within, and in one case between, the oscillation windows to better visualize the changes in firing patterns. FIG. 17F depicts bias corrected coherence calculated from the APs and LFP shown within these 1-second samples. Green and blue lines correspond to interneurons of the same color.

FIGS. 18A-18C, is a set of graphs illustrating the changes in coherence of pyramidal cells and LFP oscillations during the transition to seizure. FIG. 18A is the average pyramidal cell coherence spectrogram. Boundaries of the time-frequency oscillation windows (a, b, c) are shown as white rectangles. FIG. 18B depicts the fraction of all pyramidal cells with significant increases in coherence within the oscillation window boundaries, compared to equivalent duration background windows. The time scale changes from the background (left) to closer to seizure onset (middle). Windows that exceed the significance thresholds (horizontal dashed lines) are considered significant compared to background. Bold vertical lines indicate temporal boundaries of the oscillation windows. FIG. 18C depicts the average bias corrected coherence over all pyramidal cells, using only APs occurring within the oscillation windows (OSC) and the average over all background windows (BG). The three panels in FIG. 18C correspond to the coherence estimated in windows a, b, and c. Bold vertical lines in this case represent frequency boundaries of the oscillation windows.

FIG. 20A and FIG. 20B, depicts the results of experiments illustrating the changes in neural behavior prior to and during seizure. FIG. 20A illustrates the overlap of interneuron population exhibiting different behaviors. For each type of behavior, listed is the total number of rats and seizures for which this activity was present, along with the total number of interneurons which exhibited it. Of the neurons which exhibited each type of behavior, the fraction which also displayed a different type of behavior (circles) is plotted below (T: Theta Coherence, G: Gamma Coherence, A: Activation (increase in firing rate), I: Ictal Coherence). The expected fraction of neurons (bars) is based on the assumption of independence between different behavior types. (*) indicates the activity types are not categorically independent (p<0.01). FIG. 20B illustrates a summary of different types of observed neuronal behavior at approximate times of occurrence relative to the ictal spiking onset. During the synchrony facilitation stage (displayed truncated here, but −100 to −10 s) more interneurons are coherent with theta LFP and correlated to each other, while pyramidal cells are less correlated to each other. The transition to seizure stage (−10 to 0 s) contains high numbers of interneurons that are coherent with gamma LFP and have increased firing rates. Increased firing rates remain in the beginning of the synchronous recruitment stage, but begin to disappear as pyramidal cells increase activity. Both cell types are coherent with ictal spiking during this stage.

FIG. 24, comprising FIG. 24A depicts average LFP power spectrogram over n=25 seizures, computed in 2 second bins using the same filter bank frequency bands as for SFC. FIG. 24B depicts the pyramidal cell SFC spectrogram (top). This is the average SFC over all pyramidal cells, computed using the initial fixed spike method. Further, the three panels show pyramidal cell SFC calculated using fixed time windows (100 to 4 s, 4 to 0 s, and 1 to 10 s) and the bias correction, for conventional frequency bands (bottom). These values have been normalized to the mean SFC in the background (1 hr to 10 min). Statistical increases from background (asterisks) were detected at the 3 standard deviation level, with adjustments made for multiple comparisons. FIG. 24C depicts interneuron SFC spectrogram (top) and interneuron SFC calculated using fixed time windows and bias correction for conventional frequency bands (bottom).

DETAILED DESCRIPTION

Figure 1:
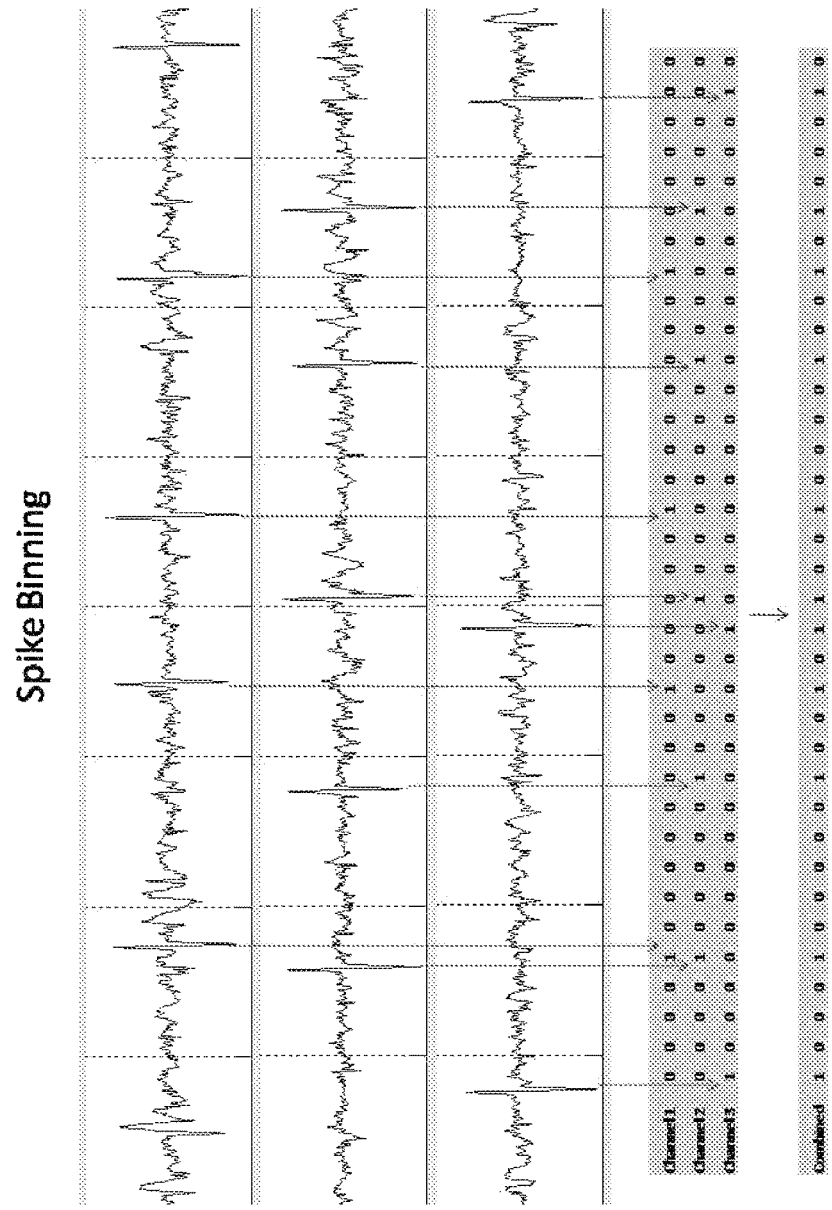
FIG. 1 comprises a chart illustrating a method for binning single neuron spike times. For each single neuron identified on a channel, its spike time is represented by a 1, while units of time or bins when no spike occurs is represented by a 0. If the bin size is 1 ms, there is only one spike per bin for a single cell. Depending on the timescale of the change that is being identified, larger bins can be used and more than one spike can be in a bin.

The present invention provides a method of predicting a seizure event in a mammal, preferably a human, based on measurable increases in neural activity among populations of neurons. By predicting the event before onset, the present invention may provide a warning to the patient and signal for delivery of some type of intervention that would prevent seizure onset, such as an electrical stimulus or drug delivery. In one embodiment, there are measurable increases in neuron firing rate, synchrony, and coherence to local field potential (LFP) before the onset of a seizure, upon which a prediction of a true seizure is based.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

The term "abnormal" when used in the context of organisms, tissues, cells or components thereof, refers to those organisms, tissues, cells or components thereof that differ in at least one observable or detectable characteristic (e.g., age, treatment, time of day, etc.) from those organisms, tissues, cells or components thereof that display the "normal" (expected) respective characteristic. Characteristics which are normal or expected for one cell or tissue type, might be abnormal for a different cell or tissue type.

The term "bursts" as used herein means at least two spikes with an inter-spike interval of less than 10 ms.

A "disease" is a state of health of an animal wherein the animal cannot maintain homeostasis, and wherein if the disease is not ameliorated then the animal's health continues to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

A disease or disorder is "alleviated" if the severity of a symptom of the disease or disorder, the frequency with which such a symptom is experienced by a patient, or both, is reduced.

An "effective amount" or "therapeutically effective amount" is that amount of a compound or electrical stimulation which is sufficient to provide a beneficial effect to the subject or mammal to which the compound or electrical stimulation is administered for a therapeutic treatment.

The terms "patient," "subject," "individual," and the like are used interchangeably herein, and refer to any animal, or cells thereof whether in vitro or in situ, amenable to the methods described herein. In certain non-limiting embodiments, the patient, subject or individual is a human.

A "therapeutic" treatment is a treatment administered to a subject who exhibits signs of pathology, for the purpose of diminishing or eliminating those signs.

As used herein, "treating a disease or disorder" means reducing the frequency with which a symptom of the disease or disorder is experienced by a patient. Disease and disorder are used interchangeably herein.

Ranges: throughout The term "seizure" as used herein means a transient symptom of abnormal, excessive or synchronous neuronal activity in the brain.

The term "recording site", as used herein means a component or region of an electrode array that receives a potential electrical signal from an adjacent neuron for recordation.

The term "synchrony", as used herein means a concurrence of an event between at least two or more things in a designated timeframe. For at least two neurons to be in synchrony, the at least two neurons may fire an electrical signal, or remain "silent", in a concurring manner within a designated timeframe. Alternatively, synchrony can be between at least one neuron and the local field potential. In this case, the neuron fires an electrical signal or remains silent at a specific phase of an on-going oscillation in the local field potential. Alternatively, there could be synchrony between the local field potential recorded from two different microelectrodes. In this case, the phase of the oscillation in the local field potential recorded from one electrode concurs within a designated timeframe of a specific phase of the oscillation in the local field potential recorded from another electrode.

The term "synaptic inhibition", as used herein means any form of the transfer of information between two cells when the sending cell is inhibitory meaning the result of the sending cell passing information to the receiving cell is the hyperpolarization of the receiving cell.

The term "reaching a synchrony level threshold" as used herein means the measured level of synchrony between 1) two or more neural cells, 2) between one or more neural cells and the local field potential (either before or after filtering), or three between the local field potential recorded at more than one location reaches a designated value that represents a seizure will occur. The threshold level can be specific to an individual subject and identified empirically or can be similar across subjects and identified from historical data.

The term "neural spike", as used herein means the recordation of an action potential from a single neuron. An action potential is an all-or-none change in membrane potential of the cell that is described by Hogkin and Huxely, 1950.

The term "moving average filter", as used herein means a system in which the output is the mean of a shifting subset of inputs.

The term "Spike field coherence" (SFC), or "coherence", as used herein refers to a measure of the strength of correlation between the spike times of a neuron or neuron population and the phase of the concurrent local field potential at any given frequency as described more completely by Grasse and Moxon, 2010.

Within this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

DESCRIPTION

The present invention is directed towards methods and systems to predict and detect epileptic seizures. Although epileptic seizures are generally considered to be characterized by synchronous neuronal firing, the role of neuronal synchrony before and during the transition to spontaneous seizure has not been well studied. Because this synchrony is not a sudden occurrence, but rather a gradual build up until the seizure onset, it is possible to predict a seizure by measuring the level of synchrony between neurons. Synchrony in a normal network is modulated via synaptic inhibition. Inhibitory interneurons can hyperpolarize many other neurons simultaneously, temporarily silencing them and then leaving them all free to fire after the inhibition is halted. As such, inhibition may be indicative of hyper synchronous states, and therefore may be a reliable predictor of seizure onset. Further, since neuronal silence is apparently a semi-rare occurrence in a normal brain, it may provide a high level of specificity to the preictal state.

In one embodiment, the methods of the present invention comprise detecting increased firing rate of inhibitory and excitatory neurons. In one embodiment, the methods comprise measuring synchrony between inhibitory neurons. In one embodiment, the methods comprise measuring the coherence of single neuron activity with local field potential (LFP) oscillations. The present invention is based upon the discovery that distinct changes in neuronal activity occur in the preictal state. For example, interneuron activity is found to be coherent with theta wave oscillations and gamma wave oscillations prior to ictal seizure. Further, it is found that interneuron firing rate and synchrony increases prior to ictal seizure. The collective changes in neuronal activity described herein can thus be used to predict and detect seizure. For example, the neuronal parameters described herein can classify the brain state of a subject as being in an interictal state or a preictal state. In one embodiment, the preictal state is the window of time before the onset of the seizure. In one embodiment the preictal window is 2 to 4 minutes before seizure onset. In another embodiment, the preictal window is less than 2 minutes before seizure. In one embodiment, the present invention comprises measuring interneuron synchrony, wherein an increase in interneuron synchrony signifies an increase in the likelihood of an upcoming seizure. The present invention also includes methods and system wherein prediction of seizure initiates a therapeutic intervention, such as drug release or electrical stimulation.

In one embodiment, the invention comprises measuring singe neuron activity. In one embodiment, the methods of the invention comprise measuring single neuron activity in a plurality of neurons. For example, the spike times for single neurons can be monitored. To detect neural spike times, a threshold is applied to sufficiently filtered and amplified signals obtained from multiple electrodes on a multi-site electrode array implanted in the subject. Without limitation, such an array is used as described in U.S. Pat. No. 6,834,200, the entire disclosure of which is incorporated by reference herein as if being set forth herein in its entirety. The aforementioned electrode arrays may also be used in conjunction with wireless systems for transmitting data to processing centers outside of the subject. Without limitation, such wireless systems may include those as described in U.S. Pat. No. 8,086,316, the entire disclosure of which is incorporated by reference herein as if being set forth herein in its entirety.

Single neuron activity can be measured in any brain region. For example, single neuron activity can be measured in the cortex, hippocampus, thalamus, cerebellum, pons, and the like. In one embodiment, single neuron activity can be measure in a sub-region of the hippocampus. For example, measurements can be taken from single neurons in the CA1, CA2, CA3, CA4, and dentate gyms (DG) regions.

If single neuron discrimination is desired, a sorting process may be involved. For example, single neurons can be sorted into excitatory neurons and inhibitory neurons. In one embodiment, neurons are discriminated into interneurons and pyramidal cell neurons. In an aspect of the present invention, detecting changes in the activity of the interneuron population are used to predict and detect seizure. In one aspect, detecting changes in the activity of pyramidal cells are used to predict and detect seizure activity. Further, in one aspect, the changes in each population are used to predict and detect seizure activity.

As contemplated herein, the detection is performed with single neurons or with multiple unsorted neurons. As depicted in FIG. 1, spikes from each channel are binned to the desired temporal resolution. A common bin size is on the order of about one millisecond. Because the present invention looks for time windows where no neuron is firing, data across all channels is combined to obtain a time series of ones and zeros, where a one is designated if any neuron has fired in the specified bin, or zero is designated if no neuron has fired.

Firing Rate

Analysis of data may include identifying changes in the basic firing properties of single neurons, such as firing rate and bursting, for example, as well as a number of relational quantities between multiple single neurons as the animal transition from an interictal state to the ictal state. In order to carry out these analyses, the raw data is streamlined by way of spike binning, as depicted in FIG. 1. Since the duration of an action potential is on the order of about 1 millisecond, the time at which a cell fires is truncated to the nearest millisecond without appreciable loss of data. By representing the time history of a neuron with an array of bins, each 1 ms in length, data is made many times more efficient for processing. For example, in such an array, a "one" may represent a millisecond when the neuron has fired, and a "zero" may represent a millisecond where it has not. Once the data are in this form, a number of quantities are calculated quickly and easily.

The firing rate of each cell is measured by sliding a window of adjustable duration over the array and summing the number of spikes present in the window at each millisecond interval. This is a standard operation used to view changes in firing rate over time (Dayan and Abbott, 2001. Theoretical Neuroscience: Computational and Mathematical Modeling of Neural Systems) and may tell how the activity of the cell changes before and during seizure. It is of particular importance whether the firing of the cells changes as the animal transitions from the preictal state to the ictal state and whether the animal's behavior influences the change in firing rate. Moreover, the firing of the cells during the different seizure states may provide information about the expected number of spikes for the seizure prediction method. In one exemplary embodiment, a sub-population of cells may increase their firing rate, and a sub-population may decrease their firing rate, but the overall population firing rate may not change. In this case, some cells are increasing their firing rate to come-into the synchronous activity, and some are decreasing their firing rate to come-in to the synchrony. This is determined by examining the variance in the average firing rate across the cells as they transition from interictal to ictal state.

In addition to the basic firing rate, cells are known to burst, especially those in the hippocampus. Bursts are best identified with intercellular recordings. However, in the absence of intra-cellular measures, a good estimation of the bursting of cells is made by examining the extracellular spikes times. Further, changes in the patterns of burst in the different regions of the brain may help to define the preictal state. Increases in bursting have previously bee epileptic tissue (Staba et al. 2002, Annals of Neurology, 52(4): 407-415). Therefore, an increase in the number of bursts is seen. The time between groups of spikes or bursts, also known as the inter-burst interval, must be greater than 100 ms. Changes in burst frequency across seizure states are assessed. In addition, the relationship of the bursting to the on-going oscillations, as described herein, is examined. If an increase in bursts in the preictal window is identified, then bursting may serve as a mechanism to entrain other cells and significantly increase the synchrony among cells in the preictal window.

While the aforementioned methods provide a way to measure the firing rate of neurons, it is also possible to extract similar information using a modified version of this method. For example, when implementing the method into a device, the way in which data is processed may be very different. It should be appreciated that other methods of computation may be used, provided the analysis is based on the firing rate of neurons in the periods prior to seizure.

In one aspect of the present invention, prediction and detection of seizure is made through measuring changes in firing rate of neurons or a neuron population. For example, the present invention is partly based on the discovery that interneuron firing rate increases at the onset of ictal spiking. Further, it was found that interneuron firing rate decreases and pyramidal cell firing rate increases seconds after onset of ictal spiking. Thus, in one embodiment of the present invention, prediction and detection of seizure activity comprises measuring the aforementioned changes in firing rate of interneuron and pyramidal cell populations.

In one embodiment, prediction and detection of a seizure comprises detecting an interneuron firing rate of 10-30 Hz. In another embodiment, the methods comprise detecting an interneuron firing rate of 12-20 Hz. In yet another embodiment, the methods comprise detecting an interneuron firing rate of about 15 Hz. It should be noted that in some embodiments, firing rate may vary across subjects. Therefore, in one embodiment, the methods comprise detecting an interneuron firing rate in a time period that is 100-300% of the firing rate recorded in preceding time periods. In another embodiment, the methods comprise detecting an interneuron firing rate in a time period that is 120-200% of the firing rate recorded in preceding time periods. In another embodiment, the methods comprise detecting an interneuron firing rate in a time period that is about 150% of the firing rate recorded in preceding time periods. In one embodiment, the aforementioned ranges of increased interneuron firing rate is detected from 10 seconds before to 10 seconds after seizure onset. In another embodiment, increased firing rate is detected from 5 seconds before to 5 seconds after seizure onset.

In one embodiment, prediction and detection of a seizure comprises detecting a pyramidal cell firing rate of 0.6-2 Hz. In another embodiment, the methods comprise detecting a pyramidal cell firing rate of 0.8-1.5 Hz. In yet another embodiment, the methods comprise detecting a pyramidal cell firing rate of about 1 Hz. It should be noted that in some embodiments, firing rate may vary across subjects. Therefore, in one embodiment, the methods comprise detecting a pyramidal cell firing rate in a time period that is 100-400% of the firing rate recorded in preceding time periods. In another embodiment, the methods comprise detecting an interneuron firing rate in a time period that is 150-300% of the firing rate recorded in preceding time periods. In another embodiment, the methods comprise detecting an interneuron firing rate in a time period that is about 200% of the firing rate recorded in preceding time periods. In one embodiment, the aforementioned ranges of increased interneuron firing rate is detected from 0-20 seconds after seizure onset. In another embodiment, increased firing rate is detected from 5-10 seconds after seizure onset.

Correlation

One of the most important quantities to measure is the characteristics of synchrony between cells. In one aspect of the present invention, changes in synchrony of neuron populations can be used to detect and predict seizure activity.

According to an aspect of the present invention, the window size is adjusted to the specific incoming data, such as the number of channels or the spikes per second, for example. This is a finite window of time that slides across the binned data and checks to see if any neuron has fired inside of it. In one embodiment, the window size may determine how long the silent periods are for an algorithm to "see" them.

While the window is sliding across time, a synchrony time series is constructed with the same temporal resolution as the spike data. This series is zero at default, but when the window encounters a period of silence, it receives a value of one at the first spike time following the silent period. The constructed synchrony series may have frequent positive values during times when neurons are frequently "not firing" simultaneously, but may also be flat when the firing is relatively independent between neurons. This measurement may also be specific to synchronous firing as opposed to overall network depression, or neuronal inactivity, because the synchrony series will only get one positive value per window of silence. Therefore, frequent periods of shorter silence may increase the synchrony measurement more than prolonged periods of silence.

Figure 2:
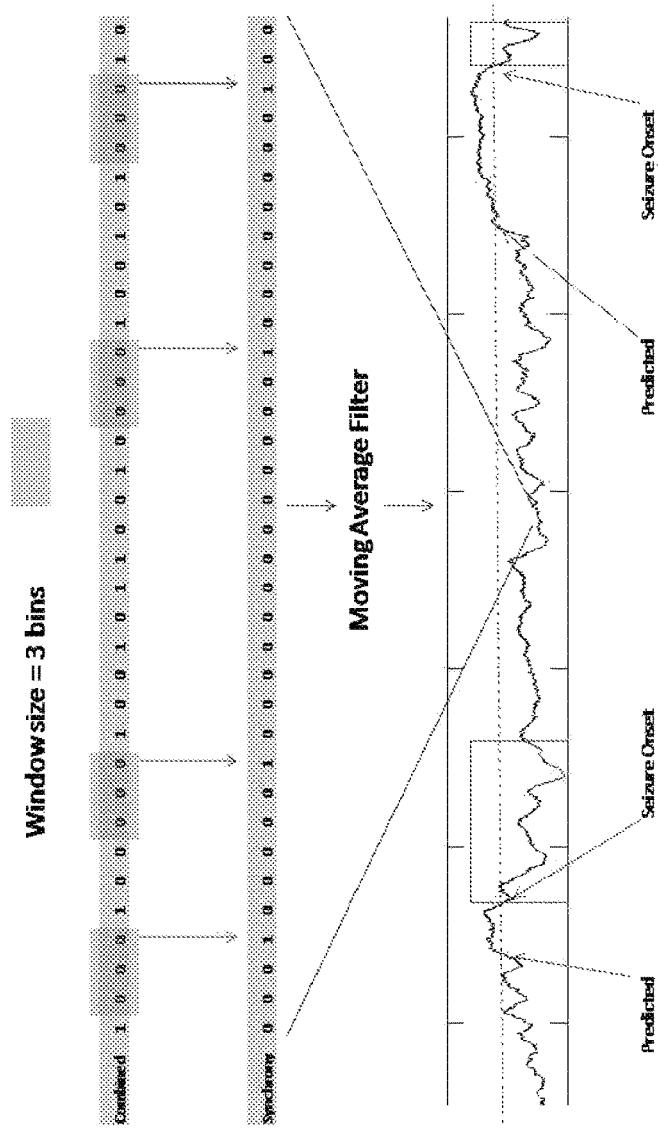
FIG. 2 comprises a chart of combined signaling and the moving average filter generated as a function of the combined single neuron synchrony data.
Figure 3:
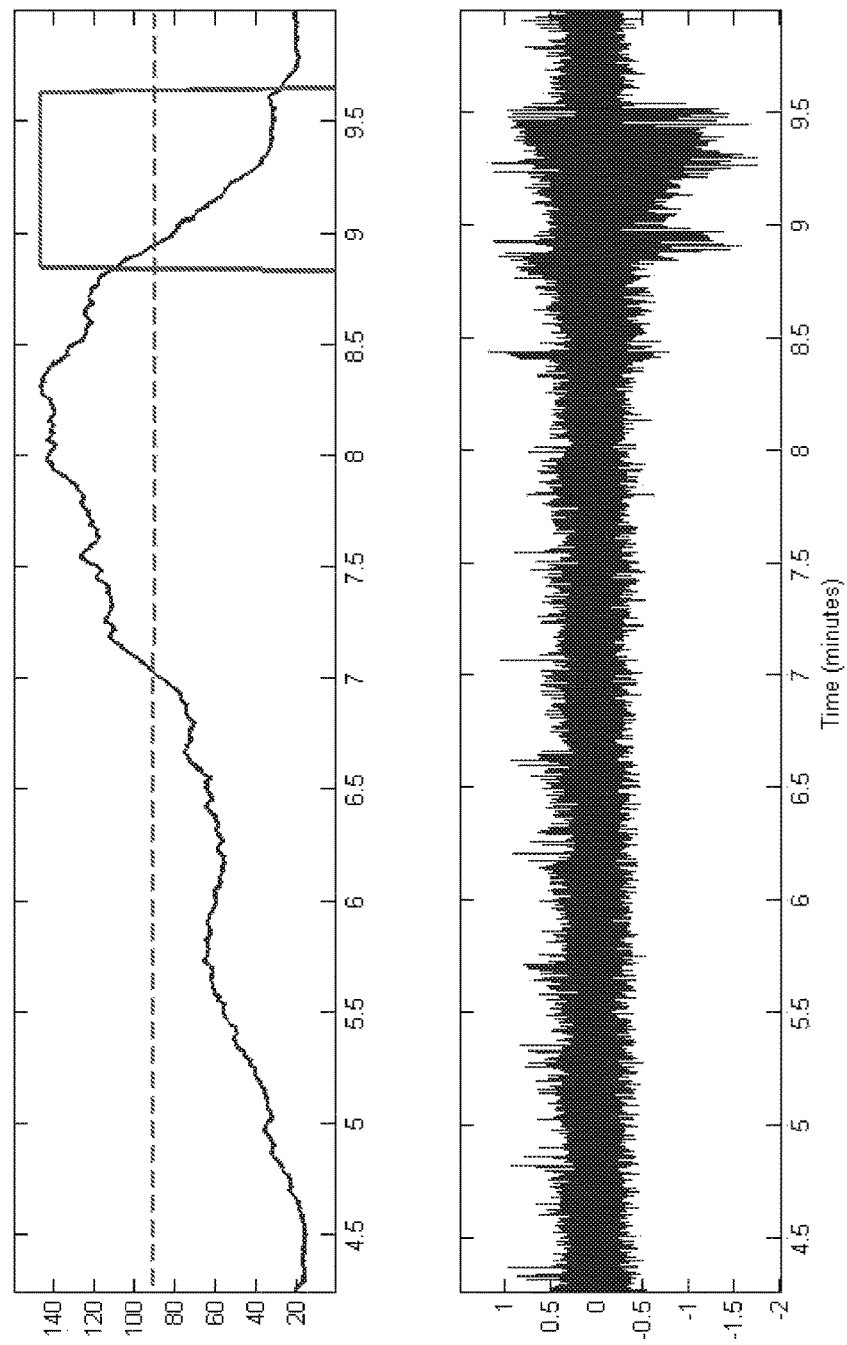
FIG. 3 comprises a chart of an exemplary algorithm output before and during a seizure. The box to the right in the chart represents seizure onset and offset. The dashed line represents a potential threshold. The bottom panel represents the LFP of the seizure.

Once the synchrony series is constructed, the data is transformed into a form that provides a threshold for seizure prediction. As depicted in FIGS. 2 and 3, this is accomplished by applying a moving average filter to the synchrony series. In this way, times where the series has frequent positive values are transformed to a high level, while rare positive values in the series may result in a low level. The length of time over which the data is averaged is considered another parameter. Preferably, it is set to a length that is similar to the amount of time in which preictal changes can be detected. From this point, the threshold is set to the desired value, depending on tolerance for sensitivity and specificity.

Figure 5:
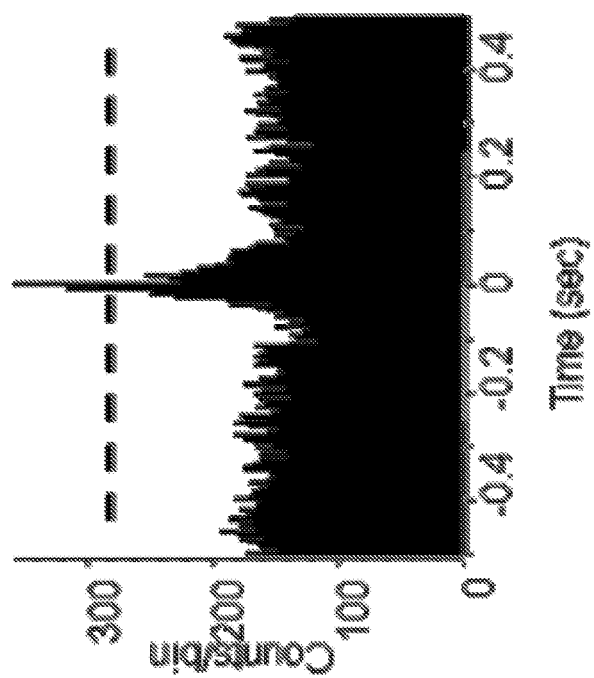
FIG. 5 comprises a cross-correlogram, and is exemplary of a significant cross-correlation between two cells. If the peak of the cross-correlogram is greater than the average of the bins, then the cells are significantly correlated. The time lag between the peak and the reference describe phase of the correlation. The size of the peak describes the degree of correlation. These cells are examined with a 5 ms bin size.

A thorough analysis of the correlations within and between cells is performed to fully assess the synchrony in the ensemble. As a first approximation, a crosscorrelogram is constructed. This process has been previously explained in detail (Eggermont, 1992, J Neurophysiol 68:1216-1228), and is summarized herein. The spikes from one neuron are used as reference points in time. Each spike from the reference neuron is aligned to the center (zero-lag) position on a histogram. This histogram may have a variable overall width, and also bins of variable size depending on the timescale in question. A second neuron's spikes may then be binned in the histogram according to their timing relative to the reference spike. The next spike from the first neuron then becomes the new reference and the process is repeated for a length of time until a sufficient number of spikes have accumulated in the histogram. If the two cells have no correlation, the histogram is flat. If their spikes occur with some relationship to each other in time, they are said to be correlated, as depicted in FIG. 5. By examining each pair of cells across seizure state and animal behavioral state, variables are compared, such as the number of pairs that are significantly correlated, the magnitude of the correlation, and the phase of the correlation, for example. Pairs of cells may include DG-DG, CA3-CA3 and CA3-DG. The degree of correlation for each pair is determined by the size of the peak in the cross-correlogram. The phase of the correlation is defined by the time-lag in the correlogram.

The shape and size of the filter kernel used in the seizure prediction method is estimated from the correlation results. To estimate the parameters of the kernel, the correlograms are used to identify the timescale of synchronization. For each pair of cells with a significant correlation, the timescale of synchronization is determined by the number of adjacent bins in the histogram that are significantly different from the mean. In addition, the phase of the correlations is used to estimate the period of synchronization. The parameters of the kernel are updated so that the resulting predictive method is more sensitive to the synchrony of the ensemble in the preictal window.

Detecting strong correlation may typically be achieved by cross correlation in the case of single neuron signals as described above. However, the possibility that seizure initiation may begin with weak or higher order types of correlations cannot be ruled out. In order to detect these subtle changes, mutual information is used. Mutual information is usually used to assess the information that a population of neurons can convey about a stimulus. Mutual information has previously been used to gain insight into how the brain encodes information (Foffani and Moxon, 2004, J. Neurosci., 24: 7266-7271). Mutual information is also a useful tool to assess aspects of correlation that are non-linear (Scaglione et al., 2011, Proc Natl Acad Sci U.S.A., 108(36): 14956-14961. Mutual information between pairs of neurons across the different seizure and behavioral states are calculated. This may identify forms of correlation among cells that may not be immediately apparent with the linear methods applied above.

In addition to examining the correlation between pairs of neurons, correlations between populations are examined. For example, a population cross-correlation is performed by summing the spikes in a population of cells and performing the cross-correlation on the population. Populations may include cells recorded between different recording sites including different brain regions (CA3 vs. DG). In addition, gravity analysis (Lindsey et al., 1989, Brain Research, 483(2), 373-378) is performed to not only assess how groups of neurons correlate together, but may also give the time course of how these correlations develop.

Another important measure of correlations is the correlations that occur within cells. Auto-correlation analysis is employed on each single unit to assess changes within cell periodicity. The method is similar to the cross-correlation derived above, but the reference point is the cell's own spike time rather than the spike time of another cell. As with the cross-correlation analysis, the number of cells with a significantly auto-correlation are assessed, the magnitude of the correlation is assessed, and the phase of the correlation, or inter-spike interval, is assessed. As before, changes in these variables across behavioral and seizure state are made using a two-way analysis of variance. Also, differences between the auto-correlation of cells within the dentate gyrus and CA3 hippocampus are explored to assess whether significant increases in auto-correlation occur earlier in the preictal window in one population as opposed to the other. This may provide insight into the mechanisms underlying seizure initiation. Finally, a population autocorrelation for each region of the brain studied (DG, iCA3 and cCA3) is made to assess changes within the populations relative to each other.

While the aforementioned methods provide a way to measure the synchrony and coherence between neurons, it is also possible to extract similar information using a modified version of this method. For example, when implementing the method into a device, the way in which data is processed may be very different. It should be appreciated that other methods of computation may be used, provided the analysis is based on the synchrony of neurons in the periods prior to seizure.

In one aspect of the present invention, prediction and detection of seizure is made through measuring changes in the correlation between neurons of given neuron populations. For example, the present invention is partly based on the discovery that interneuron-interneuron correlation increased during oscillation windows prior and during ictal spiking. It was also found that pyramidal cell—pyramidal cell and interneuron—pyramidal cell correlations were not increased in the same oscillation windows. Thus, in one embodiment of the present invention, prediction and detection of seizure activity comprises measuring the aforementioned changes in correlation.

In one embodiment, the methods comprise detecting an increase in the fraction of significantly correlated interneuron-interneuron pairs. In one embodiment, the methods comprise detecting a fraction in a time period that is 100-500% of the fraction in preceding time periods. In another embodiment, the methods comprise detecting a fraction in a time period that is 150-400% of the fraction in preceding time periods. In another embodiment, the methods comprise detecting a fraction in a time period that is 200-400% of the fraction in preceding time periods. In one embodiment, the aforementioned ranges of increased fraction of correlated interneuron-interneuron pairs are detected greater than 10 seconds before seizure onset. In another embodiment, increased fraction of correlated interneuron-interneuron pairs is detected from 10 seconds before to 10 seconds after seizure onset. In another embodiment, increased firing rate is detected from 5 seconds before to 5 seconds after seizure onset.

Coherence

It is also important to understand the correlation between spikes times and on-going oscillations. To identify the relationship of spike probability with an ongoing oscillation, the local field potential is filtered into frequency bands, and a reference within each cycle in the filtered LFP is chosen, and a perievent histogram is built around this reference point. The frequency bands of interest may include the delta, theta, alpha beta and gamma band. Typically, better results are obtained by limiting the highest frequency in the band to no more than twice the lowest frequency in the band. This may help to create a signal that is sinusoidal in nature so that phase reference points may easily be identified. Therefore, cut-off for each band is 1-2 Hz (low delta), 2-4 Hz (high delta), 4-8 Hz, (theta), 8-16 Hz, (alpha), 16-32 (beta) and 32-64 (low gamma) and 64-128 Hz (high gamma), for example.

Figure 6:
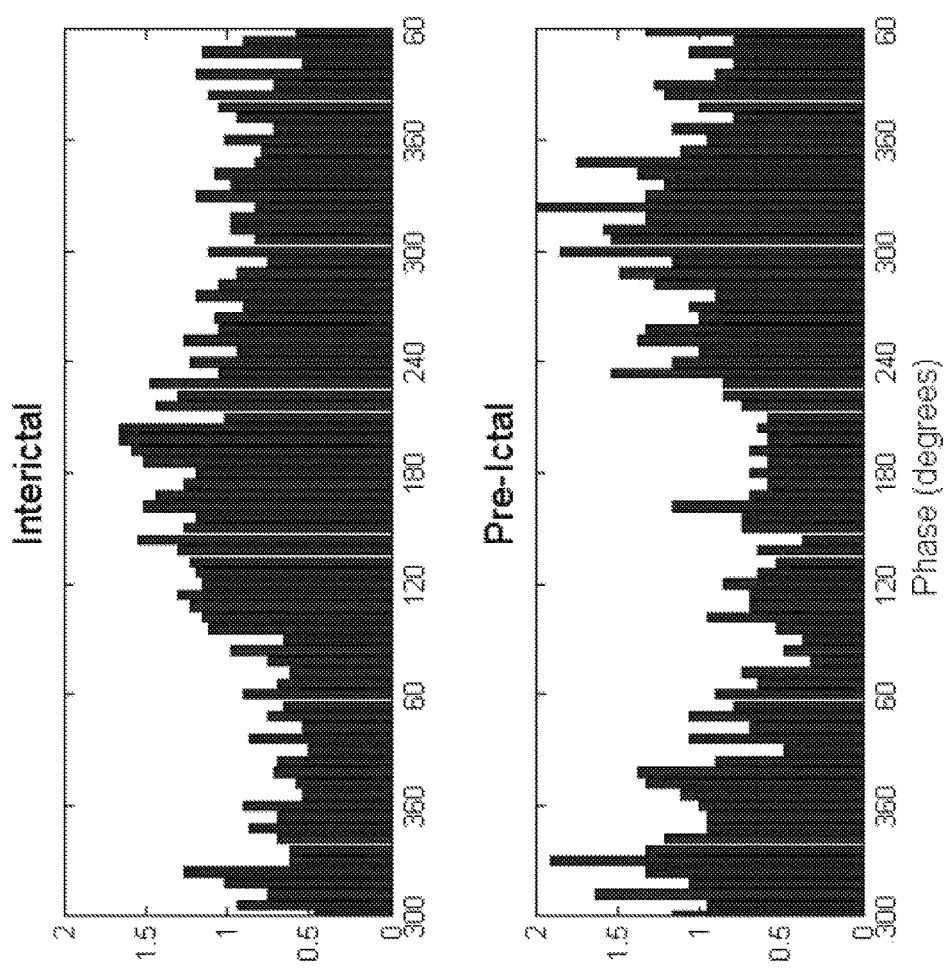
FIG. 6 comprises a set of spike histograms for a single neuron recorded from a rat during the first 8 hours after KA injection. The LFP may first be filtered in the theta (4-8 Hz) band. The reference point for the histogram is 180 degrees representing the trough of the wave. Histogram values are normalized so that 1 represents the average probability over all possible phases. This exemplary cell prefers to fire at 180 degrees during the interictal period, but consistently changed to 300 degrees during a one minute preictal period.

A common reference point is the trough or valley of the cycle and this point can be labeled with phase equal to 180 degrees (O'Keefe and Recce, 1993, Hippocampus 3(3):317-330; Harris, et al., 2002, Nature 417:738-741). Every time a trough occurs in the filtered signal, the spikes from a single neuron occurring before and after it is added to a spike histogram, which is centered on the 180 degree phase mark. In this way, the histogram is built up to show the approximate probability that the neuron fires at each phase of the cycle. As depicted in FIG. 6, the peak of the histogram may define the preferred firing phase for the cell. For many cells, the preferred firing phase may change as the animal transitions from the interictal state to the ictal state. This shift is consistent for the same cell across seizures, and may indicate a characteristic change in overall excitatory or inhibitory input the cell is receiving (Harris, et al., 2002, Nature 417:738-741).

The methods of the present invention comprise evaluating the coherence of single neuron action potentials with oscillations. Non-limiting examples of the types of oscillations useful in the method include LFP oscillations, theta oscillations, gamma oscillations, beta oscillations, hi-gamma oscillations, low-gamma oscillations, ripples, fast ripples, spikes, ictal spiking, and the like. Coherence can be measured by any method known in the art. For example, in one embodiment, coherence can be estimated from spike-triggered average (STA). Further, in one embodiment, coherence can be biased corrected. In some environments, bias is introduced into estimates of coherence due to the limited number of spikes used in the analysis. In general, measuring an infinite number of spikes is not realistic in single neuron recordings. Bias correction, as presented elsewhere herein, provides a method to reduce or eliminate the bias generated from limited and variable number of spikes in a given recording window.

In one embodiment, coherence is estimated from STA in a power spectrum based analysis. In another embodiment, coherence is measured in a filter bank based method. The filter bank method, developed and described elsewhere herein, estimates the coherence between neuronal action potentials and LFP oscillations at any given frequency. This method makes use of a filter bank in combination with existing spike-triggered averaging techniques to separate the phase-locked LFP oscillations from uncorrelated oscillatory activity. The filter bank allows an unbiased comparison of coherence in one frequency band to coherence in another frequency band, since it does not require a Fourier transformation of the spike-triggered average (Grasse and Moxon, 2010, J Neurophysiol, 104: 548-558).

While the aforementioned methods provide a way to measure the coherence of neurons to LFP oscillations, it is also possible to extract similar information using a modified version of this method. For example, when implementing the method into a device, the way in which data is processed may be very different. It should be appreciated that other methods of computation may be used, provided the analysis is based on the coherence of neurons in the periods prior to seizure.

In one aspect of the present invention, prediction and detection of seizure is made through measuring the coherence of neurons or neuron populations with LFP oscillations of different frequency. For example, the present invention is partly based on the discovery that there are distinct phases of interneuron and pyramidal cell coherence prior to and during ictal spiking. For example, it was discovered that beginning minutes before seizure, there is increased coherence of interneurons with theta LFP oscillations. Further, it was found that approximately 10 seconds prior to ictal seizure, there is increased coherence of interneurons with gamma oscillations. Further still, it was found that in the seconds following the onset of ictal spiking, both interneurons and pyramidal cells exhibited increased coherence with ictal spiking. Thus, in one embodiment of the present invention, prediction and detection of seizure activity comprises measuring the aforementioned changes in coherence in interneurons and pyramidal cells.

In one embodiment, prediction and detection of a seizure comprises detecting increased coherence between interneuron action potentials (APs) and LFP theta oscillations. In one embodiment, increased coherence between interneuron APs and theta oscillations is detected from 10 minutes to 10 seconds prior to seizure onset. In another embodiment, increased coherence between interneuron APs and theta oscillations is detected from 5 minutes to 30 seconds prior to seizure onset. In another embodiment, the method, increased coherence between interneuron APs and theta oscillations is detected from 4 minutes to 2 minutes prior to seizure onset.

In another embodiment, the method comprises increased coherence between interneuron APs and LFP gamma oscillations. In one embodiment, increased coherence between interneuron APs and gamma oscillations is detected from 1 minute to 1 second prior to seizure onset. In another embodiment, increased coherence between interneuron APs and gamma oscillations is detected from 30 seconds to 5 seconds prior to seizure onset. In another embodiment, the method, increased coherence between interneuron APs and gamma oscillations is detected from 15 seconds to 10 seconds prior to seizure onset.

In another embodiment, the method comprises detecting increased coherence between interneuron APs and LFP ictal oscillations. In one embodiment, increased coherence between interneuron APs and ictal oscillations is detected from 0 seconds to 30 seconds after seizure onset. In another embodiment, increased coherence between interneuron APs and ictal oscillations is detected from 5 seconds to 20 seconds after seizure onset. In another embodiment, the method, increased coherence between interneuron APs and ictal oscillations is detected from 8 seconds to 15 seconds after seizure onset.

In another embodiment, the method comprises detecting increased coherence between pyramidal cell APs and LFP ictal oscillations. In one embodiment, increased coherence between pyramidal cell APs and ictal oscillations is detected from 0 seconds to 30 seconds after seizure onset. In another embodiment, increased coherence between pyramidal cell APs and ictal oscillations is detected from 5 seconds to 20 seconds after seizure onset. In another embodiment, the method, increased coherence between pyramidal cell APs and ictal oscillations is detected from 8 seconds to 15 seconds after seizure onset.

In one embodiment, detecting an increased coherence of a neuron population to LFP oscillations comprises detecting an average coherence of 0.05-1. In another embodiment, the methods comprise detecting an average coherence of 0.1-0.5. It should be noted that in some embodiments, correlation may vary across subjects and across neuron type. Therefore, in one embodiment, the methods comprise detecting the coherence of a neuron or neuron population in a time period that is 100-500% of the coherence detected in preceding time periods. In another embodiment, the methods comprise detecting the coherence of a neuron or neuron population in a time period that is 150-400% of the coherence detected in preceding time periods. In another embodiment, the methods comprise detecting the coherence of a neuron or neuron population in a time period that is about 200-300% of the coherence detected in preceding time periods.

In one embodiment, detecting an increased coherence of a neuron population to LFP oscillations comprises detecting an increase in the fraction of neurons with significant increases in coherence in a given time period. For example, in one embodiment, the method comprises detecting a fraction of neurons with a significant increase in coherence in a given time period that is 100-500% of the fraction measured in preceding time periods. In one embodiment, the method comprises detecting a fraction of neurons with a significant increase in coherence in a given time period that is 150-400% of the fraction measured in preceding time periods. In one embodiment, the method comprises detecting a fraction of neurons with a significant increase in coherence in a given time period that is 200-300% of the fraction measured in preceding time periods.

Algorithm

Based on the seizure prediction method, as described herein, a detection algorithm may provide an approximately 100% true seizure recognition rate. This is important because to fully relieve the patient's burden of this debilitating disorder, the patient must have confidence that there will be some warning of the imminent seizure. This seizure prediction method, when paired with an appropriate intervention, may virtually eliminate the symptoms of epilepsy. Additionally, the seizure prediction method may also maintain a false positive rate that is not 'too high'.

In addition to the traditional definition of a false positive rate, which is described as: (fp/(fp+tn)), another manner of reporting this value is in false positive occurrences per unit time. Yet another manner is to report two, far more useful definitions in addition to the standard false positive rate. For example, the first is the number of false positives divided by the number of seizures (fp/(tp+fn)). This value may give an intuitive idea of the maximum number of false predictions made per positive occurrence. The second value to report is the fraction of interictal time spent in the false positive predictive state, as opposed to the true negative state. This may take into account the prediction duration along with the specificity.

In one embodiment, a false positive rate at or below 100% (number of false positives/total number of seizures) is preferred. Further, the fraction of false positive time to less than 10% of the total negative time may also be preferred.

As long as there are a sufficient number of neurons to record from, the particular identify of a neuron is not relevant to perform the predictive method as described herein. In some embodiments, the parameters are adjusted for sleep wake cycles or other circadian type rhythms.

The present invention provides a method suitable for adjusting to patient-specific parameters, and therefore, the present invention provides a distinct advantage over existing methods, in that there is always a significant amount of per-subject specificity in the values of the parameters. The sources of such variability among subjects are many. For example, the individual quality of the seizures for each patient may greatly affect the parameters. Moreover, the precise placement of the electrodes relative to the focus of the seizure may have an important impact. Therefore, the fact that these parameters are specific for an individual patient may not affect the accuracy of the present invention. Also, when set within a few weeks of the electrode implant surgery, the ability to predict a seizure is stationary over long time periods and need to be adjusted infrequently, such as on the order of months.

While predicting seizures based on parameters derived from the first 2-3 seizures per subject, parameters are updated after each seizure event to fine tune and/or improve the prediction rate.

The systems and methods of the present invention comprise an algorithm that predicts an upcoming seizure. In one embodiment, the algorithm predicts a seizure from 1-10 seconds prior to ictal spiking associated with seizure activity. In another embodiment, the algorithm predicts a seizure 15-45 seconds prior to ictal spiking. In yet another embodiment, the algorithm predicts a seizure 1-2 minutes prior to ictal spiking. In yet another embodiment, the algorithm predicts a seizure 2-4 minutes prior to ictal spiking. In yet another embodiment, the algorithm predicts a seizure 5-30 minutes prior to ictal spiking. In yet another embodiment, the algorithm predicts a seizure greater than 30 minutes prior to ictal spiking.

In one embodiment, the systems and methods of the present invention comprise a support vector machine (SVM) or other artificial neural network (ANN). For example, an SVM can be trained to recognize specific neural activity patterns associated with interictal, preictal, or ictal brain states. The different neural activity patterns associated with each state can be identified using single neuron firing rates, correlations between neurons and synchrony between neurons, between neurons and the local field potential and between the local field potentials recorded at different electrodes. However, the present invention is not limited to use of an SVM or ANN. Rather, any algorithm or device capable of detecting the patterns described herein can be used in the present invention. For example, the methods can comprise kernel methods (KM), which are a class of algorithms for pattern analysis. Any such algorithm may be used to discriminate the brain state of a subject in order to detect or predict seizure activity in accordance with the present invention. In one embodiment, the parameters and form of the algorithm are generated automatically, for example by a device, machine, or computer. That is, in one embodiment, the algorithm can be generated without a human observer.

Intervention

In one aspect of the invention, prediction or detection of a seizure initiates a stimulus, which may be either a drug delivery or electrical stimulus to forestall the seizure. For example, the subject can receive an electrical stimulus via an implanted electrode to a particular brain region or multiple brain regions. The stimulus may be generated by a wireless signal from a wireless transceiver. Likewise, a subject may be stimulated to receive an amount of drug by a drug delivery device. For example, a drug delivery device may be implanted into the brain of the subject. In some embodiments, the drug can be administered to the blood stream or CSF of a subject. Any drug or electrical stimulus that prevents or mitigates a predicted or detected seizure may be used with the systems and methods of the present invention.

Understanding the role of synchrony in the generation or spread of seizures may guide new drug or device therapies which are able to act more specifically and effectively to disrupt the seizure generation process. Most human epileptic seizures are studied by recording cortical or depth EEG signals, which tell limited information about the underlying network phenomena involved the transition to seizure. On the other hand, neuronal excitation, inhibition and synchrony have been well studied in brain slices, but seizures must be modeled by changing the chemical environment or inducing an electrical stimulus. Since the mechanisms at work in these studies of induced seizure-like events may be very different from the mechanisms underlying the spontaneous transition to seizure, there was a need to examine the neuronal behaviors (excitation, inhibition, synchrony, etc) when seizures occur without provocation.

The present invention identifies the specific changes in single neuron activity that occurred around the transition to seizure, and describes the use of this information to develop new seizure prevention strategies. In one embodiment, the systems and methods of the present invention comprise a method to estimate neuronal coherence between neuronal action potentials and LFP oscillations without any dependence on oscillation frequency or the neuronal firing rate. In one embodiment, this method makes use of a filter bank in combination with existing spike-triggered averaging techniques to separate the phase-locked LFP oscillations from uncorrelated oscillatory activity. The filter bank allows an unbiased comparison of coherence in one frequency band to coherence in another frequency band, since it does not require a Fourier transformation of the spike-triggered average. In one embodiment, a bias correction is implemented, which eliminates the dependence of the estimator on the number of action potentials used in the process. This is important for analyses where the coherence was to be estimated in a fixed time window and the number of action potentials emitted in the window was variable. As described elsewhere herein, the spike field coherence estimation method was evaluated on multiple models of simulated data and real neuronal data, and was shown to reduce the mean squared error of the estimate in nearly all conditions.

As described herein, estimation of neuronal synchrony identifies three distinct stages of synchronous activity in the seizure generation process, based on firing patterns of interneurons. These synchrony patterns were shown to be consistent across different seizures and rats, and suggest that these seizures are not simply mediated by increasing global excitation. While not wishing to be bound by any particular theory, it is thought that these stages represent different underlying mechanisms based on the dominant oscillation frequencies that interneurons are coherent with. For example, since the medial septum and entorhinal cortex are known to produce the hippocampal theta oscillations, the high coherence observed between interneurons and theta field oscillations in the minutes before seizure may be due to a dysfunction in these regions. Furthermore, inputs to the hippocampus at theta frequency have been shown to be optimal for hippocampal synapse potentiation. Therefore, this could be a mechanism for facilitating hypersynchronous seizure-initiating events.

In one embodiment, the neuronal firing patterns are utilized to train an algorithm to predict and detect seizures. In one embodiment, the algorithm comprises a sliding window function. In one embodiment, the methods comprise the use of a trained SVM to classify each moment in time as an interictal or preictal state. In one embodiment, the algorithm, when optimized and trained on seizures from the same subject, can predict 100% of seizures with a 30% false positive rate. This performance is well suited to inform a stimulation system of when to deliver the stimulus, as current false positive stimulation rates are comparable with this level. In one embodiment, the algorithm can predict seizures 10 seconds before ictal spiking.

In one embodiment, knowledge of alterations in neuronal firing patterns related to seizures allows for methods for preventing or aborting seizures by disrupting the altered patterns. For example, existing electrical stimulation devices may stimulate the brain either after the seizure is already manifested electrographically, or without regard to when seizures occur. If stimulation is delivered just before the seizure initiates, however, it will likely be more effective than trying to abort a seizure that has already begun.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Example 1

Prediction and Detection of Seizure Activity

The materials and methods are now described.
Kainic Acid Lesion Surgery

The Kainic Acid ("KA") lesion model is well established (Cavalheiro et al., 1982, Electroencephalography and Clin. Neurophysiol. 53:581-589; French et al., 1982, Neurosci. 7:2525-2536; Ben-Ari, 1985, Neurosci. 14:375-403; Mathern et al., 1993, Electroencephalography and Clin. Neurophysiol. 87:326-339; Babb et al., 1995, Italian J. of Neurolog. Sci. 16:39-44; Bragin et al., 1999, Epilepsia 40:1210-1221; Bragin et al., 2005, Epilepsia 46:1592-1598). Rats (N=10, Sprague Dawley, 200-300 g) are anesthetized with Nembutal (50 mg/kg i.p.) and placed in a stereotaxic apparatus for surgery (Cartesian Research, Sandy, Oreg.). The depth of anesthesia is controlled by the pinch reflex throughout the surgery and supplemental injections of 0.05 ml Nembutal is given as necessary. Sterile procedures are used and all NIH Animal Care and Use guidelines are followed. The skin is incised midsagittally. The soft tissue is retracted, and the periosteum of the skull is removed. A craniotomy is performed over the CA3 region of the hippocampus at 5.6 mm posterior to bregma and 4.5 mm lateral to bregma (Paxinos and Watson, 2007, The Rat Brain in Stereotaxic Coordinates, Sixth Edition, Academic Press, New York, N.Y.). A cannula is inserted to a depth of 5.5 mm below bregma and kainic acid (400 ng/200 nL) is injected over a 20 minute period unilaterally into left posterior CA3 hippocampus. Rats are monitored for the next 12 hours during which they are expected to have 3-5 seizures per hour. Over approximately 5 months, the rats are checked daily for visible signs of health and are weighed weekly.
Electrode Implantation Surgery The methods for implantation are similar to those described by Moxon et al., 1999, Brain Research 825(1-2): 75-85; Moxon et al., 2004, IEEE Biomed Eng., 51: 647-656; Foffani and Moxon, 2004, J. Neurosci. Methods, 135: 107-120; Foffani and Moxon, 2004, J. Neurosci., 24: 7266-7271; Tutunculer, 2005, Pediatrics International: Official Journal of the Japan Pediatric Society, 47(4): 434-439, the entire disclosures of which are incorporated by reference herein as if being set forth herein in their entireties. Notably, the present invention may implant tetrode arrays.

Rats are anesthetized with Nembutal (50 mg/kg i.p.) and placed in a stereotaxic apparatus for surgery (Cartesian Research, Sandy, Oreg.). The depth of anesthesia is controlled by the pinch reflex throughout the surgery and supplemental injections of 0.05 ml Nembutal is given as necessary. The skin is incised midsagittally. Sterile procedures are used and all NIH Animal Care and Use guidelines are followed.

The soft tissue is retracted, and the periosteum of the skull is removed. Three craniotomies are performed to implant the tetrode style microelectrode arrays. The first array is placed into the anterior CA3 region of the hippocampus ipsilateral to the KA lesion side of the brain 1.5 mm more anterior at approximately 4.0 mm posterior to bregma, 3.0 mm lateral. The second is placed in the dorsal CA3 region of the hippocampus contralateral to the KA lesion site, 5.6 mm posterior to bregma and 4.5 mm lateral to bregma. The third craniotomy is placed in the ipsilateral side the brain relative to the lesion 2.0 mm anterior to bregam and 1.6 mm lateral for an array that is inserted at a 45° angle to reach the ipsilateral dentate gyrs near the lesion. All coordinates are based on the atlas of Paxinos and Watson. Four stainless steel screws are firmly attached to the skull to ensure proper anchoring of the electrodes. Each array then is lowered slowly into the brain one at a time (approximately 10 μm/minute). Recordings are performed during the implant to ensure proper placement. For the arrays placed into the CA3 hippocampus, the array is slowly lowered through the cortex, corpus collusum and CA1 hippocampus. For both contralateral and ipsilateral arrays, the goal is to insert the electrode into the pyramidal cell layer. Therefore, arrays are continuously lowered until the typical CA3 pyramidal cells' firing pattern is encountered (Moxon et al., 1999, Brain Research, 825(1-2): 75-85; Deadwyler, et al., 1979, Brain Res. 161:211-225; Deadwyler, et al., 1979, Brain Res. 169:29-43) If necessary, a few animals can be tested with high impedance, single electrodes during an acute mapping procedure followed by histology to identify the proper electrode placement using previously published methods (Leiser and Moxon, 2006, Neuron 53:117-133). The ipsilateral array is placed approximately 3.5 mm deep and the contralateral array to be place approximately 5.5 mm deep. The dentate gyrs array is placed at a 45° angle and inserted approximately 6 mm so that the recordings sites are in the ipsilateral dentate gyrs approximately 1.6 mm lateral, 4.0 mm posterior and 4.2 mm ventral to bregma. Holes in the skull around the microelectrode may then be filled with agar gel to protect the exposed brain tissue, and electrodes are secured to the skull with dental cement to create an electrode cap to attach a recording headstage during subsequent recording sessions. The incision may then be closed with surgical staples, the wound is covered with antibiotic ointment and the rat is allowed to recover from anesthesia in a heated environment. Rats are monitored frequently until they are fully recovered from anesthesia, and then once per day until recordings begin. During recording procedures, the animals are continuously videotaped and monitored periodically.

Single Neuron Recording

Single neurons are recorded from the arrays almost continuously for two months. Methods are similar to previously published methods for recording awaked freely moving animals (Moxon et al., 1999, Brain Research 825(1-2): 75-85; Chapin, et al., 1999, Nature Neurosci. 2:1-7; Leiser and Moxon, 2007, Neuron 53:117-133). However, a wireless recording system is used here (TBSI, Inc.). The rats are lightly anesthetized with isoflurane to immobilize them until the wireless headstage (15RadioHS_025_36_24H, TBSI, Inc.) is attached to the electrode cap on the rat's skull. This system uses an external battery pack and allows for up to 15 channels of recording for 24 hours before the batteries need to be replaced. The signals are preamplified (gain 600, bandpass 0.8 Hz-6 kHz) and the outputs are continually broadcast to a receiver. The receiver then passes the information through ribbon cables to a Multi-Neuron Acquisition Processor (MNAP) (Plexon inc. Dallas, Tex.), which enables online neuronal spike sorting from all recording sites simultaneously and storage of LFPs from selected channels. The MNAP further filters and amplifies the signals reaching a total gain of 10,000-20,000. Single neurons are discriminated from each recording site (see below). The spike times for all discriminated neurons are recorded during the experiment along with timestamps of the onset of the stimuli and all of the waveforms. Signals are stored in Nex (Plexon, Inc., Dallas, Tex.).

Tetrode Method

Recordings with tetrodes have been demonstrated to have superior performance at discriminating between single neurons than either single microwires or stereotrodes (Gray et al., 1995, J. Neurosci. 63:43-54). Because the detection method combines the neurons from all channels recorded, there may not be a need to discriminate among single neurons for the final clinical device. For a complete analysis of the data, single neuron data is reported. The tetrode design alleviates errors in sorting between nearby neurons. Because the amplitude of a signal recorded from a single source only changes with respect to the distance from that source (provided the properties of the neuron are stable), the direction from which a signal is originating may be unknown. This may become problematic if there are multiple nearby neurons with similar action potential amplitudes. Instead, a tetrode can compare the same signal as received by four independent recording sites to distinguish between signals from different directions. The simplest method yielding the best results compares waveform amplitude on every combination of channels (Gray et al., 1995, J. Neurosci. 63:43-54). Each channel of the tetrode is assigned a voltage threshold that, when crossed, becomes stored as a waveform for that channel. Plotting the waveform amplitudes on axes corresponding to each possible channel pair (6 pairs total) may show clusters of points where consistent amplitudes have occurred at the same time. These clusters, if sufficiently well defined, may represent single neurons. More detailed descriptions have been published elsewhere (O'Keefe and Recce, 1993, Hippocampus 3:317-330; Emondi et al., 2004, J Neurosci Methods, 135(1-2): 95-105), the entire disclosures of which are incorporated by reference herein as if being set forth herein in their entireties.

Definition of a Single Unit Compared to a Multi-Unit

Real-time spike sorting software (SortClient, Plexon Inc, Dallas, Tex.) is used to capture action-potential waveforms that exceed a voltage threshold crossing, and sort them in real time according to their shape. Neural signals are monitored on an oscilloscope, on a computer screen using the SortClient software, and through audio speakers. To discriminate single units, template matching is used, to define the waveform shape and ensure clear separation between units before the start of the recording session. All waveforms are saved and reexamined. For each recording site, the number of single units recorded are determined using off-line analysis of the collected waveforms, sampled at 45 kHz. To ensure single unit separation (i.e. prevent activity of neighboring cells from mixing with the activity of the principal neuron) after the recording session, the spike times and saved waveforms for the duration of each cell's recording session are tested to ensure that only single units were recorded. First, interspike interval (ISI) histograms are generated for each potential cell, and only those cells with no spikes within the cell's refractory period (approximately 1 ms) are considered for further testing. Waveforms from each potential cell may then be aligned and tested for changes in waveform shape and clustering of principle components (PCs) (WaveTracker, Plexon Inc, Dallas, Tex.). Only cells with no significant changes (F-statistic, WaveTracker) in their waveform shape or PCs collected during the recording session are considered to be single units. These methods may ensure reliability in unit isolation and single-unit separation (see Nicolelis et al., 2003, and Ribeiro et al., 2004).

Perfusion and Tissue Processing

Animals are sacrificed after their two month recording period. The brains are removed and the tissue stained using immunohistological procedures similar to previously published studies (Moxon et al., 2004, IEEE Trans. Biomed. Eng. 51:647-656; Shumsky et al., 2005, Kao et al., 2006). The animals are euthanized with an overdose of Nembutal and then perfused transcardially with 0.5 L of ice cold PBS followed by 0.5 L of ice cold 4% paraformadelhyde. The tissue is blocked and placed in 30% sucrose solution to equilibrate for three days.

Following the equilibration period, the tissue is sliced coronally using a cryostat into 30 μm sections. These sections are collected serially, maintaining the order of the slices. Standard immunohistochemical methods are used to stain for the cell types of interest to identify the location and size of the lesion created by the KA injection and the position of microelectrode arrays. A Timm stain is performed on adjacent sections to identify mossy fiber sprouting (Buckmaster and Dudek, 1998, J. Comp. Neurol. 385: 385-404). Within two days of sectioning, the tissue on the slices is ringed with rubber cement to create wells and prepared for staining which consists of using primary antibodies for the cell type of interest, followed by a secondary antibody for immunofluorescent staining. To prepare tissue for staining, the sections are washed in PBS and then blocked with goat serum. The primary antibody may then be applied at a 1:1000 dilution and incubated overnight. For primary antibody exposure, the first set of tissue slices are exposed to GFAP (Sigma, Inc). GFAP stains the antigen glial fibrillary acidic protein on astrocytes which helps to identify electrode placement. The isotype used is Rabbit IgG at a concentration of 4.0 μg/mL. The second set of tissue slices are exposed to NeuN (Chemicon International). NeuN stains the antigens in the nuclei of neurons. The isotype will be Mouse IgG1 at a concentration of 1.0 to 5.0 μg/mL. The third and final set of tissue slices are stained for cell bodies using a Nissl stain to mark all cells and define the extent of the KA lesion. Following the primary antibody incubation period or the Nissl, the tissue is washed in PBS and incubated in the secondary antibody for 2 hours at a 1:100 dilution. The tissue will then be washed again and coverslipped with Vectashield (Vector Labortories) to help preserve tissue and stain quality.

Sample Size

The sample size required may include sufficient numbers of seizures with sufficient interictal data to calculate the true/false positive rate. For statistical purposes, to determine the number of seizures, a 95% confidence that the sensitivity is better than 99.98% is desired. Since the seizure rate is modeled by a binomial distribution and, a priori it is planned to have a 100% true positive rate, then approximately 300 seizures may be needed. This is estimated from the binomial distribution:

$$P(x)=N!/[x!(N-x)!]p^x q^{N-x}$$

where:
P(x)=confidence interval (95%)
N=total number of seizures
x=the number of seizures predicted (100%)
p=assumed sensitivity, q=1-p (99.98%)

About 20 rats are recorded for two months, providing about 300 seizures for analysis. A similar analysis can be done to identify how much interictal time is necessary to have confidence in our false positive rate. By solving the maximum error of estimate for the number of samples, the maximum sample size is determined. A 95% confidence that the false positive rate is within 0.05 of the true rate is desired. Without knowledge of what the false positive rate is, the amount of interictal time that would be required may be, at most, 500 times the prediction duration. Since the maximum prediction window is 2 hours, up to 1000 hours of interictal time is collected. Therefore, two hour samples are collected each day that a seizure does not occur from each rat.

It is expected that there is variability not only between animals, but also between seizures in the same animal. For this reason, it is not efficient to collect a minimal amount of seizures in a maximal amount of rats. Neither would the opposite be appropriate. Since there are limited recording resources and limited time, both seizures/animal and the number of animals are maximized. This is accomplished by allowing approximately 16 seizures to occur per animal and by using a total of 20 animals.

Single Neuron Analysis

For each single neuron analysis, the variables of interest, such as firing rate, burst rate, and correlation rate, for example, is compared using a three way analysis of variance (ANOVA). The first factor is the seizure state with three levels (interictal, ictal and preictal). The second factor is the behavioral state with three levels (QUIET, ACTIVE and SLEEP). The third factor is brain region with three levels (DG, iCA3 and cCA3). The analysis is repeated for each preictal window (2, 4, 8, 16, 32, . . . , 128 minutes). For ANOVA's that produce a significant F-test, the Sheffe post-hoc test is used to identify which means contributed to the effect. The preictal window that shows the greatest significant change in the variables compared to the interictal is considered the appropriate time scale for the pre-seizure window used to test the algorithm. It is possible that every variable will not have the same time-scale of change. In this case, the variables for which the algorithm is most sensitive are used to select the appropriate window. If necessary, the algorithm is tested at multiple windows.

This analysis may also be used to more fully understand the mechanisms underlying seizure generation in this KA induced model of spontaneous seizures.

Algorithm Analysis

To perform a complete analysis of the seizure prediction method, a rigorous statistical approach is needed. With some exceptions, prediction methods to date have failed to demonstrate themselves properly due to four main deficiencies in analysis. First, the data set used only contains time directly leading up to seizure, and not interictal time sufficiently far away from a seizure. Since the preictal duration is not known, a correct false positive rate cannot be calculated during times that are potentially preictal. Therefore, the false positive rate must be assessed on data that is arguably interictal. Second, the analysis should also report quantities that are the most useful to the construction of an online prediction system. One quantity commonly left out is the total time in which a seizure was predicted to be imminent. This is very important if the prediction duration is long. To evaluate the amount of time the predictor is in a state of positive prediction, this quantity should be included. Third, the results were never compared to that of a random predictor. This is mainly a problem when high false positive rates are present because a random predictor that makes a lot of predictions may seem to have a high sensitivity to seizures by chance. Fourth, the algorithm parameters were selected or optimized on the same data that it was tested on; the so called in-sample optimization. This type of analysis is obviously flawed because a true predictor will contain no information about the future state of the brain. A rigorous analysis of any predictor should account for all the problems listed above if it is to be considered for use in humans.

The false positive rate is identified when the true positive rate (# predicted/total # seizures) is equal to 100%. This approach is considered successful if the false positive rate (#FP/total number of seizures) is less than 300%. Preferably, the false positive rate is less than 100%.

In addition, error rates of our algorithm are compared with those of a random predictor with the same prediction duration. The output of the algorithm varies continuously, so the simplest way to measure error rates is to transform the output into a binary predictor by applying a threshold. Each second the algorithm output is above threshold, it is a positive prediction of a specified duration. By allowing the threshold and prediction duration to vary as parameters, a two dimensional parameter space can be created with values representing error rates.

Subtracting the error rates of a random predictor in the same parameter space gives an estimate of the algorithm performance beyond that of chance.

There are measurable increases in synchrony of neurons approximately 2 to 4 minutes before the onset of a seizure, upon which a prediction of a true seizure is based. These measurable increases may also apply to a chronic KA lesion model of spontaneous seizures. For example, KA is injected into the posterior hippocampus and the rats left for 5 months to reach a state of spontaneous seizures. Based on previous data, it has been demonstrated that rats at this time are likely to have approximately two seizures a week (Bragin et al. 1999, Epilepsia, 40(9): 1210-1221). At 5 months, tetrodes are implanted into the dentate gyms (DG), CA3 hippocampus anterior to the lesion (iCA3) and contralateral CA3 hippocampus (cCA3). The animal is given a week to recover from the surgery and may then be connected to a wireless headstage that continuously records single neuron activity and local field potentials (LFP) from each region. The animals may then be placed in a Plexiglas chamber, and a camera is setup for continuous video recording of the animal's behavior. The animals are recorded almost continuously for two months. Off-line data mining techniques are used to identify potential candidate seizures in the LFP. Single neuron, LFP and video data collected in a two hour window around a seizure is stored, and used to identify changes in the neuronal activity in a preictal window before the seizure, and further to determine the time scale of this window. Such time scales are single minutes, tens of minutes or even an hour, for example. In addition, sufficient neuronal activity at random times more than 24 hours away from a seizure is collected to serve as interictal periods for comparison. In one example, 500 times more interictal data than the preictal duration is collected. The candidate seizures are examined by a neurologist to identify each individual seizure from the candidates, and mark the unequivocal onset of the seizure and the offset of the seizure.

Single neuron activity is examined with two approaches. For example, the seizure onset times are used to divide the data into three states. The first state is the ictal state, as identified by the neurologist. The second state is the interictal period, which is the random periods collected more than twenty-four hours away from the seizure. The third state is the preictal state, which is a designated window of time before the onset of the seizure. In one exemplary embodiment, this window is 2 to 4 minutes before seizure onset. In other embodiments, this window size is of other variable lengths, provided such window effectively aids in the prediction of the potential seizure event.

Further, changes in firing rate, correlations and relative phase of firing compared to on-going oscillatory activity in the LFP is identified and used to determine the role of neuronal activity in the generation of seizures, and may further be used to determine the onset of the preictal state.

As contemplated herein, the changes in single neuron activity as the rat transitions from interictal to the preictal state, and then to the ictal state, is determined.

As contemplated herein, changes in neuronal activity as the rat transitions from interictal to preictal state is used to specifically and selectively predict seizures.

Experimental Overview

Figure 4:
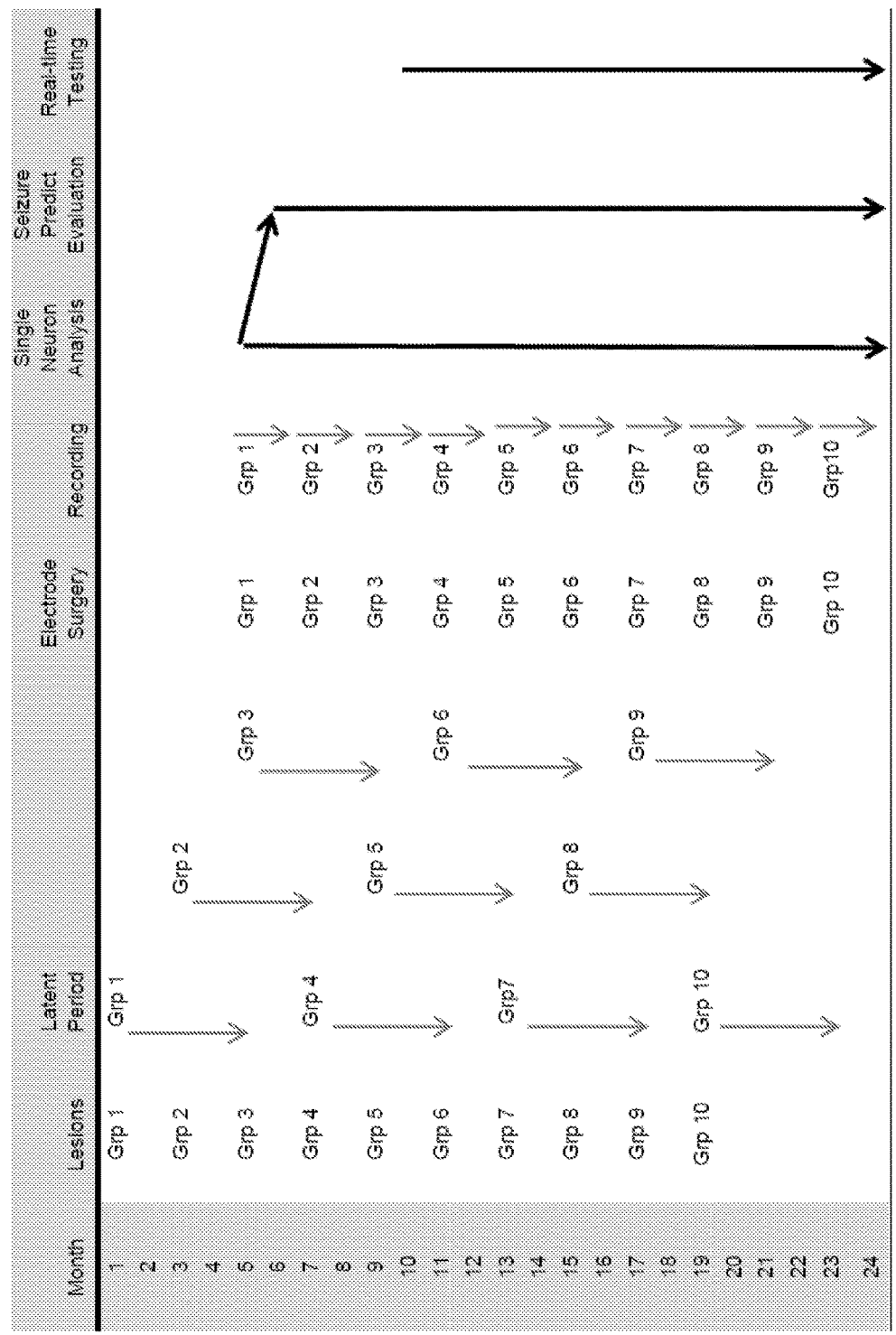
FIG. 4 comprises a table illustrating sample groups, and an experimental timeline for each sample group as they proceed through creation of lesions, surgery, recording, and data analysis.

Experiments are performed on 10 groups of two rats each, for a total of 20 animals as depicted in FIG. 4. A group of animals are injected with KA every two months. The animals may then progress through a latent period until they develop spontaneous seizures. After the incubation period, the projected rate of seizures is about two per week (Bragin et al., 1999, Epilepsia, 40(9), 1210-1221).

The animals are allowed one week for recovery from an electrode implantation procedure and may then be continuously recorded for two months. During this recording period, approximately 16 seizures per animal is expected. Based on the first few seizures, the parameters of the seizure prediction method is identified, and subsequently used on-line and in real-time to predict subsequent seizures. Animals may then be sacrificed and the brains prepared for histological analysis of the KA lesion and electrode placement. In one example, the first 2 to 3 seizures per animal are used to assess neuronal activity during the interictal, preictal and ictal states, to identify the time scale of changes in synchrony before seizure onset and the parameters of the predictive method. The predictive method is adjusted based on this new information, and the parameters set. Then, the predictive method is tested on the remaining seizures, both on and off-line. During the recording periods, single unit and LFP data are continuously assessed and the effectiveness of the method to predict seizures is evaluated. To determine whether the parameters of the predictive method are stationary within or across the animals, a "leave-one-out" analysis is made, and subsequently the derived parameters are tested on the excluded seizure event (or animal).

Data Storage and Mining for Seizures

While data is continuously recorded from the rats and stored, only interictal data and data around seizures are needed to perform the contemplated analysis described herein, and therefore only these data sets may require long-term storage (Wong et al., 2007, J. Neurophysiol., 97(3): 2525-2532). In one embodiment, an automated method is used to identify candidate seizures from the EEG. For each candidate seizure, data representing approximately 2 hours before the seizure and 30 minutes after the seizure is recorded and stored. Based on this window, seizures are predicted within 2 to 4 minutes before seizure onset. Preferably, at least 10 times the expected preictal duration around the seizure is used in order to examine the transition from preictal to ictal. Therefore, storing data approximately 120 minutes before seizure and 30 minutes after seizure may provide sufficient data to fully determine the dynamics of neuronal activity just prior to seizure onset.

In addition to potential preictal data immediately surrounding the seizure, 500 times the preictal duration is used to fully assess the false positive rate. To accomplish this, two hour periods of time per day, more than 24 hours away from a seizure are randomly selected to serve as good interictal periods. This data may further be stored for off-line analysis to test the seizure prediction method. This is used to illustrate the predictive method has a low enough false positive rate to be effective. As stated previously, candidate seizures are confirmed by a qualified neurologist as true seizures. For each seizure event, the earliest electrographic changes are noted and used for the seizure prediction method (Wong et al., 2007, J. Neurophysiol., 97(3): 2525-2532).

Single Neuron Ensemble Analysis

Based on a single-neuron ensemble analysis, changes in synchrony within the network are evaluated in order to identify the parameters of the predictive method. Further, a single-neuron ensemble analysis may identify the relationship of single neuron activity near the focus of a seizure to the generation of the seizure.

To identify the parameters of the predictive method, populations of neurons are simultaneously recorded. The seizure prediction method requires the identification of the duration of the preictal window, and the parameters of a filter kernel that may enhance the representation of synchrony within the network. Several timescales are examined to determine the appropriate window within which changes in neuronal activity can be used to define the preictal state. For example, a two minute window is used to perform each single neuron analysis, as described herein. This analysis is repeated on widows of increasing size by powers of two, such as windows of 2, 4, 8, 16, . . . , and 128 minutes, for example. Preferably, the preictal window is within 4 minutes of the seizure onset. Alternatively, the same analysis is performed, starting with the two minute window and decreasing the window size by the same power of two, provided there is enough time for an effective change for seizure prediction.

As mentioned previously, the parameters of a filter kernel to enhance the identification of changes in synchrony among the cells are defined. These parameters may include its shape and period, as well as the bin size for single-neuron spike times. These are estimated using results from the single neuron ensemble analysis as contemplated herein. Generally, single-neurons should first be discriminated. Next, the data is separated by the animal's behavioral state, such as "Quiet", "Active", or "Sleep", and also by seizure state, such as interictal, preictal or ictal. Several preictal windows are tested, ranging from 2-128 minutes. Finally, the firing rate, correlation and relative phase of firing compared to on-going oscillatory activity in the LFP of the ensembles are examined, and used to identify changes in neuronal activity across the behavioral states and seizure states. For example, a two-way analysis of variance is used. For each analysis, variables that assess changes in neuronal activity are defined. For each variable, a separate two-way analysis of variance is performed to assess changes in the variable between seizure state and across behavioral state. The first factor is the seizure state with three levels, and the second factor is behavior with three levels.

Development of Algorithm

A weighted average of the combined spike times of all the cells to produce a population function is created. Next, a linear filter to identify the periodicity of synchrony that is predictive of a seizure is applied. For example, a simple sinusoidal function is sufficient. The time scale of this sinusoid is estimated from the cross-correlation analysis defined for a single-neuron analysis.

The spike density of any given position in the train may represent the fraction of cells that are firing at that moment. Knowledge of the timescale in which spikes cluster together during synchrony may determine the size of filter kernel to use. The most pronounced periods of clustering may have durations of approximately 30 milliseconds, as do the periods of inhibition. This may be different, depending on the particular subjects and, moreover, it may need to be tuned for each individual patient.

As described herein, a sinusoidal kernel with a length and period of 64 ms is used. The outcome of applying this filter kernel to the spike train is an array with a magnitude proportional to the average difference in spike density between the current moment in time and 32 ms prior. The total value of this array in each 1-s epoch is normalized to the total number of spikes in that second, and then the series of 1-s epochs are subject to a simple moving average filter of length 120 s. In summary, the value of the predictive method at any given moment is equal to the normalized absolute value of the difference in spike densities between successive 32 ms periods, averaged over the past two minutes. This value may increase prior to seizure (2-4 minutes) such that a prediction that is better than simply chance about when the onset will occur. A threshold is applied to discriminate between abnormally high levels of synchrony that predict a seizure and synchrony levels that may not be indicative of a seizure. The higher the threshold, the less likely it may be to select a false positive, but the more likely we are to miss a seizure. By keeping our false positive range below chance, the predictive method may predict 100% of the seizures within minutes of the seizure onset as verified by the local field potential.

Because this algorithm is based on measures that can be quantified directly from the data, the parameters of the algorithm and even the form of the algorithm could be generated automatically without a human observer.

Example 2

Spike Field Coherence Estimation

The coherence between oscillatory activity in local field potentials (LFP) and single neuron action potentials, or spikes, has been suggested as a neural substrate for the representation of information. The power spectrum of a spike triggered average (STA) is commonly used to estimate spike field coherence (SFC). However, when a finite number of spikes are used to construct the STA, the coherence estimator is biased. Introduced herein is a correction for the bias imposed by the limited number of spikes available in experimental conditions. In addition, an alternative method for estimating SFC from an STA by using a filter bank approach is presented. This method is shown to be more appropriate in some analyses, such as comparing coherence across frequency bands. The proposed bias correction is a linear transformation derived from an idealized model of spike-field interaction but is shown to hold in more realistic settings. Uncorrected and corrected SFC estimates from both estimation methods are compared across multiple simulated spike-field models and experimentally collected data. The bias correction was shown to reduce the bias of the estimators, but add variance. However, the corrected estimates had a reduced or unchanged mean squared error in the majority of conditions evaluated. The bias correction provides an effective way to reduce bias in an SFC estimator without increasing the mean squared error.

The relationship between local field potential (LFP) oscillations and single neuron action potentials, or spikes, has become a topic of increasing interest. The significance of coherence between spikes and LFPs has been shown to be important for auditory and visual sensory processing (Eggermont and Smith, 1995, J Neurophysiol 73:227-245; Fries, et al., 1997, Proc Natl Acad Sci USA. 94:12699-12704;

Gray and Singer, 1989, Proc Natl Acad Sci USA 86:1698-1702), motor tasks (Courtemanche, et al., 2002, J Neurophysiol 88:771-782; Donoghue, et al., 1998, J Neurophysiol 79:159-173; Murthy and Fetz, 1996, J Neurophysiol 76:3949-3967), memory representation (Harris, et al., 2002, Nature 417:738-741; Lee, et al., 2005, Neuron 45:147-156; O'Keefe and Recce, 1993, Hippocampus 3(3):317-330; Le Van Quyen, et al., 2008, J Neurosci 28(24):6104-6110), attention (Fries, et al., 2001, Science 291:1560-1563), and neurological disorders (Foffani, et al., 2007, Neuron 55:930-941; Goldberg, et al., 2004, J Neurosci 24:6003-6010). For example, neurons activated by an attended stimulus are likely to be synchronized with gamma band (30-70 Hz) LFP oscillations (Fries, et al., 2008, J Neurosci 28:4823-4835). This is traditionally demonstrated through a measure called spike field coherence (SFC), which gives the strength of coupling between spike times and the phase of LFP at any given frequency. However, due to limitations in the finite amount of data available to measure this coherence, methods developed to study this phenomenon can only estimate the coherence. Therefore, a better understanding of the quality of the estimation is needed if biological inferences are to be drawn from this measure.

While it is easily describable as a qualitative physiological phenomenon, the exact quantitative definition of SFC is a matter of debate. No single definition can capture all the aspects of the spike-field relationship. Therefore the best that can be done is to select an aspect of physiological importance and model it to define a quantity that represents this aspect well. The strength of phase coupling between two continuous signals is traditionally inferred through the quantity called coherence, defined as the squared magnitude of the cross-spectrum divided by the product of the autospectra (Bendat and Piersol, 1971, Random Data: Analysis and Measurement Procedures, Wiley). The same definition of coherence has also been used by some to describe spike field coupling, however this definition is not considered here. Instead examined herein are estimators of alternatively defined quantities, based on the spike triggered average (STA), which also represent spike field coupling strength. This type of SFC estimator emphasizes different physiological information than estimators that begin in the frequency domain. For example, an STA-based estimator weights its value equally by spike, whereas traditional coherence weights all sections of the time series equally, regardless of spike density. Although the quantities estimated by the STA-based methods presented here are not mathematically equivalent to the traditional definition of coherence, they are also referred to as coherence or SFC hereafter.

The STA was originally constructed to measure postsynaptic potentials of dorsal roots (Mendell and Henneman, 1968, Science 160:96-98; Mendell and Henneman, 1971, J Neurophysiol 34:171-187), but has since been applied to LFP. For each spike, an LFP segment of fixed duration is taken that is centered on the spike. All spike-centered segments are added together and divided by the number of spikes. This produces an average of the LFP happening within some window of each spike. One existing method for estimating coherence from the STA uses a normalized power spectrum of the spike triggered average (STA) to estimate the coherence (Fries, et al., 1997, Proc Natl Acad Sci USA. 94:12699-12704). Another method, introduced here, uses a filter bank approach to estimate SFC from the amplitude at the center of the STA. However, in any estimate, there are two sources of potential error: bias and variability.

To define the bias problem, these sources of error must be identified. In the theoretical case, one would have an infinite amount of data from which to measure the asymptotic (population) coherence. In addition, this data would be second-order stationary (Brillinger, 1981, Time Series—Data Analysis and Theory Expanded, Holden-Day, Inc)) in that the coherence does not change over time. However, since an infinite number of spikes are never available, a more realistic scenario is to have a finite subset of this data from which to estimate the sample coherence. In practice it is common to perform single trial estimation averaging over all available spikes. However this creates a condition where it is unknown whether the error in this single trial estimate comes from bias or variability. To investigate these sources of error, one can estimate the coherence of simulated data over multiple trials using a fixed number of spikes in each trial. In this way, a single trial estimate is defined as the quantification of an STA constructed from a given number of spikes, n. A multi-trial estimate of the coherence, therefore, can be indexed by two factors: the number of trials, m, and the number of spikes in a trial, n. In the analyses presented here, m is chosen to be large enough, M, that gives an accurate measure of the expected value and variance of the coherence for a given n. This framework is then used to examine the bias and variance associated with the expected value of the coherence as the number of spikes is varied.

The bias is defined as the difference between the expected value of the coherence estimate for a given number of spikes, and the asymptotic value of the coherence. The asymptotic coherence, c, is equal to the estimated coherence, $\hat{c}$, as the number of spikes, n, approaches infinity.

$$c(f) = \lim_{n \to \infty} \hat{c}_n(f) \cong \hat{c}_N(f) \qquad (1)$$

Both the asymptotic and the estimated coherence vary as a function of frequency, f. Because an infinite number of spikes never exist in practical situations, the asymptotic coherence is approximated as $\hat{c}_N$, where, N denotes a number of spikes large enough so that the estimated coherence is a good approximation of the asymptotic coherence. These two terms, $\hat{c}_N$ and c, are used interchangeably for the remainder of this article and are both referred to as the asymptotic coherence.

The fact that the bias of the coherence estimator arises from the limitation of the finite number of spikes used in the STA can be best understood by the following thought experiment. Consider an experiment where a total number of spikes, N, are recorded simultaneously with an LFP. Furthermore, the spikes and LFP are independent of one another and the asymptotic coherence is therefore zero. To evaluate an estimate of coherence, one could perform a single trial estimate using all of the spikes. Alternatively, one could select a subset of spikes, n, multiple times, to obtain an expected estimate of the coherence over the multiple trials. If there were no bias, the expected value of the estimated coherence and the asymptotic coherence would be the same and equal to zero. However, there is a difference, and therefore a bias, because the power of the STA is dependent on the number of spikes. A single coherence estimate using a large number of spikes, N, will always be less than or equal to the expected value of the coherence using a subset of n spikes (n<N) for each trial. The case of zero coherence is a specific example of the general behavior exhibited by the STA in cases of nonzero coherence, as will be demonstrated later.

A correction for this bias is proposed that enables an estimation of SFC that is not dependent on the number of spikes used in the STA and, in the methods, derive this correction analytically. To test this bias correction approach, it is applied to both the power spectrum based (PS-SFC) and filter bank based (FB-SFC) spike field coherence methods identified above and described in the methods. Different models of spike distributions and LFP are used to evaluate the effect of the bias correction on the estimate of the SFC. It is found that the correction reduces the effect of finite number of spikes (the bias) on the estimate, but adds variance. However the mean squared error (MSE) of the estimates is reduced after correction in the majority of cases simulated. It is shown that these results are consistent with the effect of the bias correction on experimentally collected data.

The materials and methods employed in these experiments are now described.

In order to assess the effect of the presented bias correction, the bias, variance and MSE, of the uncorrected and corrected PS-SFC and FB-SFC estimation methods were evaluated using simulated and experimentally collected data. As stated elsewhere herein, bias was defined as the difference between the expected value of the coherence estimate for a given number of spikes and the asymptotic coherence. Variance, Var, was defined as the average squared deviation of each single trial estimate from the expected value of the estimate for the same conditions. MSE was defined as the sum of the bias squared and the variance. These sample statistics were calculated over a large number of trials, M, in order to accurately approximate the population statistics they represent. Each is a function of frequency of oscillation, f, and indexed by the number of spikes, n, used in each trial, m. Denoting $\langle \ldots \rangle_m$ as the arithmetic mean and $E[\ldots]$ as the expected value operators, $$\langle \hat{c}_n(f) \rangle_m - \hat{c}_N(f) \cong E[\hat{c}_n(f)] - \hat{c}_N(f) \equiv \text{Bias}(\hat{c}_n(f)) \quad (2)$$

$$\text{Var}(\hat{c}_n(f)) \equiv \frac{1}{M-1} \sum_{m=1}^{M} (\hat{c}_{m,n}(f) - \langle \hat{c}_n(f) \rangle_m)^2 \quad (3)$$

$$\text{MSE}(\hat{c}_n(f)) \equiv \text{Bias}(\hat{c}_n(f))^2 + \text{Var}(\hat{c}_n(f)) \quad (4)$$

Simulations were performed by creating an artificial coherence strength. This simulated coherence was dependent on the model of spike distribution used, and could be controlled by parameters in the models. The models used for evaluation consisted of two simple components: an LFP signal and a spike distribution with respect to the oscillation phase. Each component could be one of two types, so four different models were possible. The value of the simulated coherence was set by assuming ideal conditions (LFP is a pure sine wave) and computing the spike distribution parameters necessary to achieve a desired asymptotic coherence. These estimation qualities were evaluated on all simulated and experimentally collected data.

Simulations

The LFP signal used in the simulations was represented as either a 50 Hz sine wave or as a real LFP signal filtered to an approximate 50 Hz wave. In the latter case, the raw (0.5-500 Hz) signal was digitized and filtered to 45-55 Hz. See data collection methods for details. Filtering was performed using a zero phase (MATLAB filtfilt.m) FIR filter with a Hamming window and order 2000. Both LFP representations had a sampling rate of 2 kHz. The oscillatory signal was used as a reference for placing spikes according to the different spike distributions, so as to control the coherence strength at 50 Hz. The simulations could have been repeated at any other frequency band, but to reduce redundant results this was the only point on the frequency spectrum to be examined in simulations.

Spikes were distributed around a selected phase of the 50 Hz oscillation by one of two distributions: a binary distribution or a Gaussian distribution. These distributions were centered on an arbitrary phase of the oscillation called the preferred phase. The binary distribution is described by mixing coherent spikes with incoherent spikes, so that each spike was either coherent or not. Coherent spikes occurred at exactly the preferred phase of the oscillation, while the incoherent spikes occurred as a random Poisson variable, independent of the LFP. The parameter that controlled the coherence strength was the ratio of coherent spikes to total spikes. Specifically the simulated coherence was given by $$\gamma = p_2 \quad (5)$$

where p is the probability of choosing $n_X$ coherent spikes from the total number of spikes. The Gaussian distribution is a more realistic model, where individual spikes were neither fully coherent nor fully incoherent. Instead all spikes were randomly assigned a time of occurrence, but according to a Gaussian distribution. The mean of this distribution occurred at the preferred phase of the oscillation and the standard deviation was the parameter that controlled coherence strength. Therefore a narrower distribution would result in a higher coherence. This relationship between standard deviation of the spike distribution, σ, and the simulated coherence, γ, is a Gaussian-weighted sum of sine waves, given by $$\gamma \equiv \left( \int_{-\infty}^{\infty} \frac{1}{\sigma\sqrt{2\pi}} \exp\left(-\frac{t^2}{2\sigma^2}\right) \cos(2\pi ft) dt \right)^2 \quad (6)$$

where the standard deviation is in units of time.

For each trial, a 10 minute section of signal was generated or selected at random, depending on the LFP representation. A phase was chosen randomly to be the preferred phase of the 50 Hz oscillation. Each spike then required another random selection to determine which cycle in the 10 minute section it would be placed. Lastly the exact spike time was obtained according to the distribution being used and referenced to the preferred phase in the chosen cycle. Once 2000 spikes were placed to represent the total population, the estimation methods were applied. These methods used up to 1000 of these spikes to create an STA, estimating the SFC after the addition of each new spike. The bias correction was also applied to the estimates after each new spike. The end result of a single trial was four estimates (uncorrected and corrected PS-SFC and FB-SFC) of coherence from 1 through 1000 spikes. Results beyond 100 spikes were not shown because the effect of the bias correction was less pronounced and it became difficult to visualize differences in estimation statistics beyond this point. For each of the four simulations, M=1000 trials were performed to accurately determine bias and variance.

Analysis of Experimentally Collected Data

In order to demonstrate efficacy of the bias correction on real data, several neurons were recorded simultaneously during a 1 hour interval for each of 3 rats. From initial examination of the broad coherence spectrum, it was determined that these hippocampal neurons were most coherent with the theta band (centered on 6 Hz). Therefore, the analysis was restricted to this frequency band. It would technically require an infinite number of spikes to determine the asymptotic coherence perfectly; however a very good approximation was determined by the following method. First the uncorrected coherence was estimated from all available spikes, N, in the time period. It was desired to ensure that this quantity would change very little with any amount of additional spikes (N+1, N+2, . . . , N+k), assuming stationary coherence. For a given SFC estimate using N spikes, adding more spikes will change the estimate by a maximum of 1/N. This is true in general because the maximum rate of decrease in a coherence estimate as the number of spikes increases is given by the case of independent spikes and LFP (zero asymptotic coherence). Here, the expected coherence estimate at a given number of spikes, n, is equal to 1/n, and therefore this is the maximum possible amount this estimate can change as n increases. Since an estimate of any nonzero asymptotic coherence will not change more than for the case of zero asymptotic coherence, the upper bound on the amount of uncertainty in a coherence estimate is given by 1/n. In examining the data, only the neurons that displayed uncertainties of less than 1% of the asymptotic coherence were chosen. This left 9 neurons, which had asymptotic coherence values ranging from 0.005 to 0.1. Once these values were determined, estimation methods were evaluated in a similar manner to that of simulation. Coherence was estimated for each number of randomly chosen spikes, n, ranging from 1 to 100. The spikes chosen did not necessarily occur in succession, but were selected with uniform probability from the entire recording. For each value of n, 1000 trials were performed and the mean and variance of the estimated coherence was calculated before and after bias correction.

Estimation Methods

The PS-SFC was estimated in a manner similar to others (Fries, et al., 2001, Science 291:1560-1563). First an STA was constructed from the raw signal with a window 150 ms wide around the spike. The power spectral density was estimated by use of a multitaper approach with 2 orthogonal tapers specified from discrete prolate spheroidal sequences (MATLAB pmtm.m). The number of tapers was kept to a minimum in order to isolate the power in the band surrounding the 50 Hz point on the spectrum. With these parameters the frequency resolution was 10 Hz. This resolution implied a fractional bandwidth of 0.2 at 50 Hz; the same bandwidth as the filter used for simulation. For each LFP segment used to construct the STA, the power spectrum was estimated using the above technique. These spectra were then averaged together to obtain the average spectrum of the LFP segments. Finally the normalized spectrum was obtained by dividing the power spectrum of the STA by the average spectrum of the LFP. This normalized power spectrum of the STA is the definition of SFC for this method.

$$\hat{c} = \frac{Power_{STA}}{\langle Power_{LFP} \rangle} \qquad (7)$$

When this method was applied to experimentally collected data, a lower frequency band (5.4 Hz-6.6 Hz) was examined. Therefore, the width of the STA time window was changed to 400 ms, in order to better estimate the power spectrum. All other parameters were the same as for the simulations.

The FB-SFC method, introduced here, uses a filter bank to measure the amplitude of each frequency component in the STA spectrum. Instead of constructing the STA from the raw LFP, the signal was first filtered into a narrow band (45-55 Hz) as described above. In general, this technique would require multiple filters to estimate power over a spectrum of interest, but since simulated spikes were correlated only to the 50 Hz oscillation, only one filter was required. An STA was constructed from the filtered signal in the same way as is done for the raw signal. For each LFP segment, the absolute peak heights were found and averaged together to obtain the average peak height for the segment. Each segment was then normalized by dividing it by its average peak height. The STA was rectified and the peak closest to the center was found. Each segment was individually normalized so there is no need to normalize the central peak. Since the signal bandwidth is narrow, the STA is approximately sinusoidal with Power≅Peak$^2$/2. Therefore the square of the normalized peak amplitude is the definition of SFC for the FB-SFC method and is analogous to the power ratio from the PS-SFC definition.

$$\hat{c} = Peak^2_{STA} \qquad (8)$$

The FB-SFC method estimates coherence at the time each spike occurred, instead of over the entire STA window. This gives it different frequency dependence properties than the PS-SFC. These properties are examined elsewhere herein.

Surgery, Data Collection, and Spike Sorting

Experimentally collected data were recorded from rats chronically implanted with tetrode bundles. All procedures were approved by the Institutional Animal Care and Use Committee at Drexel University and followed NIH Guidelines. Three male Long Evans rats (300-350 g) were given atropine (0.05 mg/kg), anesthetized with isoflurane (2%) and placed in a standard stereotactic apparatus for electrode implantation. A craniotomy was preformed and a bundle of eight tetrodes were slowly lowered into the CA3 region of the dorsal hippocampus, and sealed in place with dental acrylic. Coordinates from bregma were 3.5 mm posterior, 2.0 lateral, and 3.5 mm ventral. Tetrodes consisted of four HVF coated tungsten wires, 12 µm in diameter (California Fine Wire, Grover Beach, Calif.), twisted together. Recordings were performed while rats were awake and freely moving. Signals were filtered to a wideband (0.8 Hz-6 kHz) and amplified at a gain of 600× using a 31 channel wireless headstage (Triangle Biosystems, Durham, N.C.). These signals were then sampled at 40 kHz and stored on a computer for offline analysis. All further filtering was performed digitally with zero-phase filters (Matlab, filtfilt.m) to preserve timing between spikes and LFP. LFP data was obtained by lowpass filtering the raw signal at 500 Hz and downsampling to 2 kHz. To discriminate single units, the raw signal was highpass filtered at 400 Hz, and then 800 µs segments were extracted wherever negative peaks exceeded five times the standard deviation of peak heights. From these waveforms, the energy and the projections on first three principle component axes were used as features for automatic cluster cutting (MClust-3.5A, A. D. Redish et. al., University of Minnesota, and KlustaKwik-1.7, K. D. Harris, Rutgers University). Clusters were then manually adjusted on the basis of waveform shape, autocorrelation, and cross-correlation between clusters.

The results of the experiments are now described.

Both the PS-SFC and the FB-SFC estimation methods were applied to the simulated data sets and experimentally collected data. The simulated data sets were divided into categories based on the LFP model and the spike distribution model. The LFP was either modeled as a sine wave or an experimentally collected LPF signal filtered to a narrow band. Spikes were distributed by either a binomial distribution (correlated or not) or a Gaussian distribution around a preferred phase. Combinations of these categories gave four simulation platforms to assess these methods. In addition, bias correction was tested on a set of experimentally collected spikes and LFP signals. Estimation methods were judged based on bias, variance, and MSE criteria.

Sine Wave LFP with Binary Spike Distribution Model

Figure 7:
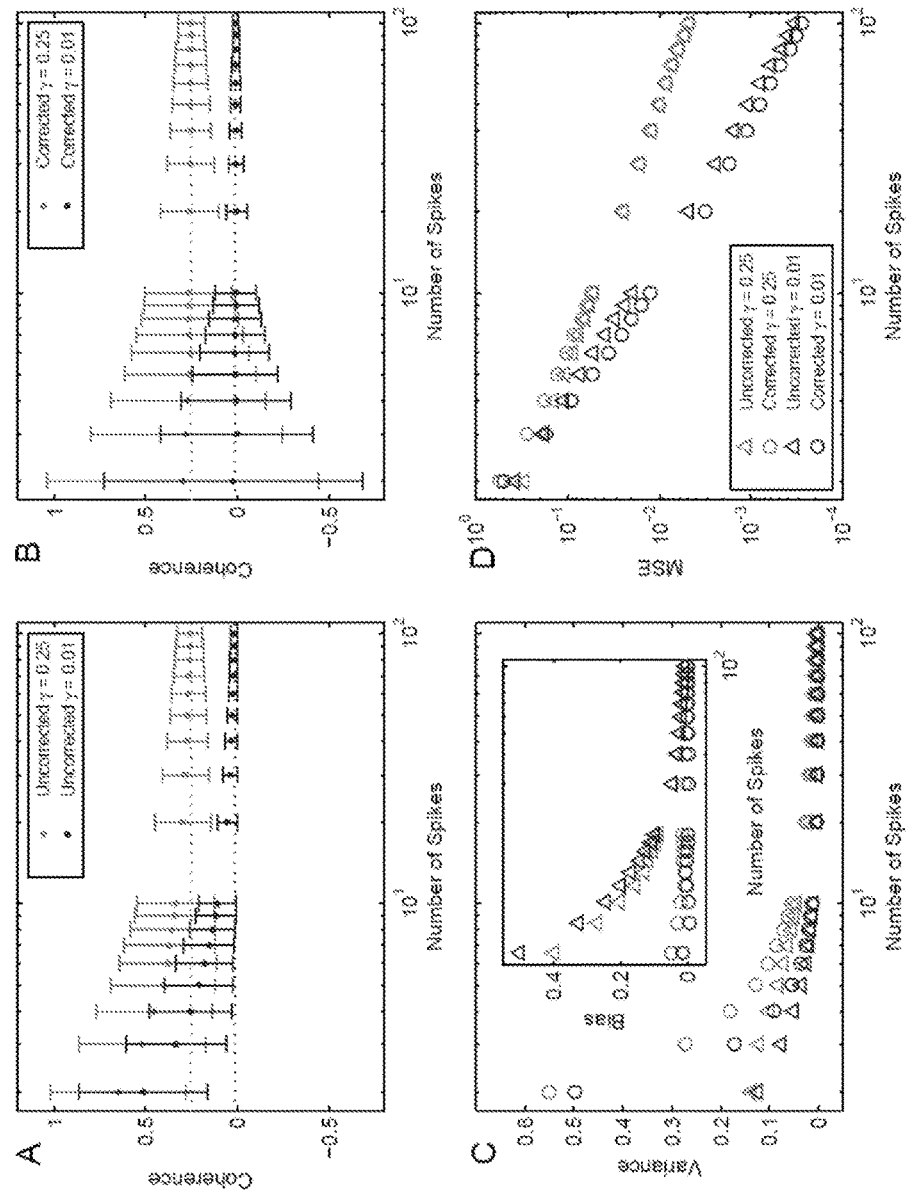
FIG. 7, comprising FIGS. 7A-7D, comprises a set of graphs illustrating the results of experiments using a sine wave LFP with binary distributed spikes. PS-SFC was estimated from simulated data for different numbers of spikes used in the STA. Spikes were placed with respect to the preferred phase of a sine wave by the binary distribution. Coherence strength was simulated at 0.25 (green) and 0.01 (blue). 1000 trials were performed.

When the PS-SFC and FB-SFC methods were applied to simulated data consisting of a sine wave with spikes placed by a binary distribution, the corrected coherence showed a reduction in bias but an increase in variance (FIG. 7). As expected, as the number of spikes increased, the mean uncorrected coherence estimate approached the asymptotic coherence (dotted line) and the variance of the estimate decreased (FIG. 7A). Since the LFP is represented as an ideal sine wave, there is no difference between the asymptotic coherence and the simulated coherence. When the correction was applied, the mean estimated coherence was consistent with the asymptotic coherence for all numbers of spikes, indicating a removal of bias. (FIG. 7B). The bias removal was confirmed in FIG. 7C (inset), but as a consequence of the correction, the variance of the estimate was increased. Since the SFC from one spike is trivially equal to 1, the bias will be greater for estimates of lower asymptotic coherence values. This effect is evident from the difference in bias between the two coherence strengths. As can be seen most clearly in the case of less than 10 spikes, the bias of the uncorrected estimator for $\gamma=0.25$ was lower than the bias for $\gamma=0.01$. In effect, the bias correction trades bias for variance. The overall direction of this trade, however, can be summarized by the mean squared error measurement (FIG. 7D). Importantly, the MSE was either reduced or unaffected in all cases except the case of both very few spikes and high coherence. For the majority of cases in this simulation, applying the correction reduced the bias of the coherence estimator and lowered the error, regardless of method. Because the difference between power and peak height is constant for a perfect sine wave, there was no difference between PS-SFC and FB-SFC estimates and therefore the FB-SFC results were not shown for this simulation. In the following, these conclusions were compared to a more realistic spike distribution model.

Sine Wave LFP with Gaussian Spike Distribution Model

Figure 8:
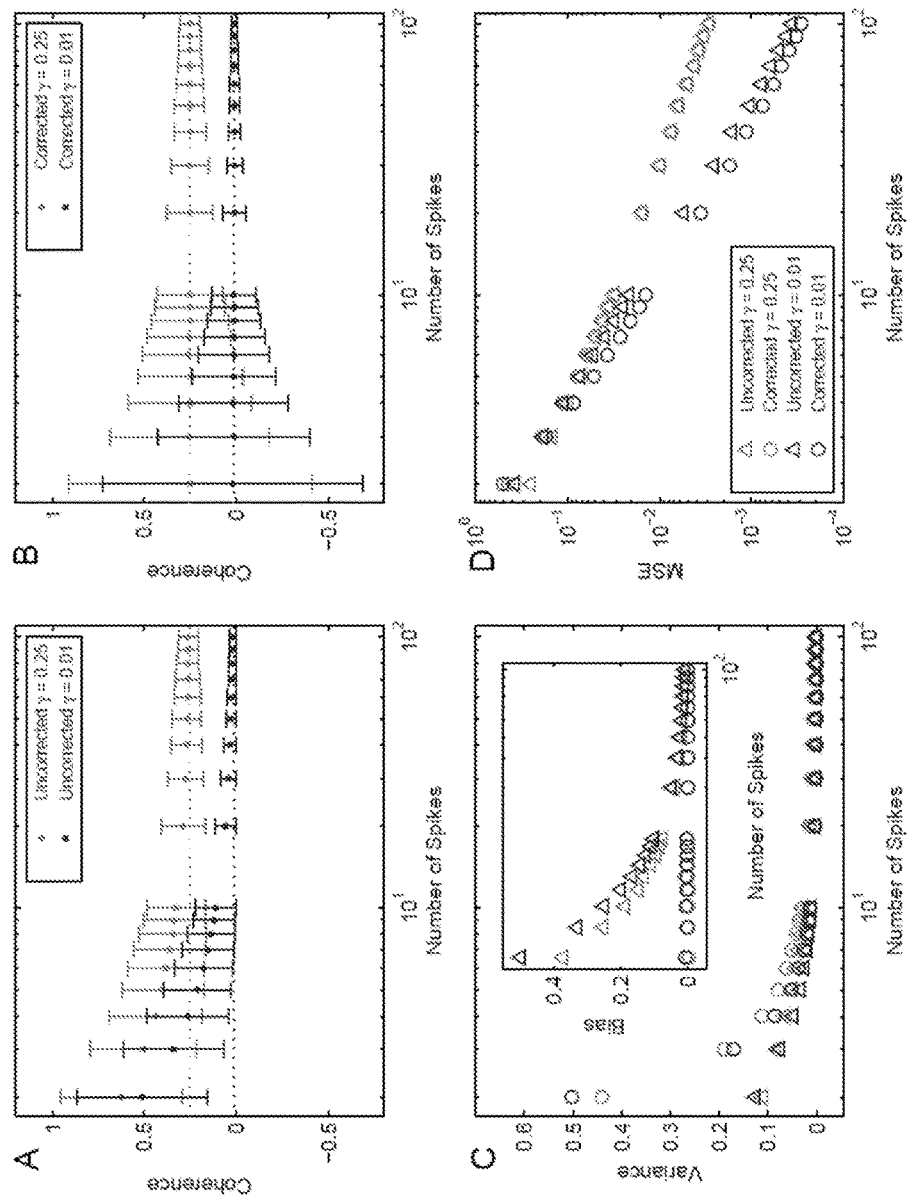
FIG. 8, comprising FIGS. 8A-8D, comprises a set of graphs illustrating the results of experiments using a sine wave LFP with Gaussian distributed spikes. PS-SFC was estimated from simulated data for different numbers of spikes in a manner similar to FIG. 7, but here the spikes were placed with respect to the preferred phase of a sine wave by the Gaussian distribution. Coherence strength=0.25 (green) and 0.01 (blue).

When a Gaussian distribution was used to place spikes with respect to a sine wave (FIG. 8), the SFC approached its asymptotic value with the same trend as the binary spike distribution for both the PS-SFC and FB-SFC methods. This is the trend predicted in the derivation of the bias correction. Again, the bias was decreased and the variance was increased when the correction was applied (FIG. 8C). The results are qualitatively similar to the case of binary spike distribution, with the exception that the variance in both uncorrected and corrected estimates was slightly reduced. Without wishing to be bound by any particular theory, this is likely due to the fact that a Gaussian distribution allows for finer gradients of coherence when there are fewer numbers of spikes. Changing the spike distribution also had no effect on the agreement between the asymptotic and simulated coherence. Finally the MSE was reduced except in the case of strong coherence and few spikes, similar to the binary distribution model (FIG. 8D). Similarly to the previous sine wave model, the methods produced identical estimates, and so only the PS-SFC results are shown.

Experimentally Collected LFP Models

Figure 9:
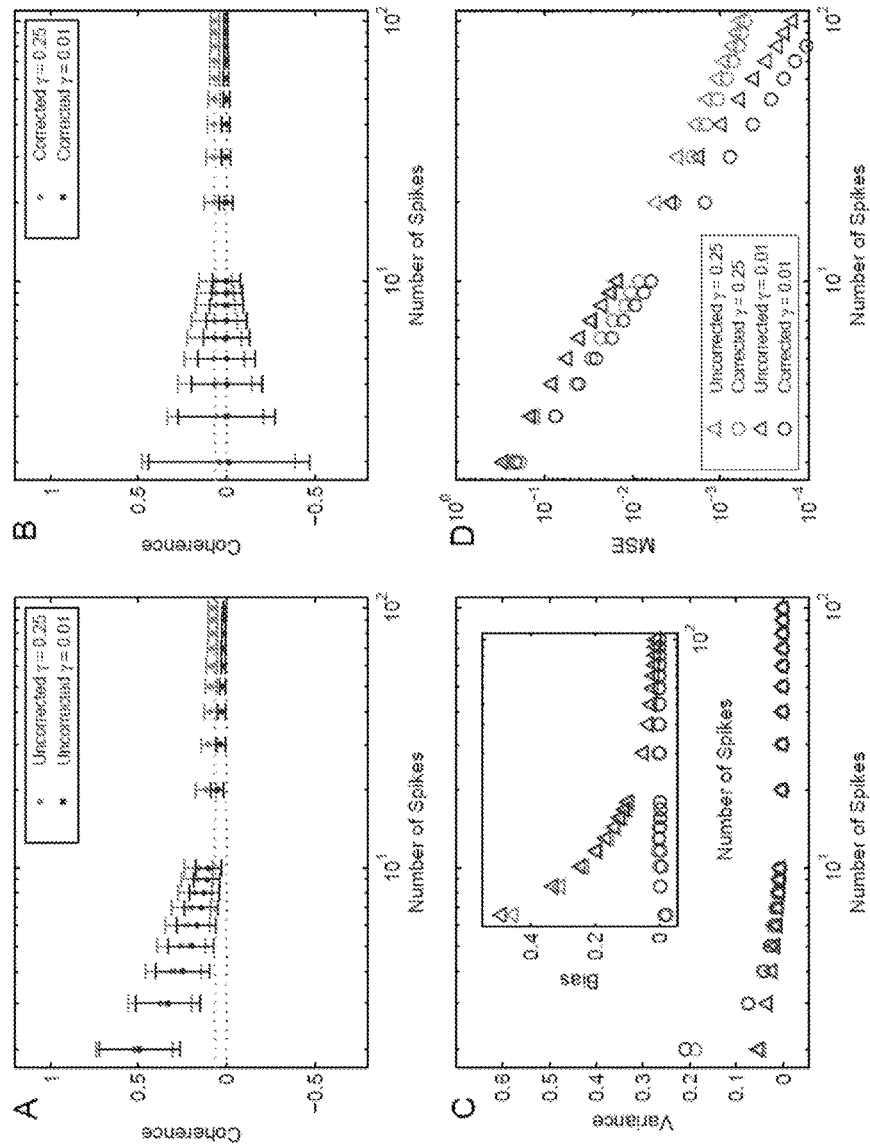
FIG. 9, comprising FIGS. 9A-9D, comprises a set of graphs illustrating the power spectrum SFC estimate using filtered LFP recorded from rat with Gaussian distributed spikes. PS-SFC was estimated from simulated data, as in FIG. 7 and FIG. 8 but spikes were placed with respect to the preferred phase of a filtered LFP signal by the Gaussian distribution. Coherence strength=0.25 (green) and 0.01 (blue).

In a more realistic simulation, replacing the sine wave with a real LFP signal, the MSE was reduced for all conditions simulated for the PS-SFC method (FIG. 9). Data shown are for a Gaussian spike distribution model, however results were quantitatively similar for the binary distribution. The first noteworthy feature is that the asymptotic coherence is lower than the simulated coherence. Due to this decrease, the mean values of coherence estimates for all numbers of spikes were reduced (FIG. 9A). In addition, for the same reason that there is greater bias for lower asymptotic coherence, the lower asymptotic coherence in this simulation increased the bias of the uncorrected estimator (FIG. 9C). The variance of uncorrected and corrected estimates was reduced compared to the sine wave models. Again, correcting the estimate reduced the MSE, but to an even greater degree than for sine wave models. This was due to two factors. An increase in the bias of the uncorrected estimator made a greater change after applying the correction, and the lower variance in the uncorrected estimate reduced the variance in the corrected estimate. For this more realistic simulation, the MSE was either reduced or unaffected under all simulated conditions after the correction was applied.

Figure 10:
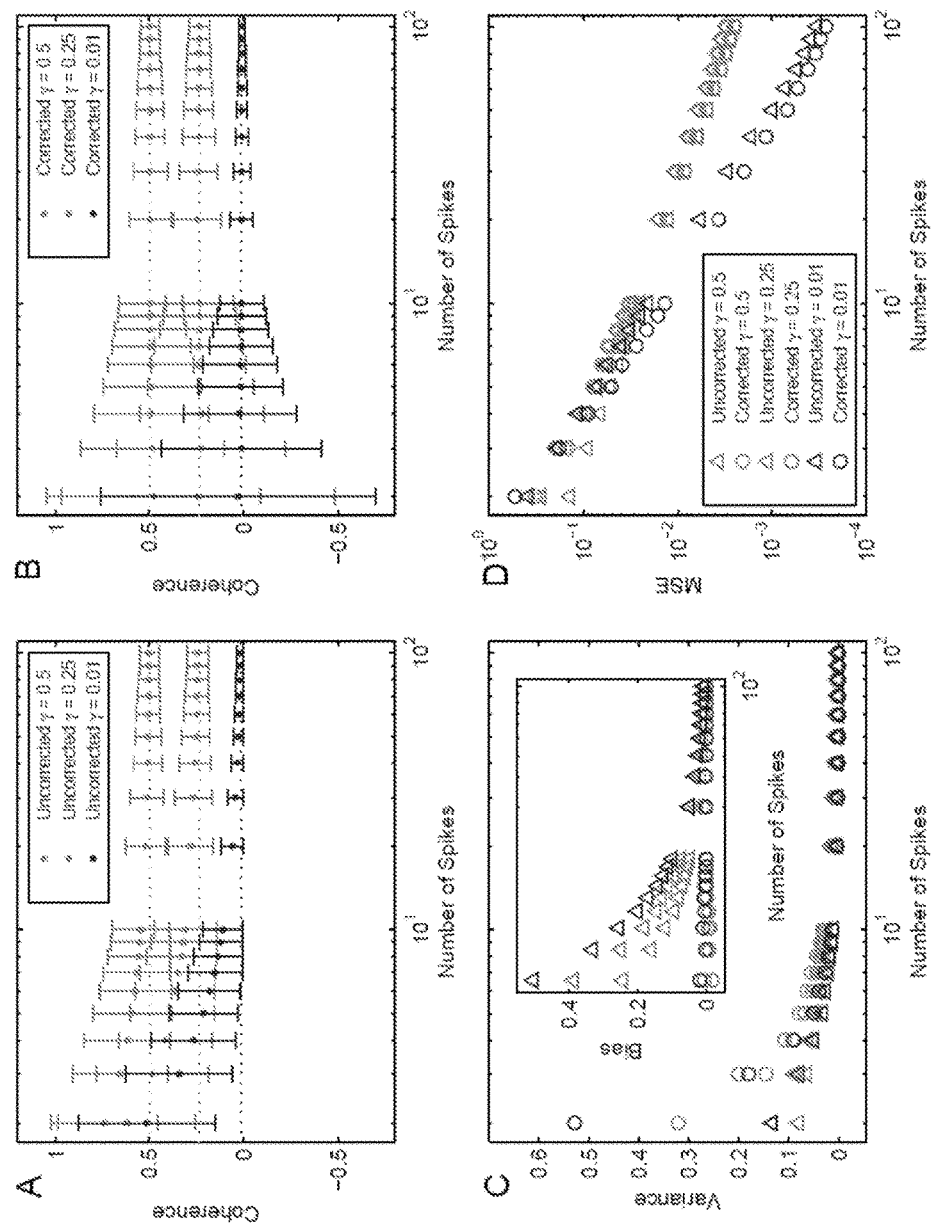
FIG. 10, comprising FIGS. 10A-10D, comprises a set of graphs illustrating Filter bank SFC using filtered LFP recorded from rat with Gaussian distributed spikes. FB-SFC estimated from simulated data with spikes placed with respect to the preferred phase of a filtered LFP signal by the Gaussian distribution. Coherence strength=0.5 (gold), 0.25 (green) and 0.01 (blue).

When the FB-SFC was applied to the real LFP simulation (FIG. 10), the asymptotic coherence was slightly less than the simulated coherence. This was similar to the PS-SFC result, except less pronounced. Apart from this aspect, there were no noticeable differences from when the FB-SFC was applied to the sine wave simulations. An additional case of very high coherence ($\gamma=0.5$) was added, in order to demonstrate that the bias is removed after correction for a wider range of coherence strengths. Because the bias is not as great for this highest level of coherence, correcting the bias increases MSE for less than 20 spikes. It should be noted that when applying either method to this model (Gaussian distributed spikes around the peaks of a well filtered, experimentally derived LFP), the asymptotic coherence did not equal the simulated coherence exactly. This is due to the way spike field coherence was modeled in the simulations. Coherence simulated by placing spikes in a random distribution around a phase of a filtered signal is more accurately reflected by the FB-SFC method than by the PS-SFC. This is not caused by a deficiency of the PS-SFC method, but because its output is influenced by other factors than the parameters used to simulated coherence.

Experimentally Collected Neural Data

Figure 11:
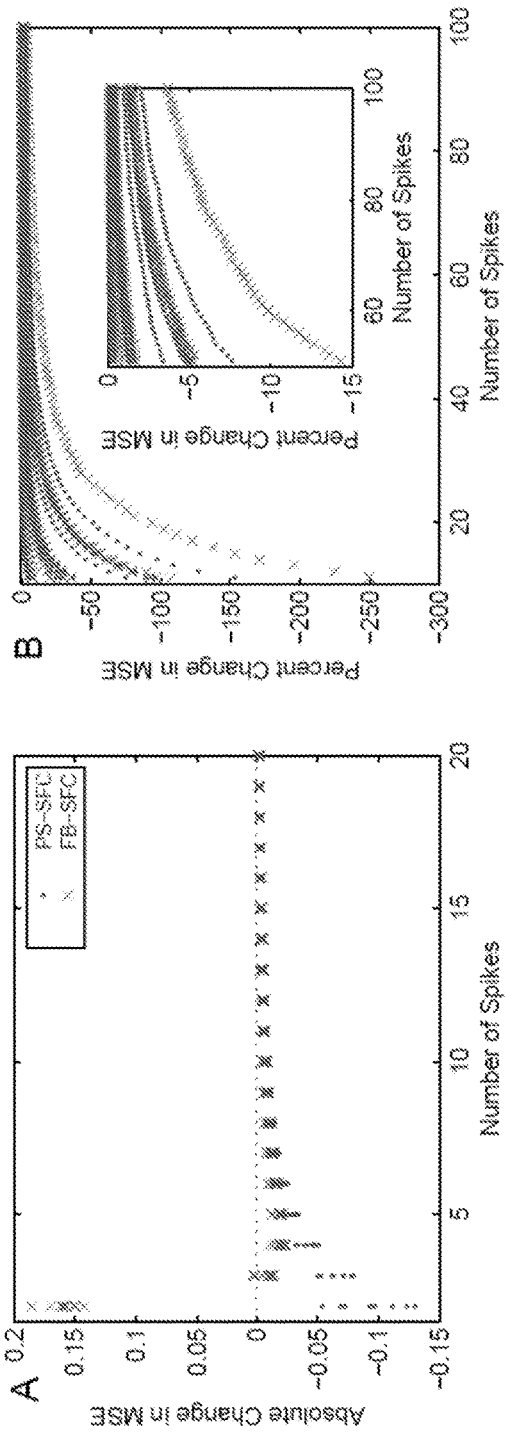
FIG. 11, comprising FIG. 11A and FIG. 11B, comprises a set of graphs depicting the results of experiments illustrating the change in the mean squared error of the SFC estimate after the bias correction was applied on data recorded from the hippocampus of rat. In each trial, coherence was estimated from up to 100 randomly chosen spikes from 9 neurons using the PS-SFC (black dots) and FB-SFC (red X's) methods. For each number of spikes used to calculate the coherence estimate, the change in MSE is given for each neuron (multiple red X's and black dots). 1000 trails were performed to obtain the MSE of the estimates before and after bias correction.

Finally, applying the bias correction to real data confirms the results seen in the simulations. Of the 54 neurons recorded from 3 rats, 9 neurons had enough spikes that the asymptotic coherence could be estimated with an uncertainty of less than 1%. SFC was then estimated again from a random subset of spikes from the same neurons. For each number of spikes, the squared error of the estimated coherence was found with respect to the asymptotic coherence. The mean squared error was then found by repeating this process over 1000 trials. Each estimate was also bias corrected, and the MSE of the bias corrected estimates were compared to the non-corrected estimates (FIG. 11). When the PS-SFC method was applied to the selected neural data, correcting the bias reduced the MSE for all numbers of spikes. However, when the FB-SFC method was used, MSE was reduced or unchanged for all numbers of spikes except very small numbers (n<3). The reason the bias correction is not as effective in reducing MSE for the FB-SFC method is because it has a higher variance for the estimation parameters chosen. As the number of spikes in the estimate increases, the bias correction does not have as large of an effect on each neuron and the MSE is not reduced as much. The reduction to the MSE for greater than 20 spikes appears small compared to the reduction for less than 10 spikes (FIG. 11A). However, normalizing these values to the asymptotic coherence gives a sense of the relative size of this error. The percent change reveals that the bias correction can still reduce the MSE by more than 5% of the asymptotic coherence value, even when 50 spikes are used (FIG. 11B inset).

Bias Correction

Through the course of applying the SFC estimation methods to simulated and experimental data, it was demonstrated that these methods overestimate the SFC, and the degree of this bias is a function of the number of spikes used and the asymptotic SFC. Of course, given enough data, many of the issues involved in coherence estimation are no longer of practical concern; including SFC bias. However, it cannot be assumed that this will always—or even often—be the case. It is when the limits of the estimator are pushed that the quality of estimation needs to be examined. There certainly exist experimental paradigms where it is difficult to collect large numbers of spikes. One example is if SFC is to be estimated over short time intervals. This could occur if one is studying coherence during transient events (i.e. stimuli, ripples, or epileptic seizures), or if coherence is suspected of changing rapidly with time. Compounding the problem are neurons which fire with a very low rate. Pyramidal cells with a firing rate of less than 1 Hz are not uncommon in the hippocampus. In cases such as these, the bias has an appreciable effect on the estimate.

The proposed bias correction has been shown to have two major effects on the quality of the coherence estimate. In general, it reduces bias while adding variance to the estimate. This can result in either an increase or decrease in the MSE, depending on the asymptotic coherence and the number of spikes in the STA. For the more realistic simulated models and the experimental data, the results from the conditions tested showed that the MSE is usually either reduced or unaffected, except in the case of high coherence ($\gamma > 0.25$) and low numbers of spikes ($n < 4$) for the FB-SFC method. It was previously found that coherence levels are typically lower than this in neuronal data, even for well synchronized cases (Foffani, et al., 2007, Neuron 55:930-941; Fries, et al., 1997, Proc Natl Acad Sci USA. 94:12699-12704). Therefore it seems unlikely that the correction would increase the error in estimation.

The bias correction had the greatest effect when the number of spikes was less than 100, and beyond this its effect was less pronounced. However, this does not mean the bias correction should not be used in cases of greater than 100 spikes because when asymptotic coherence is low, results may still be biased. Consider a comparison between two conditions, both of zero actual coherence. In either condition, the uncorrected estimate will have an expected value of $1/n$. If in one condition, 200 spikes are available in the observation window, the expected estimated coherence will be 0.005. For some this might be an acceptable error. However if the other condition only has 100 spikes available in the observation window, the expected value of the uncorrected estimate will be 0.01. The result is that one estimate is twice as great as the other, even though the coherence is the same in both cases. Since the bias correction does not increase the MSE for cases of large numbers of spikes, it can be beneficial even for cases of greater than 100 spikes.

Of course, other methods of estimating unbiased SFC-related measures have been proposed. Since the degree of bias depends on the number of spikes, the simplest approach is to fix the number of spikes used for each estimate. The obvious shortcoming of this technique is that the number of spikes in each estimate must be limited to the estimate with the fewest spikes. This means data must be disregarded from the analysis, and that some estimates will have more variance than they would have had with all available spikes. Bootstrapping techniques (Vinck et al., 2010, J Neurosci, 30(4): 1250-1257) can address both of these problems, but there are still issues with dependence on spike distribution, dependence on parameter choice, and computational feasibility. One recent measure (Vinck et al., 2010, Neuroimage, 51(1): 112-122) called the pairwise phase consistency (PPC) addresses the bias problem by effectively fixing the number of spikes at 2, and averaging over the quantities calculated for all possible pairs of spikes in the sample. The expected value of the PPC was shown to be equivalent to the asymptotic limit ($n \to \infty$) of a widely used and biased measure, the phase locking value. While this is a well formulated solution to the bias problem of the phase locking value, it is unknown whether it can be applied to other SFC-related measures. It would be interesting to see if a technique similar to the PPC can be developed for unbiased estimation of PS-SFC and FB-SFC, and how it would compare to the bias correction described herein.

Asymptotic and Simulated Coherence of PS-SFC and FB-SFC

For some simulations, the FB-SFC and PS-SFC methods had asymptotic coherences values different from the simulated coherence. On the one hand, using a sine wave as a model of LFP, the asymptotic coherence for both estimation methods was equal to the simulated coherence. On the other hand, when using LFP and simulated spikes, the asymptotic coherences were different from each other and different from the simulated coherence. Finally, when applied to real data, there were differences in the asymptotic coherence estimates between the two methods as well. These discrepancies are largely due to subtle differences in the quantities these two methods measure, and to how those quantities change when the data is no longer ideal. The FB-SFC measures the peak amplitude of an STA constructed from a filtered signal, and the PS-SFC measures the power spectrum of the unfiltered STA. Outside of an ideal sine wave, these two quantities, although similar, are not necessarily equivalent. Therefore, there will be a predisposed tendency for these two methods to produce different estimates. Additionally, it was observed that the FB-SFC asymptotic coherence was much closer to the simulated coherence than the PS-SFC. This is most likely because in this simulated data, the spikes were placed with respect to the phase of a filtered LFP signal, which is the same signal the STA is constructed from in the FB-SFC method. Essentially, the FB-SFC has the advantage of being able to more directly reflect the simulation parameters that control coherence strength. While not wishing to be bound by any particular theory, had the coherence been simulated in a different way, this probably would not be the case.

Factors that Influence SFC Estimation

Figure 12:
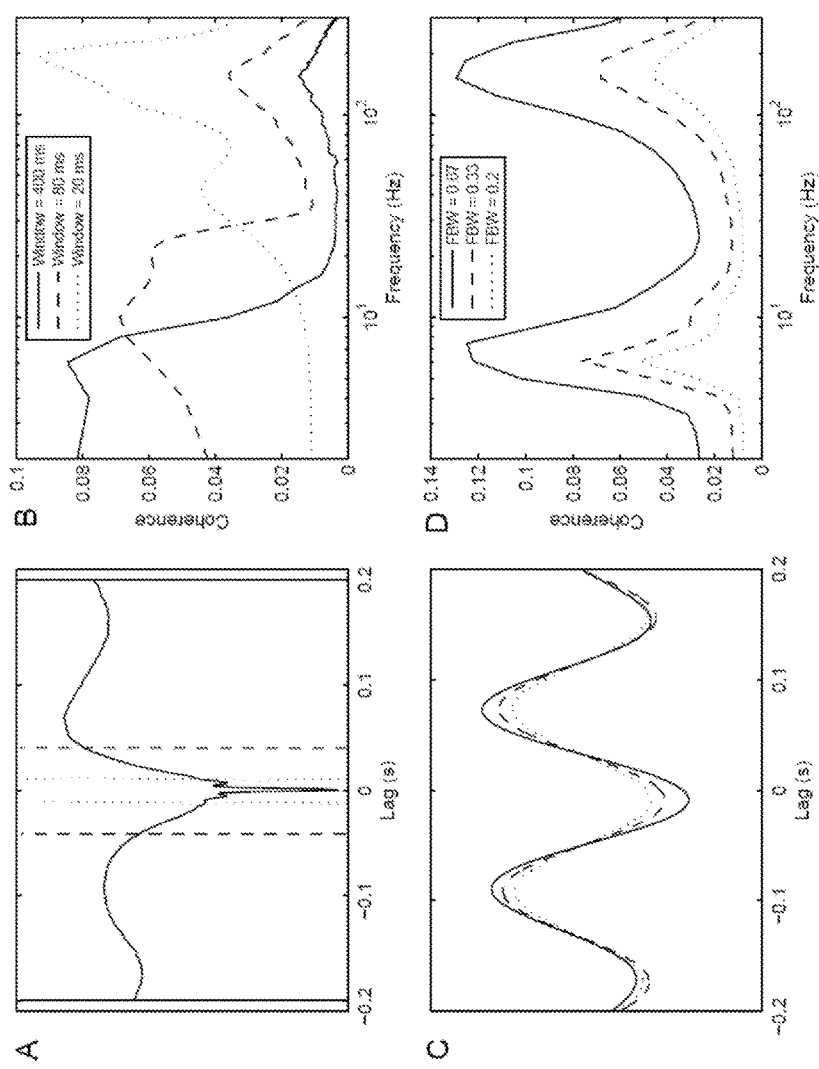
FIG. 12, comprising FIGS. 12A-12D, comprises a set of graphs illustrating how the parameters of the estimation methods affect the coherence spectrum. As depicted in FIG. 12A, an STA was constructed from all available spikes (n=58035) from one neuron recorded in vivo. SFC was calculated by using PS-SFC with 3 different window sizes: 400 ms (solid line), 80 ms (dashed line), and 20 ms (dotted line). The power spectrum estimation in this method was performed in the same way as the simulated data.

As with any estimation method, it is important to be aware of which controllable factors influence the end result in addition to the parameter being estimated. It has been demonstrated that the number of spikes used to estimate the coherence causes a bias in this estimate, but even if a very large number of spikes are used, other parameters in the estimation process can still cause different kinds of bias. For the PS-SFC method, the size and shape of the STA window can affect the estimate. With an ideal sine wave, if spikes occur at the peak of the oscillation, they are just as correlated with a peak that happened many cycles ago or many cycles in the future. This will cause an STA created from sine waves to have the same average amplitude at any time lag from the center (spike). Since in real systems spikes are coherent with oscillations that are not perfectly periodic, there is an attenuation of STA power with increasing time lag from the center. This is to be expected as there is no reason a spike should be correlated with a cycle of an oscillation that happened far away in time. This general phenomenon, which occurs in many biological systems, is a consequence of the mixing condition (Brillinger, D. R. (1981). Time Series—Data Analysis and Theory Expanded. E. A. Robinson, ed. (San Francisco: Holden-Day, Inc.); Rosenblatt, 1956, Proc Natl Acad Sci USA 42:43-47). Therefore, the closest estimate of the coherence is at the center of the STA. The practical implication is that the STA window in which the PS-SFC is calculated will influence the estimated coherence. Compounding this issue is the fact that the degree of power attenuation is frequency dependent. Coherent high frequency oscillations attenuate within much shorter time windows of the STA center than do low frequency oscillations (FIG. 12A). It follows that for each frequency there is an optimal time window with which to estimate the STA power in that frequency. The inverse of this statement is that the power spectrum for a given STA window will automatically enhance a certain frequency range while depressing surrounding frequencies (FIG. 12B). Furthermore, this problem is not solved by the multitaper technique with discrete prolate spheroidal sequences since additional tapers do not emphasize the exact center of the STA. Therefore, the STA window size should be chosen to optimally estimate a specific frequency band when using the PS-SFC method. Comparisons between different frequency bands should require different STA windows.

Instead of using the entire STA window to estimate coherence, the FB-SFC method estimates it from the peak amplitude at the center of the STA. Since this estimate comes from a single point instead of a range, this method may produce more uncertainty in the estimate. This accounts for the increased variance from the FB-SFC method compared to PS-SFC. However, this feature also allows the filter bank method to estimate the coherence fairly between all frequency bands since it is not dependent on the STA window (FIG. 12D). The major factor that influences the estimate of coherence in this case is the fractional bandwidth of the set of filters. This is defined as the bandwidth of a filter divided by the central frequency. The FB-SFC method relies on the peak amplitude of the filtered signal being proportional to the power. This is true of a pure sine wave, but this proportionality breaks down as the bandwidth of the signal increases. Therefore, larger fractional bandwidths will increase the overall value of coherence across the spectrum, while decreasing the frequency resolution. Although there is a small difference in the ratio of the spectral peaks at 6 Hz and at 150 Hz as the fractional bandwidth increases, this is attributed to a loss of frequency resolution. In fact the peak at 6 Hz is noticeably wider and less well resolved at the highest fractional bandwidth (0.67) than at the other fractional bandwidths. This is the fractional bandwidth that results when each band is double the bandwidth of the last band (i.e. 2-4 Hz, 4-8 Hz, 8-16 Hz, etc.) and is a common approximation of the conventional rhythms of the brain. However, when examining the broad spectrum, it is usually better to have a higher frequency resolution since coherence can sometimes occur in narrow bands. Therefore, a fractional bandwidth of less than 0.33 is a better choice.

Appropriate Application of Methods

Results presented herein suggest that the estimation methods examined here are influenced by factors other than the actual coherence. The major factor that is common to both methods is the number of spikes, which causes a positive bias in the SFC estimate. In addition, each method has controllable parameters that can affect the estimate. With this in mind, it is important to know the experimental circumstances under which these methods can be appropriately applied.

Probably the most common experimental paradigm is to compare a single neuron's SFC in a specific frequency band between two conditions. In this case, the minimum comparison needed is a single SFC estimate for each condition. This type of comparison could potentially be made by using a specialized statistical test, such as an adapted version of the nonparametric test for LFP-LFP coherence (Maris, et al., 2007, J Neurosci Methods 163:161-175). However, it may be desirable to estimate a population-average SFC instead of single neuron SFC, and even necessary if the same neurons cannot be recorded in both conditions. Pooling trials (spike-centered LFP segments) across neurons as a possible application of the nonparametric test would be inappropriate due to differing preferred phases and firing rates of the neurons. A more logical approach is to consider the coherence values estimated from individual neurons as observations, and the comparison is between a sample of observations in one condition and a sample in the other condition. The problem is that when these observations are biased estimates, no statistical test can separate the effect of the number of spikes from the coherence. The bias must be removed before this type of comparison can be made, and this is solved by the bias correction.

Sometimes it is unknown which oscillation frequencies a neuron will be coherent with a priori, and an examination of SFC across a broad spectrum is required. Even if statistical comparisons between frequency bands are not experimentally necessary, it is useful to know at what frequencies coherence is actually occurring, and this can only be accomplished by eliminating the frequency-dependent bias in the estimate. The PS-SFC method, if used incorrectly, suffers from this type of bias as discussed in the previous section. Therefore, a fair comparison of frequency bands requires recalculating the estimate for multiple STA window sizes. Alternatively, the FB-SFC method can be used for this type of comparison. Since this method does not depend on the STA window size, coherence estimates can be made fairly across the entire spectrum.

It is important to remember that in real conditions the SFC can only be estimated, and there is always uncertainty in this estimate. A very large number of spikes will usually give an estimate with little bias, but this type of data set is not always available. In addition, it is difficult to tell just how many spikes are needed when coherence is low. The proposed bias correction addresses these problems by severing the estimate's dependence on the number of spikes.

Example 3

The Role of Interneuron Synchrony in the Transition to Spontaneous Seizures

The role of inhibitory neuronal activity in the transition to seizure has become controversial. The activity of populations of putative hippocampal interneurons and pyramidal cells during the transition to spontaneous seizures in the pilocarpine rat model is examined herein. Beginning minutes before seizure, subpopulations of interneurons displayed a sequence of synchronous behaviors, including synchrony with local field oscillations at theta, gamma, and finally ictal spiking frequencies, and increased firing rate seconds before ictal spiking onset. Conversely, pyramidal cells did not exhibit increased synchrony or firing rate until after ictal spiking had begun. These data help clarify inconsistencies between in vitro studies demonstrating interneuron activation at the transition to seizure, and human studies demonstrating heterogeneous neuronal firing at this time. It is concluded that the transition to spontaneous seizure in this network is not mediated by homogeneous hyper-excitation, but rather by sequential stages of distinct synchronous inhibition.

A lack of understanding of the network mechanisms underlying the transition of epileptic tissue from an interictal state to an ictal state has hindered the development of effective therapies for epilepsy. The prevailing theory underlying the initiation and spread of seizures within the brain has focused on the imbalance between excitation and inhibition in favor of excitation (Ayala, et al., 1970, J Neurophysiol. 33:73-85; Mathern, et al., 1993, Electroencephalogr Clin Neurophysiol 87:326-339; Engel, 1990, Electroencephalogr Clin Neurophysiol 76:296-316). The earliest evidence for this theory was found in intracellular recordings in the cat during seizure activity produced by focal application of penicillin (Matsumoto and Marsan, 1964, Exp Neurol 9:305-326; Dichter and Spencer, 1969, J Neurophysiol 32:663-87). Subsequent studies in human epileptic patients also supported this idea by linking the degree of increased multiunit activity in the temporal lobe at seizure onset to the severity of seizures (Babb and Crandall, 1976, Electroencephalogr Clin Neurophysiol 40:225-243; Babb, et al., 1987, Electroencephalogr Clin Neurophysiol 66:467-482), although the type of these neurons was not identified.

More recently, an alternative theory based on in vitro studies proposed that activation of hippocampal interneuron networks is responsible for seizure initiation (Fujiwara-Tsukamoto, et al., 2010, J Neurosci 30:13679-13689; Velazquez and Carlen, 1999, Eur J Neurosci 11:4110-4118; Ziburkus, et al., 2006, J Neurophysiol 95:3948-3954). For example, Ziburkus et al. showed that interneuron activity was maximal just before the onset of fast positive-going ictal spikes in the local field of hippocampal slices. Induced seizures have also been studied in the intact brain preparation and here too, a role for interneuron activity in the generation of seizure-like activity prior to the onset of sustained ictal spiking was demonstrated (Timofeev et al., 2002, Neuroscience 114:1115-1132; Bragin et al., 1997, Neuroscience 76:1187-1203; Gnatkovsky, et al., 2008, Ann Neurol 64:674-686). These data suggest a role for inhibitory interneurons in the generation of seizures and it is herein examined whether excessive and/or hypersynchronous interneuron activity may be responsible for the initiation of spontaneous seizures in human temporal lobe epilepsy. To test this idea, the behavior of interneurons during the transition to seizure needs to be examined in an awake animal model with seizures that are not directly induced, but occur spontaneously.

The pilocarpine epilepsy model is widely used as a model of human temporal lobe epilepsy because it reproduces many of its features including spontaneous seizures, mossy fiber sprouting, selective interneuron loss, and poor control of seizures by anti-epileptic drugs (Curia, et al., 2008, J Neurosci Methods 172:143-157). Bower et al. completed the first study which used this model to record multiple single granule cells from the dentate gyrus, and showed that the variability of firing rates between cells increased in the minutes before spontaneous seizure (Bower and Buckmaster, 2008, J Neurophysiol. 99:2431-2442). This result was recently supported by a finding of heterogeneous firing patterns in the neocortex of human epileptic patients before and during spontaneous seizures (Truccolo, et al., 2011, Nat Neurosci 14:635-641), similarly contesting the idea that seizure onset is simply characterized by homogeneous hyper-excitation of populations of neurons. However, these studies did not specifically address the role of interneurons in the transition of the hippocampal network from interictal activity to ictal activity.

To overcome this, the present study included recordings from large numbers of neurons within the CA3 hippocampus of freely moving pilocarpine-treated rats exhibiting chronic recurrent spontaneous seizures, and the sorting of cells into putative inhibitory (interneurons) or excitatory (pyramidal cells) groups. Changes in neuronal activity from these distinct populations were examined as the network transitioned from interictal to ictal activity as evidenced from local field potential (LFP). Results presented herein show that beginning minutes before ictal spiking, interneurons undergo changes in synchrony, becoming more correlated with each other and more coherent with theta oscillations in the LFP. In the seconds before ictal spiking begins, interneurons become coherent with gamma LFP oscillations and display increased firing rates not seen during the prior interictal state. Finally, the onset of sustained ictal spiking is characterized by a further change in synchrony, where interneurons become highly coherent with the frequency of ictal spiking, and more correlated with each other. Only after these synchronous activities occur, and ictal spiking has begun, do pyramidal cells begin to show increases in firing rate and coherence with ictal spikes. These results support the view that rather than runaway excitation or deficient inhibition, synchronous interneuron activity plays a primary role in the transition from interictal to ictal states.

The materials and methods employed in these experiments are now described.

Epilepsy Model

Long Evans rats (225-275 g) were initially given scopolamine methyl nitrate (1 mg/kg, i.m.) to reduce cholinergic effects, and supplementary doses were given at 2 hour intervals. Status epilepticus was induced in by a systemic injection of pilocarpine (400 mg/kg, i.p.). Rats that exhibited status (~40%) were clearly distinguished by nearly continuous myoclonic seizures which ranked 3-5 on the Racine scale. Status was allowed to persist for 2 hours before administration of diazepam and pentobarbital to halt the seizures. Rats were given Lactated Ringer's solution and kept on a heating pad until they recovered. Beginning 3 weeks after pilocarpine injection, rats that experienced status were monitored for spontaneous seizures by recording video for 8 hours per day.

Microdrive Assembly and Surgery

Approximately 1 month after pilocarpine injection, rats that displayed spontaneous seizures were chronically implanted with drivable tetrodes. Tetrodes were made from 4 HFV-coated tungsten wires (12.7 μm), twisted and fused together. 7 tetrodes were used for recording single units and a separate electrode was used for recording LFP. The LFP electrode was identical to the other tetrodes, except all 4 wires were connected to the same channel. The separate LFP electrode allowed for a nearby recording of the local field without contamination from unit activity, which is important for high frequency coherence measurements between action potentials (AP) and LFP. Tetrodes were loaded into a microdrive (Neuralynx 9-drive) and arranged so that they formed a circle (1 mm diameter) around the LFP electrode. Electroplating was considered unnecessary since the final impedance of wires were 200-500 kΩ. For surgery, rats were given scopolamine (1 mg/kg, i.m.), anesthetized with isoflurane, and intubated for sustained isoflurane anesthesia (1.5-2.5%) in a stereotaxic apparatus. The microdrive was implanted above the dorsal hippocampus (AP=−3.25, ML=−3.0), and tetrodes extended to a depth of 2 mm ventral to bregma. The ground wire for all tetrodes was connected to a skull screw placed at AP=5.0, ML=1.0. After implantation, the microdrive was sealed in place with dental acrylic. All procedures were approved by the Institutional Animal Care and Use Committee and followed National Institute of Health guidelines.

Data Collection

Rats were given at least 3 days to recover from surgery before driving the tetrodes. Tetrodes were advanced slowly (500 µm per day) until they reached the pyramidal cell layer of CA3 at approximately 3.8 mm ventral to bregma. This position was confirmed by the appearance of large amplitude unit APs. Once the tetrodes were positioned in the pyramidal layer, rats were given at least 1 day for waveforms to stabilize before recordings commenced. Repeated recordings were taken, each being 24-48 hours in duration, with 48 hours between each recording. This was facilitated by the use of a wireless headstage amplifier (Triangle Biosystems 31-channel, ×600 gain) powered by an external battery attached to a rat jacket. Wideband (0.8 Hz-6.5 kHz) neural signals were broadcast to a receiver, acquired at 40 kHz sampling rate, and written to a hard drive. After each recording, tetrodes were adjusted slightly to obtain new units. However, no recording was ever taken less than 24 hours after moving the tetrodes. For each seizure that occurred, the data beginning 1 hour before and 1 minute after seizure (a seizure period) was used for further analysis.

Signal Processing and Single Unit Discrimination

Figure 13:
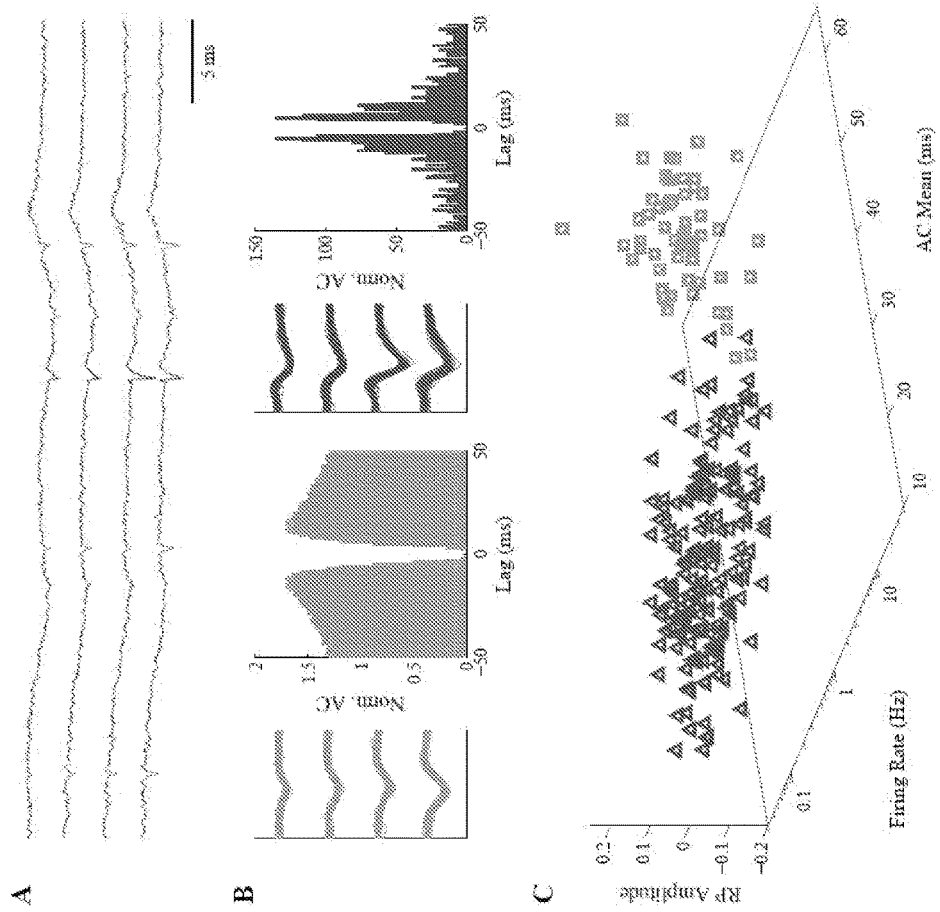
FIG. 13, comprising FIGS. 13A-13C, comprises a set of graphs illustrating the discrimination of interneurons and pyramidal cells.

Signals were digitally filtered offline using zero-phase filters (MATLAB filtfilt.m). LFP was obtained by low-pass filtering at 600 Hz and downsampling to 4 kHz, while unit activity was high-pass filtered at 350 Hz. An amplitude threshold was applied to the high frequency unit signals at −5 times the standard deviation of the signal. Waveforms that exceeded this threshold were collected by custom Matlab scripts, aligning all waveforms to the time of the negative peak. For each threshold crossing, waveforms from all four channels of the tetrode were concatenated into one long waveform. From the collection of all the concatenated waveforms in the seizure period, the first 16 principal components projections were obtained and used as features to cluster the data in high dimensional space via an unsupervised clustering algorithm (Klustakwik 1.7, Ken Harris, Rutgers University). Final selection of valid single unit clusters was done manually according to waveform shape and spike time autocorrelation, with an emphasis on the refractory period. Clusters that appeared to belong to the same single unit were merged according to the criteria of similar waveform shape, relative amplitude between the four channels, cross-correlation, and the merged autocorrelation function. Once all single units were identified, an additional discrimination was performed to generally categorize units as putative pyramidal cells or interneurons. These cell types could be separated on the basis of firing rate, autocorrelation, and waveform shape (FIG. 13). A minority of single units that did not fit well into these two categories was excluded from further analysis.

Finding the Onset of Sustained Ictal Spiking

To find the ictal spiking onset, the LFP was first low-pass filtered at 50 Hz so that the peaks of ictal spikes could be easily (computationally) identified. As a first pass, the transition point from non-spiking LFP to ictal spiking LFP was selected by eye. The moment 5 seconds after the transition was used as a starting point for a reverse sliding window of 1 second duration. This window moved backward in time by 100 ms increments, counting the number of LFP spikes that exceeded a significance threshold. The threshold was set at the mean±4 times the standard deviation of the LFP amplitude, obtained in the two minutes before seizure. The greater limit of the first 1 second interval in which no LFP spikes crossed threshold was considered the onset of ictal spiking.

LFP Power Spectrogram

The LFP power spectrum was estimated in 2-second bins over the entire seizure period. Power was estimated using a filter bank method so that the frequencies corresponded exactly to SFC frequencies (see Spike Field Coherence). The wideband LFP signal was filtered by a set of 35 bandpass filters where the $n^{th}$ band had a central frequency equal to $1.2^{n-1}$. The frequency limits of each band were 0.8 and 1.2 times the central frequency, giving a fractional bandwidth equal to 0.4 and approximately a half bandwidth of overlap between consecutive frequency bands. Filtering was performed using zero-phase (filtfilt.m) FIR filters (order=40000/central frequency) with Hamming windows implemented in MATLAB. After filtering, the power in each 2-second bin was estimated by calculating the variances of the filtered signals within the bin, then each bin was normalized by dividing by the summed power over all bands.

Single Unit Firing Rate

Population firing rates were measured by counting the number of APs for each neuron in 2 s bins, beginning 1 hour before seizure and ending 1 minute after seizure (the seizure period) to create a firing rate histogram. Population PETHs were then constructed by averaging histograms of all interneurons or pyramidal cells, aligned to the ictal spiking onset. The PETH values were normally distributed in both cases (Lilliefors test, $p<0.05$), and significance thresholds were set at ±3 SD from the mean in the background (−1 hr to −10 min).

To find the fraction of neurons with increased firing rate in a given window, times (2 s bins) of increased firing were detected for each neuron over the entire seizure period. A given bin was considered to be a time of increased firing if it exceeded the mean of the bins in the previous 2 minutes by 4 SD ($p<0.001$, assuming Poissonian firing statistics). This 60-bin trailing window allowed sensitive detection of transient ($<10$ s) increases in firing rate, while ignoring slow ($>10$ min) modulations of firing rate.

Activation windows were defined with respect to the ictal spiking onset as −6 to 4 s for interneurons and 4 to 14 s for pyramidal cells, based on the population PETH results. The fraction of all neurons of a given type with a detected firing rate increase within these respective activation windows was measured. The fraction of neurons with firing rate increases were similarly measured for a series of equivalent duration, non-overlapping background windows (−1 hr to −10 min, 300 background windows). Since the sampling distribution of a proportion is a binomial distribution, a significant increase from background was defined the fraction of neurons (x/n) at which the cumulative binomial distribution $B(x; n, \mu)$ was greater than 0.99 ($p<0.01$). The probability $\mu$ of a neuron having an increased firing rate in a given window was obtained from the mean fraction of neurons over all background windows.

For each neuron with an increased firing rate in the activation window, the duration (number of consecutive bins) and magnitude (max bin) of the firing rate increase were compared to the average of these quantities from background windows with a detected increase in firing rate. These differences were tested for significance for each cell type by a sign test (p<0.05).

Spike Field Coherence

Coherence between APs and LFP oscillations was measured by utilizing a filter bank technique (Fries, et al., 2001, Science 291:1560-1563; Grasse and Moxon, 2010, J Neurophysiol 104:548-558). In short, segments of the filtered LFP that occurred around the time of each AP were averaged to create a spike-triggered average. The central peak amplitude of this average LFP was normalized to the average peak amplitude from all LFP segments to obtain the biased (by number of APs) estimate of coherence in given band.

Coherence was examined as a time-varying process, by repeating the estimation every 100 ms over the seizure period. The estimate of coherence for a neuron at a given point in time was obtained from the previous n APs and the simultaneous LFP. For each neuron, n was fixed so that the bias would be equal at each point in time. This number (n) was at least 5, but otherwise equal to twice the neuron's average firing rate over the seizure period, rounded to the nearest integer. Repeating this procedure for each frequency band provided a time-frequency coherence spectrogram for each neuron.

Population coherence spectrograms were created by aligning all individual interneuron or pyramidal cell spectrograms to the ictal spiking onset and averaging within the cell type. Oscillation windows (bounded in time and frequency) were defined and used to measure the fraction of neurons with a detected increase in coherence, similar to the single neuron firing rate analysis. Since coherence values did not consistently fit any common distribution, times of increase were detected non-parametrically. From 1 hour before ictal spiking onset through the last time in the oscillation window of interest, all coherence values were rank-ordered and times where the coherence was above the 99.9% percentile were considered times of increase. The fraction of neurons with a detected increase in the time-frequency bounds of an oscillation window was statistically compared to equivalent-duration-and-identical-frequency background windows (−1 hr to −10 min) by the same method as for single unit firing rate (p<0.01).

Cross-Correlation

Two measures of cross-correlation between AP trains of simultaneously recorded neurons were used in this analysis. The fraction of correlated neuron pairs (of a given pair type) were measured by constructing a cross-correlogram (bin size=10 ms) for each pair using the APs that occurred within a given time window. To determine if the pair had a significant correlation, first an expected value of the correlation was obtained using the firing rates of both neurons within the window (Eggermont, 1992, J Neurophysiol 68:1216-1228). If the peak of the correleogram (zero-lag bin) exceeded this expected value by 3 SD, the pair was considered to have a significant correlation. A population cross-correlogram was created by pooling (summing) all cross-correlograms for a given pair type, and normalizing to the total expected number of APs. The fraction of correlated pairs and the peak of the population cross-correlogram were measured within activation or oscillation windows and statistically compared to background windows in a manner similar to that used for single unit firing rate and coherence analysis (p<0.01). The only difference was that the peaks of background population cross-correlograms were normally distributed (Lilliefors test, p<0.05), so significance was set at 3 SD outside the mean (p<0.0027).

The results of the experiments are now described.

Arrays of tetrodes were used to record extracellular single units and LFP from the dorsal CA3 hippocampus of spontaneously seizing pilocarpine-treated rats. A wireless recording system (Triangle Biosystems, Durham N.C.) was employed to record from awake, freely moving animals during 24-48 hour continuous periods (average of 5 per rat) in order to catch spontaneous seizures and ensure sufficient interictal data for a complete analysis. Seizure frequency was variable and seizures sometimes occurred in clusters, but overall rats averaged 0.85±2.9 seizures per day. To minimize potential baseline contamination from post-seizure effects, seizures were excluded from analysis if another seizure occurred less than 2 hours before it. All recorded seizures generalized, indicated by behavior ranging from 3-5 on Racine's scale (Racine, 1972, Electroencephalogr Clin Neurophysiol 32:281-294). The CA3 hippocampus was chosen in order to understand how the transition to seizure can occur within a local network. The CA3 in particular is centrally located in the hippocampal trisynaptic loop, between structures that receive inputs to the hippocampus (dentate gyms) and outputs to cortical structures (CA1). It has strong reciprocal connections (Wittner and Miles, 2007, J Physiol 584:867-883) within the network, and is therefore ideal for investigating how local neurons interact with each other. It has also been implicated in the seizure initiation process (Dzhala and Staley, 2003, J. Neurosci. 23(21):7873-7880; Derchansky et al., 2006, Neurobiol Dis., 23(2): 312-328) and epileptiform burst activity (McCloskey and Scharfman, 2011, Epilepsy Research 97(1-2):92-102). A total of 25 seizures were analyzed from 5 rats, while the number of seizures per rat ranged from 4 to 8.

Single-units and LFPs were examined during the period from 10 minutes before the onset of sustained ictal LFP spiking to 60 seconds after and were compared to a background period beginning 1 hour before and ending 10 minutes before the ictal spiking onset. The shapes of single-unit waveforms were stationary during these periods and sorting was performed by defining clusters using standard algorithms (Klustakwik 1.7, Ken Harris, Rutgers University) and then selecting single units from the clusters. Single units were separated into putative pyramidal cells (n=169) or interneurons (n=54) based on waveform shape and firing characteristics (Csicsvari, et al., 1998, Neuron 21:179-189) (FIG. 13).

Heterogeneous LFP Patterns at the Transition to Seizure

Figure 14:
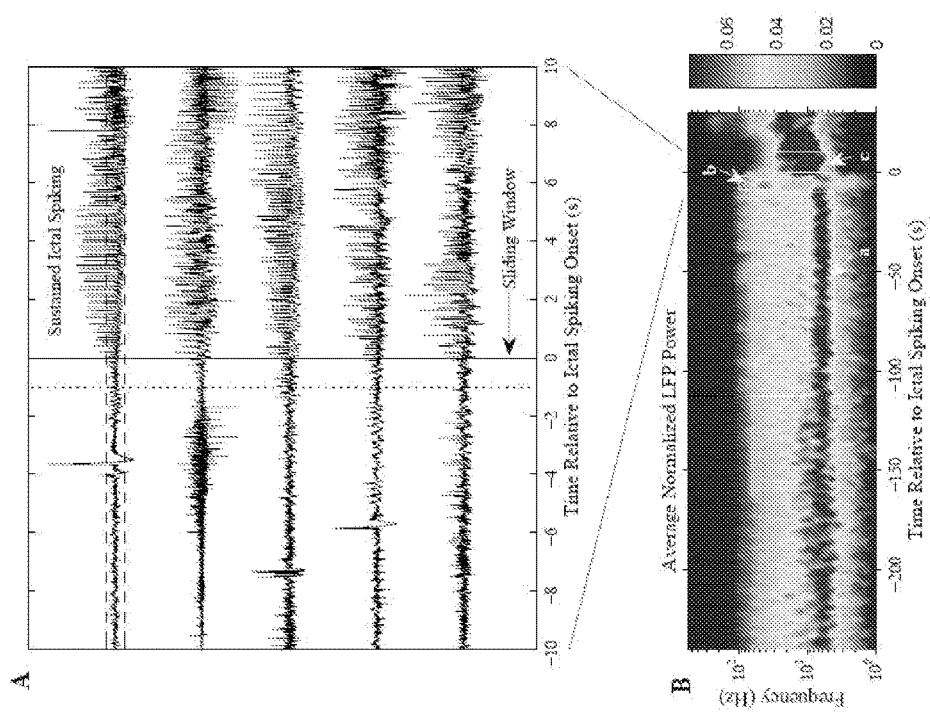
FIG. 14, comprising

In order to study the temporal dynamics of single unit activity within the confines of the well-known inter-seizure and inter-subject seizure onset diversity, a reliable and meaningful reference point around the time of seizure onset was needed. For the recorded seizures, a variety of seizure-associated LFP patterns were observed in the 8 seconds prior to the appearance of sustained ictal activity, including initial LFP population spike(s) and associated slow wave (Spencer, et al., 1992, Epilepsia 33:537-545; Bragin, et al., 2007, Epilepsia 48:1883-1894), low voltage fast (LVF) activity ((Allen et al., 1992; Bragin, et al., 2005, Epilepsia 46:1592-1598; Spencer, et al., 1992, Epilepsia 33:537-545), and very fast oscillations (Bragin, et al., 1999b, Epilepsia 40:127-137; Traub, et al., 2001, Epilepsia 42:153-170) (FIG. 14A). The most common pattern observed was a single LFP spike, followed by LVF activity at gamma frequencies. However, these patterns were variable in their prevalence, order, and time of occurrence with respect to ictal activity. In contrast, the start of sustained high amplitude ictal LFP spiking was a clearly observable event in every seizure. The ictal LFP spikes were typically positive-going for about 10 seconds, beginning with smaller amplitude spikes which gradually increased, similar to what others have observed (Bragin, et al., 1999a, Epilepsia 40:1210-1221; Bower and Buckmaster, 2008, J Neurophysiol. 99:2431-2442). After this time, the spikes changed appearance, becoming biphasic with higher frequency. Therefore the onset of sustained ictal spiking was used as a reference to temporally align all seizures, and the single unit dynamics before and after this transition were analyzed.

Visualizing the dominant LFP oscillations around the ictal spiking onset, three main events were visible. The first event was a narrowing of the theta frequency band from a broader 4-10 Hz to a more rhythmic or narrower 5-8 Hz band that occurred in the approximately 100 second period prior to ictal spiking onset (FIG. 14B—event a). The second event was a simultaneous emergence of dominant power in the delta (1-4 Hz) and gamma (30-100 Hz) frequencies from 8 to 2 seconds before ictal spiking (FIG. 14B—event b), corresponding to the appearance of slow waves and associated LVF activity mentioned above. The third event was the first 10 seconds of ictal LFP spiking, indicated by a change of dominant power to the band of 4-30 Hz (FIG. 14B—event c). These three events define time-frequency oscillation windows (a: −100 to −10 s, 4 to 10 Hz; b: −8 to −2 s, 30 to 100 Hz; c: 0 to 10 s, 4 to 30 Hz) that were used to identify changes in single neuron synchrony with the local field in a later section.

Changes in Single Neuron Firing Rate During Transition to Seizure

Figure 15:
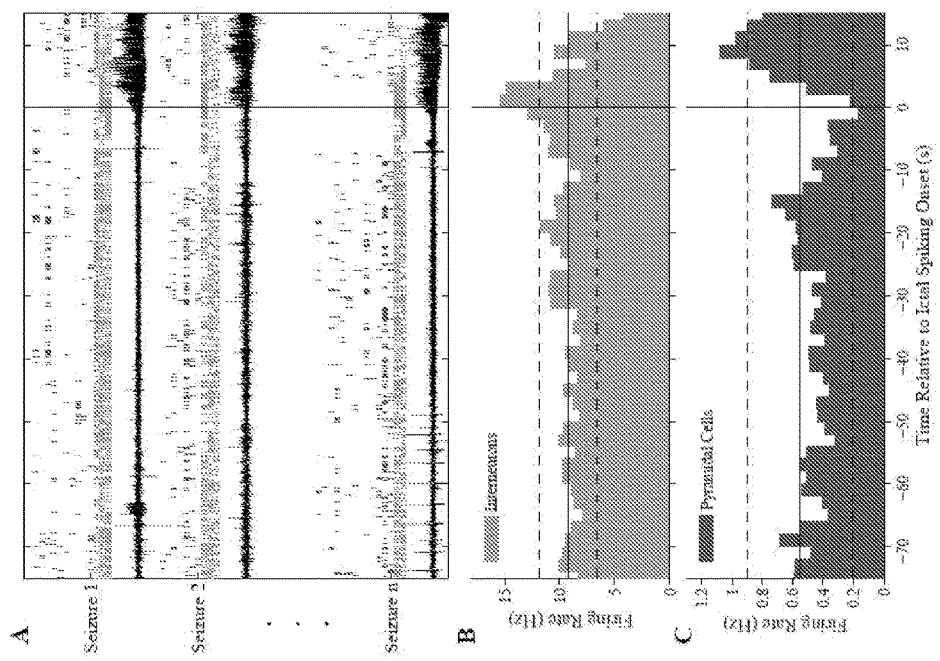
FIG. 15, comprising FIGS. 15A-15C, comprises a set of graphs illustrating the changes in average firing rate of neuronal populations during the transition to seizure.

Population peri-event time histograms (PETH) were generated separately for each population (putative pyramidal cells and interneurons) by averaging action potential (AP) counts in 2 second bins across all neurons of a type obtained from all seizures and all rats around the time of ictal spiking onset (FIG. 15). The population PETHs showed that the average activity of interneurons significantly increased in a span of time centered on, and maximal at, the time of ictal spiking onset. Concurrent with this event was a decrease in pyramidal cell activity. As time progressed and interneuron activity began to return to baseline levels, pyramidal cell activity significantly increased to a maximum occurring 8 seconds after the ictal spiking onset. While this is similar to patterns observed in studies of induced seizures (either chemically or electrically) (Velazquez and Carlen, 1999, Eur J Neurosci 11:4110-4118; Ziburkus, et al., 2006, J Neurophysiol 95:3948-3954; Timofeev et al., 2002, Neuroscience 114:1115-1132; Bragin et al., 1997, Neuroscience 76:1187-1203; Gnatkovsky, et al., 2008, Ann Neurol 64:674-686) it is demonstrated here that interneuron activation occurs before pyramidal cell activation at the onset of ictal spiking in spontaneous seizures from awake animals.

Figure 16:
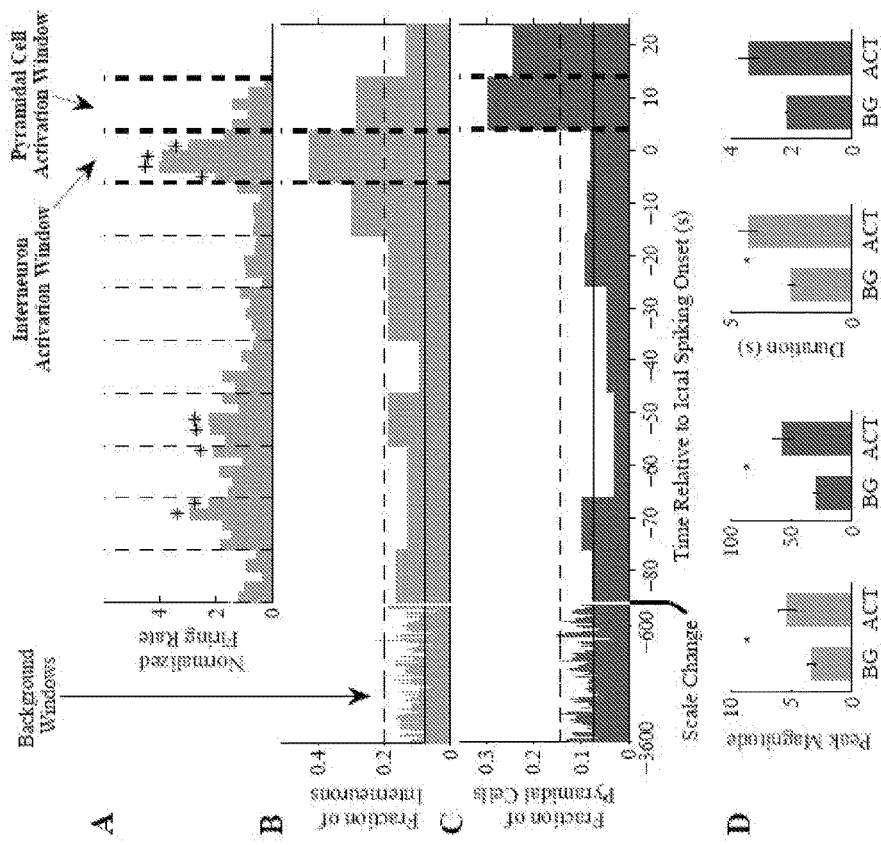
FIG. 16, comprising FIGS. 16A-16D, comprises a set of graphs illustrating the increases in firing rate of individual neurons.

It was of interest to determine whether these increases in activity came from a minority of neurons, or were a general population behavior. To that end, significant increases in firing rate were detected on an individual neuron basis (FIG. 16A) in their activation windows (interneurons: −6 to 4 s and pyramidal cells: 4 to 14 s). It was observed that 42.6% of interneurons and 30.6% of pyramidal cells recorded showed significantly increased activity within their respective activation windows compared with 7.1%, SD=2.4% for interneurons and 7.3%, SD=4.4% for pyramidal cells recorded during equivalent duration background windows (FIG. 16B and FIG. 16C). By subtracting the number of neurons with randomly increased activity, it was estimated that approximately 36% of interneurons and 23% of pyramidal cells participate in the increases in activity observed around the time of ictal spiking onset. The fraction of interneurons with increased firing rate is very similar to that previously estimated at the onset of human temporal lobe seizures (Babb, et al., 1987, Electroencephalogr Clin Neurophysiol 66:467-482) suggesting that the multi-unit activity seen in these early human studies could have been from interneuron populations. Moreover, recently it was demonstrated in human epileptic patients that more interneurons modulated their firing rate during the transition to seizure than pyramidal cells (Truccolo, et al., 2011, Nat Neurosci 14:635-641), similarly consistent with the present data. In addition to more cells firing, both cell types showed greater peak magnitudes (sign test, $p<0.01$) and interneurons showed longer duration of firing rate increase (sign test, $p<0.05$) in the activation window compared to background.

Single Neuron Synchrony with Local Field Oscillations

Figure 17:
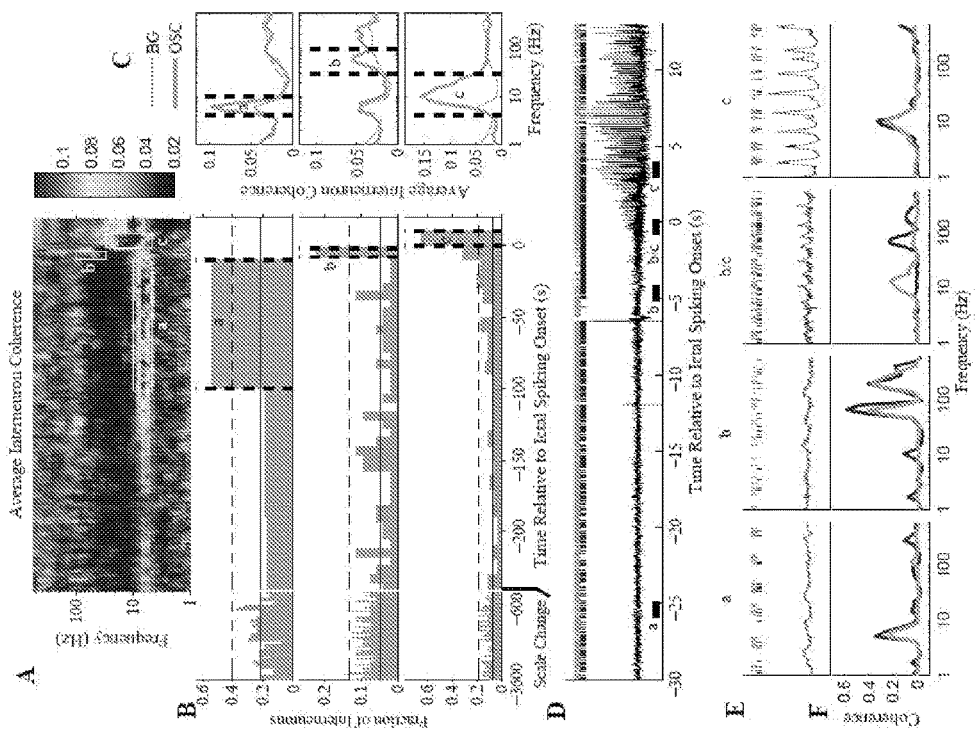
FIG. 17, comprising FIGS. 17A-17F, comprises a set of graphs illustrating the changes in coherence between interneurons and LFP oscillations during the transition to seizure.
Figure 18:
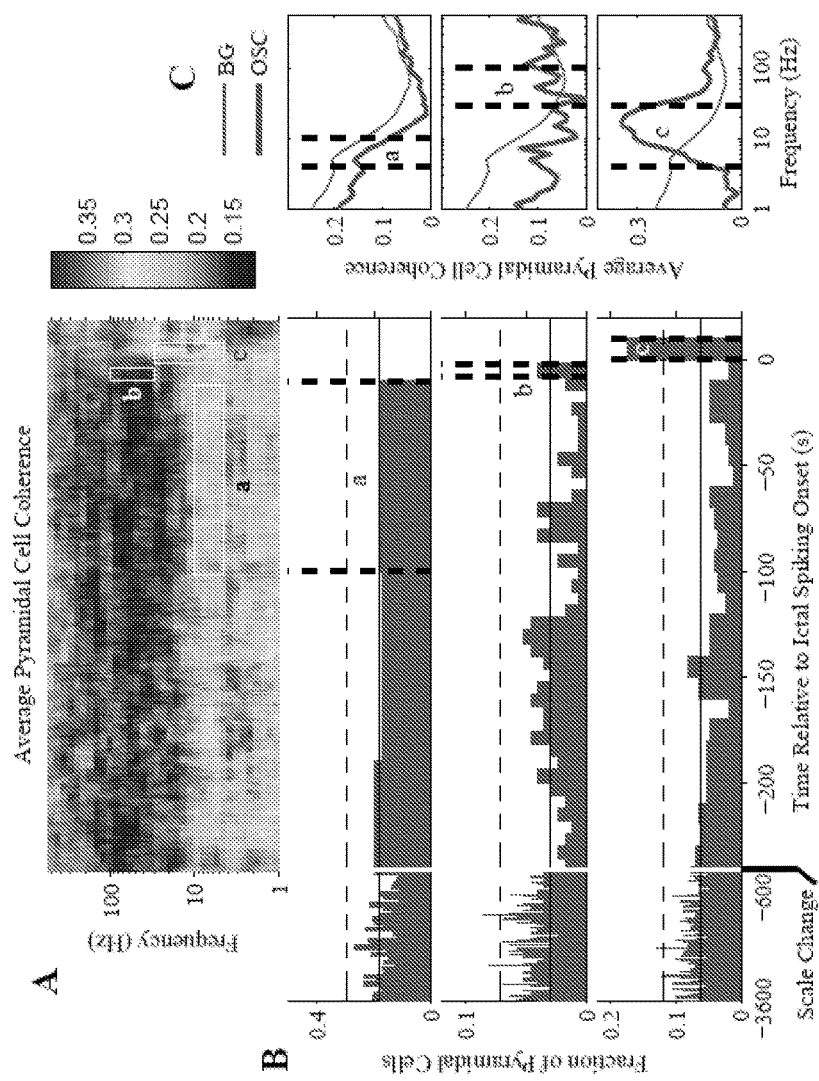
FIG. 18, comprising

Since a characteristic of seizures is oscillatory activity in the local field, it was investigated whether neuronal APs were coherent with the dominant LFP oscillations outlined above. First, coherence between the APs and local field (Fries, et al., 2001, Science 291:1560-1563; Grasse and Moxon, 2010, J Neurophysiol 104:548-558) was measured as a time-varying process for each neuron. For each population separately, the coherence across cells was averaged and plotted in a spectrogram (FIG. 17A and FIG. 18A). For interneurons, visual inspection of the spectrogram (FIG. 17A) showed that the averaged coherence increased in each of the LFP oscillation windows. For example, during the period (−100 to −10 s) of dominant theta (4-10 Hz) LFP power, average coherence was increased in the same band. In the 6-second period just prior to ictal spiking, changes in average coherence in the dominant power band (30-100 Hz) were less pronounced but still identifiable in the average. Finally, the largest increase in average coherence for the interneurons occurred in the first 10 seconds of ictal spiking, in the dominant power band (i.e. frequency of ictal spiking (4-30 Hz).

Detailed inspection of the coherence between the APs of single interneurons and the LFP oscillations revealed that these average increases in coherence were not the results of sustained increases in coherence throughout the window but rather originated from short bursts of coherence for each neuron (typically the higher the frequency the shorter the interval). The fraction of interneurons with a detected increase in coherence in each of the oscillation windows was significantly greater than in equivalent background windows (FIG. 17B). Therefore, more interneurons showed a high level of phase-locking to the on-going dominant local field oscillations (FIG. 17—events a, b, c) than in the background. Over 50% and 20% of interneurons increased their coherence with the field oscillation in the first two time-frequency windows (FIG. 17B—events a, b), respectively. The window for which the largest number of neurons had increased coherence was the third window (FIG. 17B—event c), where over 60% of interneurons were coherent with the ictal LFP spikes. To relate these results back to changes in firing rate, interneuron activation was shown to be greatest between the second and third oscillation windows (transition from gamma to ictal coherence). One example where two simultaneously recorded interneurons displayed all of the identified changes in coherence can be seen in FIG. 17D through FIG. 17F.

The average coherence for pyramidal cells (FIG. 18A) did not display the same increases as interneurons. In fact, pyramidal cells did not show any increase in coherence until approximately 5 seconds after ictal spiking onset at which point they became coherent with the ictal spiking frequency. In contrast to the fraction of interneurons with increased coherence, the fraction of pyramidal cells with increased coherence was not significantly different from the number identified in the background for the first two windows (FIG. 18B—events a, b). However about 15% of pyramidal cells eventually became more coherent with the ictal spiking frequency in the third oscillation window (FIG. 18B—event c).

Figure 19:
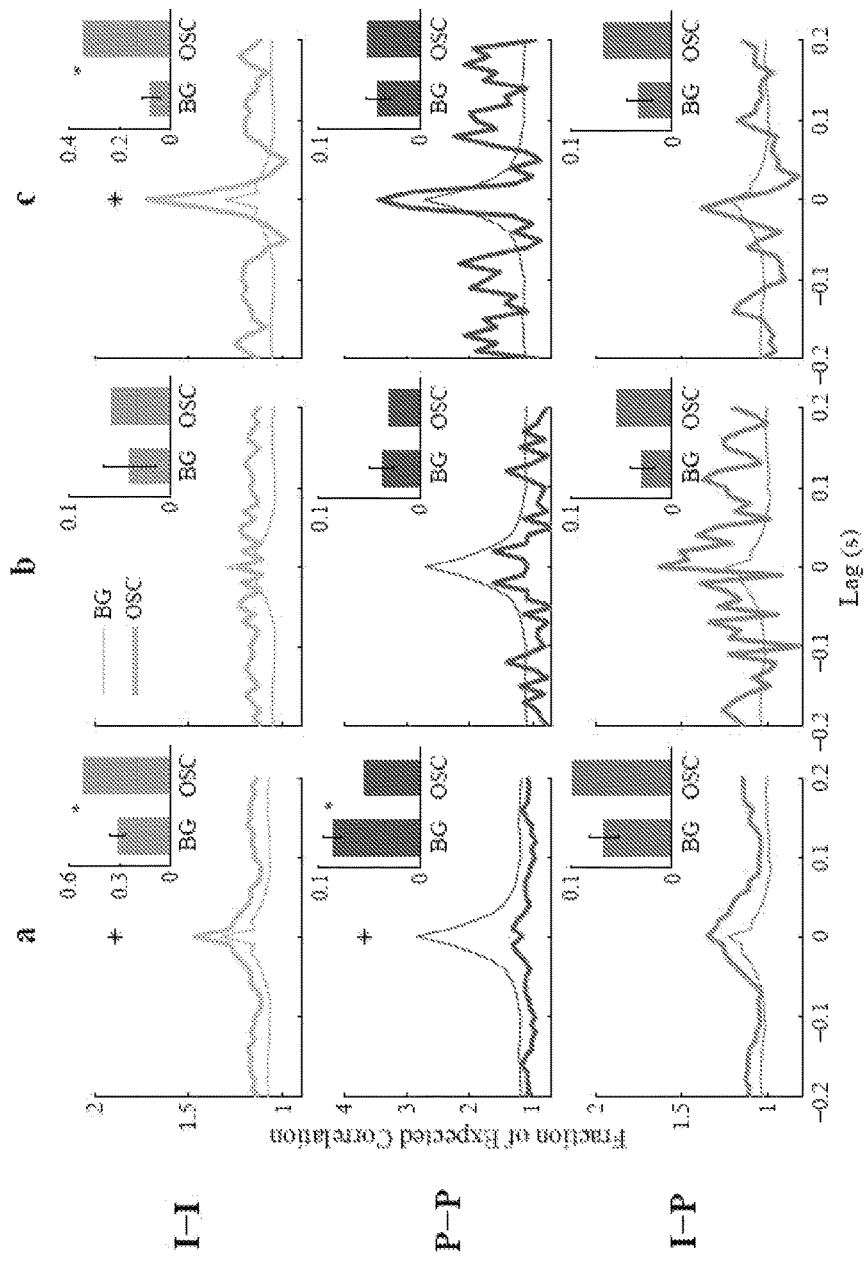
FIG. 19 is a set of graphs illustrating cross-correlations between single neuron spike trains. Each panel is the population cross-correlograms for either interneuron—interneuron (I-I), pyramidal cell—pyramidal cell (P-P), or interneuron—pyramidal cell (I-P) pairs measured within the three oscillation windows (FIGS. 13, 16, 17; a, b, c) and equivalent duration background windows. Bin size=10 ms. Thin lines are the average cross-correlograms over all background (BG) windows, while thick lines are cross-correlograms from each oscillation (OSC) window. In some cases, correlograms converge to the expected value at large lags (~1 s), and therefore this is not visible for the lag times displayed. Insets show the fraction of pairs that are significantly correlated at zero-lag, for background and oscillation windows. Error bars are the standard deviation of all background windows. Note that the fraction of correlated pairs is influenced by the duration of the window, and therefore background levels vary between windows.

To assess whether increases in AP coherence with the local field coincides with increases in the correlation between APs of different neurons, simple cross-correlations between neuronal activity of simultaneously recorded neuron pairs were computed during each oscillation window. The magnitude of the pooled cross-correlogram was greater in the first and third oscillation windows (FIG. 19a, FIG. 19c) than equivalent background windows. Also in these windows more interneuron-interneuron pairs were correlated than in background. The second window (FIG. 19b) showed no increase in the fraction of correlated pairs or the correlation magnitude, but a high frequency oscillation trend was visible around zero-lag, due, at least in part, to the high frequency coherence. Unlike interneurons, pyramidal cells showed a reduction in the magnitude of the cross-correlogram and a decrease in the number of correlated pairs in the first oscillation window (FIG. 19a). No significant differences in correlation between interneurons and pyramidal cells (or vice versa) were found.

Independence of Interneurons Participation in Different Neuronal Behaviors

Figure 20:
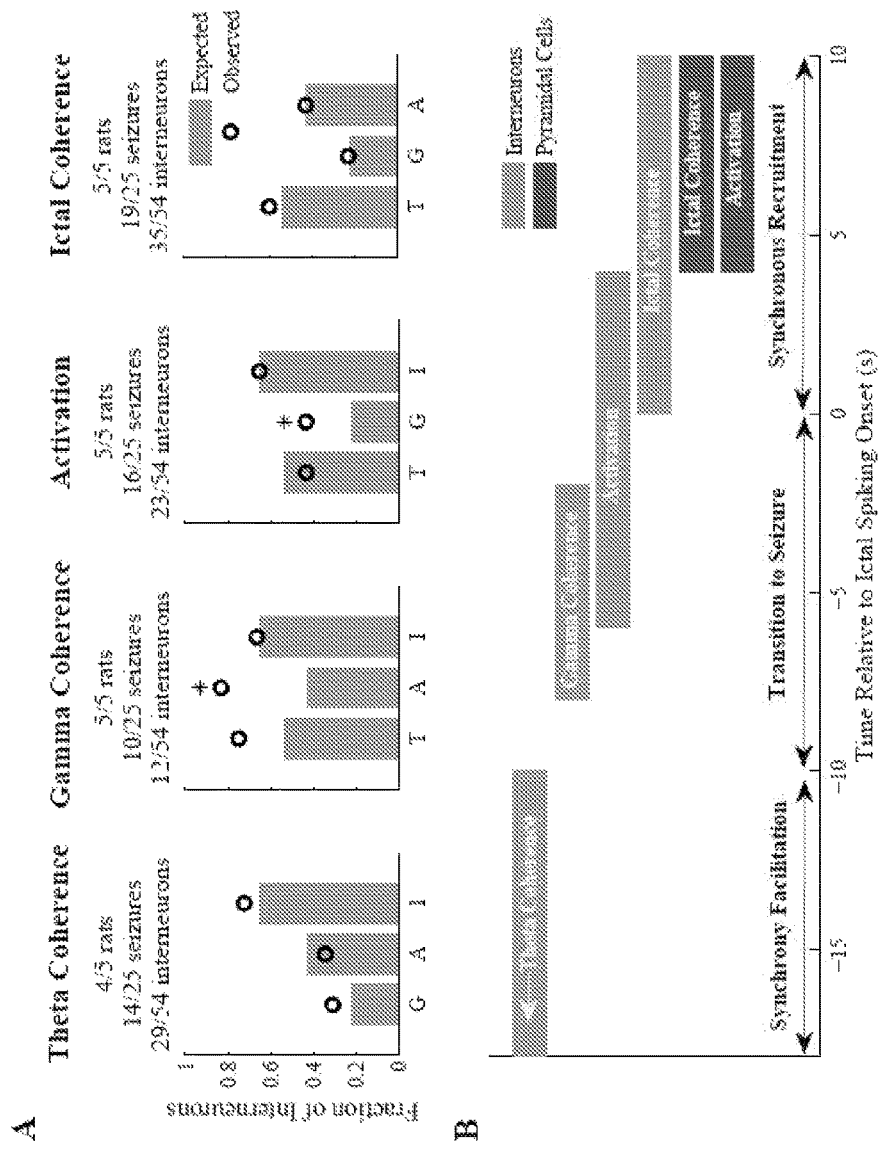
FIG. 20, comprising

The results given thus far constitute evidence of a set of distinct neuronal behaviors, primarily interneuron synchrony patterns, which occur at specific times in the transition to sustained ictal spiking. These include coherence between interneurons APs and the LFP oscillations (theta, gamma, and ictal) in the three oscillation windows, and high firing rate in the interneuron activation window. However, it is unclear whether the cells participating in each of these distinct neuronal behaviors are the same across behaviors or are a random set of cells drawn from the population for each behavior. To test this the probability that cells participating in one of the behaviors would also participate in another behavior was estimated (FIG. 20A). In general, this did not seem to be the case. For example, those interneurons that were coherent with ictal spiking were no more likely than chance to participate in any of the other neuronal behaviors identified. However, there was one exception. Those interneurons that were coherent with the gamma oscillation tended to be the same neurons that exhibited neuronal activation and vice-versa. Without wishing to be bound by any particular theory, this is likely due to the fact that strong activation of interneurons has been shown to be involved with the generation of gamma oscillations. In fact, these two behaviors overlapped in time, with increases in gamma coherence preceding interneuron activation on average. For these reasons, the gamma coherence and the increased firing rates are considered to be related, and potentially due to the same mechanism.

Stages of Interneuron Synchronization During the Spontaneous Transition to Seizure These data describe, for the first time, three distinct stages of interneuron synchronization during the spontaneous transition to seizure in the CA3 hippocampal network (FIG. 20B). Beginning minutes before the seizure, there was an increased likelihood that interneurons would be coherent with theta LFP oscillations. Next, the transition to seizure occurred in the approximately 10 second period before ictal spiking, during which time interneurons were coherent with gamma oscillations and began to display increases in firing rate. At the onset of ictal spiking, interneuron firing rates were high, but began to drop as pyramidal cell firing rates increased approximately 4 seconds later. Both cell types were coherent with the ictal spiking during this period. Together these findings support the theory that interneurons play a crucial role in transitioning a network from interictal to ictal states and help clarify the seemingly incongruous data from human studies (Truccolo, et al., 2011, Nat Neurosci 14:635-641; Babb, et al., 1987, Electroencephalogr Clin Neurophysiol 66:467-482).

Synchrony Facilitation

In the hippocampus of normal animals, it is natural for neurons to be phase-locked to a predominant behavior-dependent theta rhythm that is driven by input from both the medial septum and the entorhinal cortex, although hippocampal interneurons are also important for maintaining this rhythm (Ylinen, et al., 1995, Hippocampus 5:78-90; Stewart and Fox, 1990, Trends Neurosci 13:163-168; Montgomery, et al., 2009, J Neurosci 29:1381-1394). However, during the minutes before the onset of ictal spiking, the theta oscillation is more rhythmic (narrowing of the theta band) likely due to the large proportion of interneurons that are coherent with it. These two phenomena describe a period of high theta synchrony.

Pathological neuronal activity in this prolonged window is not unique to the CA3 and in fact coincides with increased variability in granule cell firing before spontaneous seizures (Bower and Buckmaster, 2008, J Neurophysiol. 99:2431-2442), and a concentration of the theta band recorded from DG (Queiroz, et al., 2009, J Neurophysiol 101:1588-1597) in the minutes before seizure onset. This increased coherence in CA3 could be due, in part, to a dysfunction of normal entorhinal cortex (EC) operations (Bartolomei, et al., 2005, Epilepsia 46:677-687; Kispersky, et al., 2010, PloS One 5:e13697). For example, CA3 theta oscillations have been shown to be more locally synchronous when the EC is lesioned (Cappaert, et al., 2009, Hippocampus 19:1065-1077).

Either alternatively to, or in conjunction with dysfunction of EC driven theta, the medial septum is likely to play a part in the pathological theta synchrony observed before seizure onset. Highly rhythmic theta oscillations concurrent with rhythmic unit activity were observed in the hippocampus and/or medial septum (Kitchigina and Butuzova, 2009; Butuzova and Kitchigina, 2008) prior to seizures induced in the septum. This highly rhythmic theta activity was considered to be mechanistically different from native theta oscillations, which have been shown to suppress interictal spikes (Colom, et al., 2006, J Neurophysiol 95:3645-3653). Regardless of an EC or septal origin of the observed activity, the result is likely to be potentiation of synapses between small networks of cells in the hippocampus, since theta has been shown to be the optimal frequency for this process (Larson, et al., 1986, Brain Research 368:347-350; Huerta and Lisman, 1993, Nature 364:723-725).

Transition to Seizure

The period of time from the end of the synchrony facilitation phase through to the start of sustained ictal spiking is the transition to seizure since the preictal LFP population spikes, slow waves, and LVF activity observed in the present study have been previously implicated in seizure initiation (Spencer, et al., 1992, Epilepsia 33:537-545; Bragin, et al., 2007, Epilepsia 48:1883-1894; Allen et al., 1992, Electroencephalogr Clin Neurophysiol. 82:155-159; Bragin, et al., 2005, Epilepsia 46:1592-1598). Population spikes in the hippocampus have been well studied and are known to be produced by excitatory bursts of pyramidal cells (Csicsvari, et al., 2000, Neuron 28:585-594). It has been proposed that the preictal spike is due to a pathologically interconnected neuron (PIN) network (Bragin, et al., 2000, Epilepsia 41(Suppl 6):S144-S152; Bragin, et al., 2007, Epilepsia 48:1883-1894). It is suggested herein that the high theta synchrony could activate an existing dormant PIN network or, alternatively, a temporary assembly of PINs could be formed by synaptic potentiation during the synchrony facilitation phase.

Without wishing to be bound by any particular theory, the coherence between interneurons and gamma oscillations (LVF activity) observed is likely to be caused by the preictal LFP spikes since it has previously been shown that CA3 interneurons will oscillate at this frequency in response to an epileptiform population spike in vitro and in vivo (Traub, et al., 1996, J Physiol 493(Pt 2):471-484). The prolonged firing rate increase associated with this coherence could be due to an increased excitatory driving force. For example, excitatory input could come from CA3 afferents including EC (Kispersky, et al., 2010, PloS One 5:e13697) or DG (Bower and Buckmaster, 2008, J Neurophysiol. 99:2431-2442) but is unlikely to come from local pyramidal cells since they are inhibited during this period. Alternatively the driving force could come from changes in the extracellular chemical environment (Dzhala and Staley, 2003, J. Neurosci. 23(21): 7873-7880; Shin, et al., 2010, Brain Res 1331:39-50; Eid, et al., 2004, Lancet 363:28-37).

Synchronous Recruitment

At the beginning of ictal spiking, interneuron firing rate was high, but dropped below baseline levels over the next 10 seconds. This was also the time when interneurons switched their coherence from gamma to the frequency of ictal spikes. Without wishing to be bound to any particular theory, this switch is unlikely to be due to the slowing of the gamma frequency known to occur as the level of excitation to interneurons decreases (Traub, et al., 1996, J Physiol 493(Pt 2):471-484) since the firing rate of the interneurons remains high during this period. Moreover, the switch to a lower frequency is not a continual shift in frequency, but rather a separate oscillation mode since these oscillations often simultaneously coexist (Kopell, et al., 2000, Proc Natl Acad Sci USA 97:1867-1872)(FIG. 17E—events b,c). Others have shown that this switch could be due to a gradual alteration of a network parameter including accumulation of extracellular potassium (Shin, et al., 2010, Brain Res 1331: 39-50), deficits in somatic or dendritic inhibitory efficacy (Wendling, et al., 2002, Eur J Neurosci 15:1499-1508), or changes in slow potassium currents (Kopell, et al., 2000, Proc Natl Acad Sci USA 97:1867-1872). The frequency switch observed at ictal spiking onset could be due to one of these mechanisms.

The last component of this stage is an increase in pyramidal cell activity that peaks approximately 8 seconds after the onset of ictal spiking. This has been shown to occur in in vitro studies in response to strong interneuron input. The mechanisms responsible for this vary according to the study, and include intrinsic rebound excitation of pyramidal cells after a reduction in IPSP efficacy due to depolarization block (Ziburkus, et al., 2006, J Neurophysiol 95:3948-3954), an excessive accumulation of extracellular potassium (Gnatkovsky, et al., 2008, Ann Neurol 64:674-686), or GABAergic currents becoming excitatory due to excess chloride in the pyramidal cell bodies (Timofeev et al., 2002, Neuroscience 114:1115-1132). Not only are the pyramidal cells more active than usual at this time, but they are also coherent with the frequency of ictal spiking. This suggests that synchronous pyramidal cell activity is initiated at a delay relative to the onset of ictal spiking and is likely recruited by the synchronous interneuron activity.

The results of this study explain much of the ambiguous results from studies where single neurons recorded from human patients over the past 40 years. While previous studies found heterogeneous firing patterns in the transition to seizure (Babb et al; Truccolo et al, 2011, Nature Neuroscience, 14, 635-641), the numbers of neurons whose firing rate was modulated is similar to the numbers found in the present study. By using the changes in the local field potential as a guide to the underlying changes in neuronal activity, distinct spatio-temporal patterns were able to be identified, suggesting that the heterogeneous firing rate across large populations of cells may be explained by clusters of synchronization within subpopulations of neurons.

This study, therefore, offers the first detailed analysis of synchronous neuronal activity during the transition to spontaneous seizures and, importantly, identifies a specific sequence of interneuron behaviors prior to the onset of a seizure, establishing an explicit role of synchronous inhibition in this process. In addition, it is proposed that the increased coherence between interneurons and theta activity is responsible for temporarily potentiating synapses of hippocampal neurons, which leads to synchronous seizure initiating events. Although in vitro models have suggested a role for interneurons in seizure initiation, it is important to distinguish between the effects of the seizure induction agent, and the process by which a chronically pathological network can intrinsically generate a seizure. Therefore, this study represents an important step in demonstrating the role of synchronous inhibition in the generation of spontaneous seizures within a local network. The consistency of the presented results with existing human studies suggests that these mechanisms will likely translate to human ictogenesis and this may open up new opportunities for therapy development by targeting the specific activity in these stages of seizure initiation.

Example 4

Seizure Prediction Using Single Neuron Activity

It is not surprising that seizure prediction has been an object of focus for at least the last 30 years since it is the spontaneity of seizures which makes them so difficult to treat. The vast majority of this work has used macro EEG signals to try to infer information about the state of the brain, with little success in identifying a specific preictal pattern that does not occur during interictal periods (Mormann et al., 2007, Brain 130:314-333). Although easy to obtain, these signals provide little information about underlying excitatory, inhibitory, or synchronous neuronal activity that may be responsible for generating the seizure.

It was examined whether recording from excitatory and inhibitory populations of neurons can be used to effectively identify a preictal state in a spontaneous seizure model by training a learning machine (support vector machine or SVM) to recognize the difference between the neuronal patterns occurring just before seizure, and patterns occurring interictally. The SVM was chosen as a classifier because it has a strong mathematical framework, and therefore possesses the desirable theoretical properties of simple linear classifiers. Additionally, SVMs allow for the possibility of nonlinear decision boundaries by using kernels to transform the data into a new nonlinear space. The firing rate and spike field coherence measures described elsewhere herein were used as variables that informed the SVM how to distinguish between interictal and preictal states.

To be effective as a warning system or as a trigger for anti-seizure stimulation, it was determined that the algorithm must predict the seizure at least 10 seconds before ictal spiking begins. From the results presented elsewhere herein, the LFP patterns commonly associated with seizure onset occurred within 10 seconds of the start of ictal spiking. Therefore, so as to be predicting the seizure and not just detecting seizure onset, a goal of the present study was to classify the neuronal patterns that occurred in the minutes before this 10-second transition period.

Having high prediction sensitivity is important for any practical application where it is critical not to miss a seizure (e.g. preventative electrical stimulation). Lower false positive rates are always better, and acceptable levels should be determined by the application. Therefore, a major question posed was, what is the lowest false positive rate attainable with 100% sensitivity? By utilizing the trained SVM in a sliding window algorithm, it was shown to be able to predict 100% of seizures 10 seconds in advance with a false positive rate of 30%. This level of performance suggests that this type of algorithm would be appropriate for implementation in a closed-loop stimulation therapy, where the goal is to interrupt the seizure generation process by a timely electrical stimulus to the brain.

The materials and methods employed in these experiments are now described.

Data Set

The data set used for this chapter was obtained from the experimental procedure described in elsewhere herein. Putative pyramidal cells and interneurons were discriminated from extracellular tetrode recordings taken in dorsal CA3 hippocampus. Rats had previously been given pilocarpine to induce status epilepticus, and were implanted with tetrodes once spontaneous seizures began to manifest (~1 month). The action potentials of the neurons, along with the local field potential, were recorded beginning two hours before each spontaneous seizure, and ending ten minutes after seizure. The background, or interictal period, was defined as being at least 10 minutes before seizure. From previous results, the earliest observable preictal changes in neuronal firing patterns occurred in a window of time of approximately 2 minutes before seizure. Therefore, the period of time from −130 to −10 s with respect to the ictal spiking onset was classified as preictal for training purposes. Although not always the earliest LFP indicator of seizure, the ictal spiking onset was used as a reference to show that prediction could be accomplished at least 10 seconds before this point.

Neuronal Measures

To detect increases or decreases in firing rate, the instantaneous firing rate was calculated at any given time by taking the reciprocal of the time difference between consecutive action potentials. Although firing rate is not usually normally distributed, log transforming the instantaneous firing rate made the distribution approximately normal. This was useful when detecting statistical deviations outside the previous range of values. Furthermore, small differences between very low firing rates were magnified with this transformation since the instantaneous firing rate is always non-zero by definition.

Coherence between action potentials and local field oscillations (spike field coherence or SFC) was estimated as a time-varying process in the same manner as described elsewhere herein (Example 2). Segments of the filtered LFP that occurred around the time of each AP were averaged to create a spike-triggered average. The central peak amplitude of this average LFP was normalized to the average peak amplitude from all LFP segments to obtain the biased (by number of APs) estimate of coherence in given band. The estimate of coherence for a neuron at a given point in time was obtained from the previous n APs and the simultaneous LFP. For each neuron, n was fixed so that the bias would be equal at each point in time. This number (n) was at least 5, but otherwise equal to twice the neuron's average firing rate over the seizure period, rounded to the nearest integer. Repeating this estimation procedure at 100 ms intervals for each frequency band produced a time-frequency estimate of the SFC for each neuron, where the coherence at each frequency could be considered a separate neuronal measure.

Data Binning and Normalization

All neuronal measures were binned in time within the target and trailing components of the sliding window for the following reasons. First, learning algorithms require a training set with multiple samples from each class, where each sample has dimensionality equal to the number of variables measured. The ideal way to implement this is by using an interictal and a preictal period from each seizure as samples, making the total number of samples in each class is equal to the number of training seizures. However, since not all neuronal measures could be obtained for every seizure (e.g. no interneurons recorded in some cases) the set of measures used had to be common between the training data and testing data. Therefore, samples from multiple seizures could not always be combined to train the algorithm, and so the training process had to be accomplishable within a single seizure period. This necessitated breaking up the 2-minute preictal period (and the background period) into multiple bins, so that each bin was considered an interictal or preictal sample for that seizure period. For measures that had a finer time resolution than 0.5 seconds, values occurring within a bin were averaged. An added benefit of binning the data in this way is that many preictal firing patterns observed were of brief duration, and may have been washed out if averaged over 2 minutes. It was determined that a bin size of 0.5 seconds was an appropriate tradeoff between the ability to detect briefly enduring patterns, and the variance of the measures. Therefore, the complete training set for each seizure consisted of the 240 bins in the preictal window, and 240 randomly chosen bins from the background period.

Regardless of whether the target sliding window is positioned over the preictal window or somewhere in the background, normalization is accomplished the same way. The values obtained for a given measure from all 1200 bins in the trailing window were rank ordered. In this way, any bin from the target window could be converted to a non-parametric percentile (probability) of the distribution in the trailing window. This works well when target bins are within the distribution range, but without a parametric fit of the distribution, there is no good way to know how far outside the distribution range a target bin may be. Therefore, the trailing distribution was also treated as normal, and the probability of target bins obtaining their values was estimated using this assumption. The parametric and non-parametric probability scores were averaged for each target bin in order to get an accurate estimate of the probability of each target bin obtaining its value. All probabilities were log transformed and given a pseudo-sign (negative if the raw deviation was a decrease) before being fed into the algorithm.

SVM Training, Testing, and Optimization

As mentioned previously, training the algorithm was accomplished using interictal and preictal data from a single seizure. The neuronal measures from the 240 preictal bins and the 240 randomly chosen interictal bins in the training set were the same measures as those available in the seizure period to be tested. Instead of feeding all neuronal measures (dimensions) into the SVM, the dimensionality of the data was reduced by finding the first n principal components of the data. These components are the linear combinations of the original data that contain the most amount of variance. The coefficients representing these components were then used to transform all training and testing data to the new principal component space. Here, the number of components used, n, was a parameter found by the optimization procedure described below. This dimension reduction technique reduced the number of variables the SVM needed to use, improving computation time. Next, the training data underwent an additional transformation determined by a kernel function which could map the variables into a new nonlinear feature space. This is standard practice for SVM implementation, and allows nonlinear decision boundaries to be utilized when classes are not well distinguished by the difference between class means. The choice of kernel function was again, a parameter to be optimized. After transformation, the SVM produced the optimal soft margin hyperplane (decision boundary) that would be used on the test data set.

For the testing phase, the sliding window was stepped in 2-minute increments from 2 hours prior to seizure, until the final position at 10 seconds prior to ictal spiking. At each time step, neuronal variables were measured and transformed onto the projection axes from the training interictal principal components. The SVM was then asked to apply the same kernel transformation as in training and return the number of bins in the target sliding window that were classified as preictal. The fraction of preictal bins in the target window gave the probability that the current moment in time is preictal and not interictal. However, in practice it was observed that due to differences between individual seizures, some training/testing combinations resulted in high preictal probabilities at all times, and the opposite in some other combinations. Therefore, a final normalization was applied to the time-varying probability by dividing by the average probability value in the two hours before seizure. This transformation helped to downplay predictors that produced a more-or-less constant probability over time, and emphasized predictors which produced mostly low probabilities, with occasional moments of high probability. Using more than one training seizure to predict a test seizure was done by simply averaging the final outputs (normalized probabilities) of the SVM obtained from the training seizures.

Testing was performed in two different ways: a "within rat" paradigm and a "between rat" paradigm. The within rat paradigm was to train and test the SVM on different seizures from the same rat. The between rat paradigm involved testing the seizures from a rat using only the seizures from other rats for training. For both of these paradigms, a single quantity was used to judge the performance of the algorithm, which was related to both the sensitivity and specificity of the decision boundary. This quantity was obtained by taking the output of the algorithm when the target window was overlapping the 2-minute preictal window, and ranking this value with respect to the distribution of values the algorithm took in the previous 2 hours. In other words, the quantity used to evaluate performance was the percentile of the preictal value within the distribution of interictal values for a given seizure. In effect, the algorithms preictal percentile was a measure of sensitivity, but could also be interpreted as the minimum false positive rate required to detect the seizure. This false positive rate is the fraction of interictal time that the algorithm is predicting a seizure. Since each seizure tested had a different minimum false positive rate (preictal percentile), ROC curves were constructed that displayed the tradeoff between fraction of total seizures predicted (sensitivity) and the false positive rate required to predict this fraction (specificity).

The results of the experiments are now described.

Figure 21:
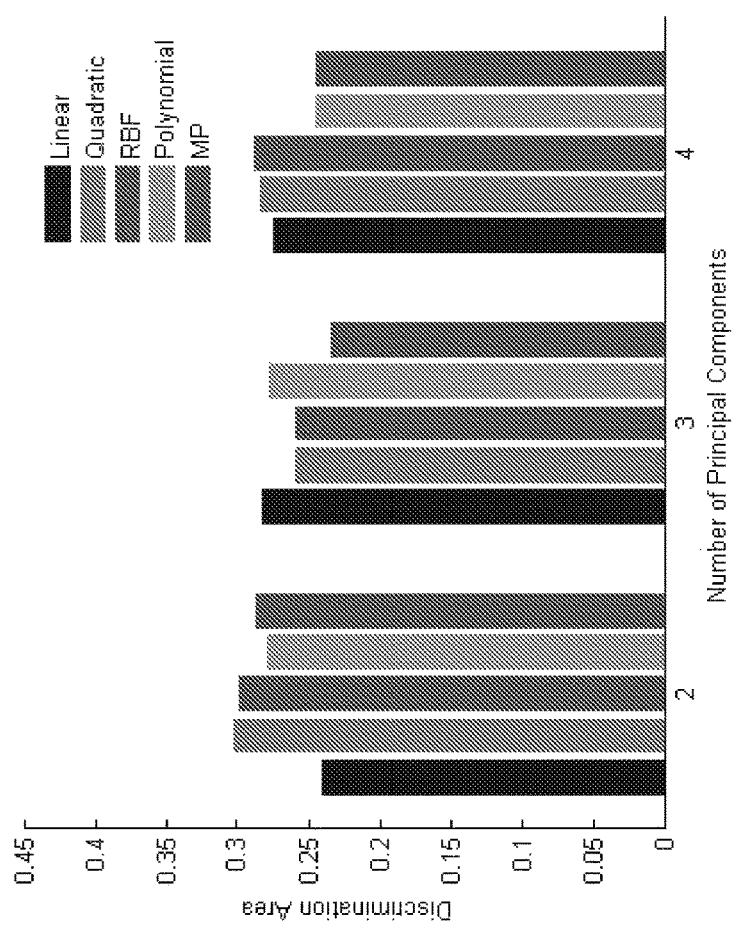
FIG. 21 is a graph illustrating the results of performance optimization. Bars display the average discrimination area (area between ROC and ND line) for within rat and between rat paradigms. This quantity was measured for kernel functions: linear, quadratic, radial basis function, polynomial, and multilayer perceptron. For each kernel function, between 2 to 4 principal components were used from the original data.

Optimization of the algorithm was achieved by conducting a parameter search over the number of principal components to include in algorithm training, and a choice of five common SVM kernel functions (linear, quadratic, radial basis function, polynomial, and multilayer perceptron). For each parameter combination, the algorithm was trained and tested on all available seizures within rats, and again for seizures between rats. The results of testing produced ROC curves for both types of training/testing paradigms. The area between the ROC curves and the line of no discrimination was calculated, and these areas were averaged for the two paradigms to obtain the final objective function. FIG. 21 summarizes the optimization results.

Overall, the optimization process did not have a great effect on the algorithm performance since the discrimination area did not vary greatly over different parameters. Including more principal components did not seem to improve performance, and the best performing kernel functions tended to be the quadratic and radial basis functions. Therefore, the subsequent results shown are for the first 2 principal components and a radial basis function kernel.

Figure 22:
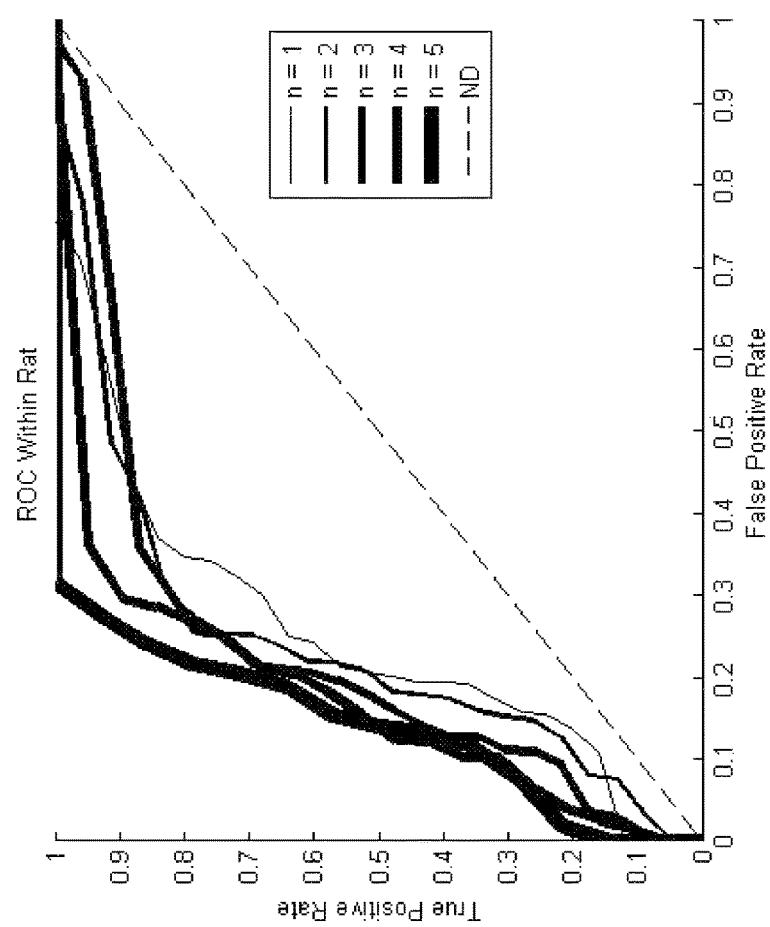
FIG. 22 is a graph illustrating algorithm performance when training was done within rat. The radial basis function kernel was used with 2 principal components from the original data. Different ROC curves represent the number of seizures (n) used to train the algorithm. The dashed line is the line of no discrimination.

The within rat performance of the seizure prediction algorithm is summarized by the ROC curves in FIG. 22. The number of seizures used to train the algorithm was varied from 1 to 5, and this factor clearly had an effect on the algorithm performance. Data limitations prevented exceeding 5 training seizures for this paradigm, but it seems that using more seizures to train gives the algorithm better discrimination ability. When 5 training seizures were used, the algorithm was able to predict 100% of seizures, with a 30% false positive rate (predicting a seizure 30% of the time).

Figure 23:
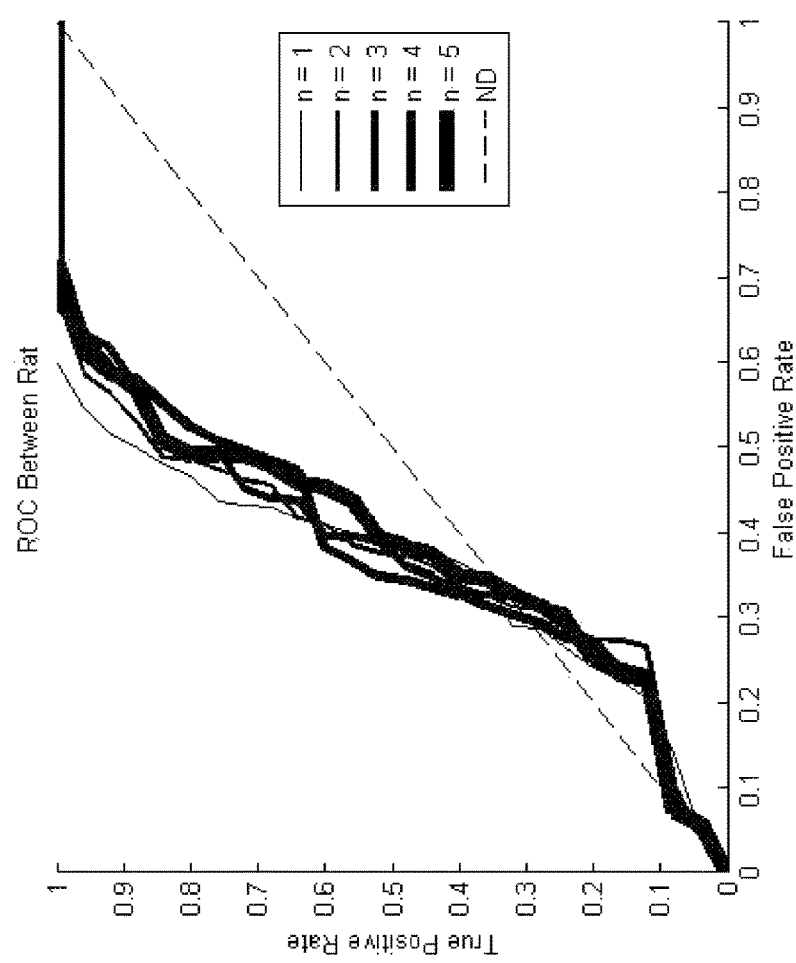
FIG. 23 is a graph illustrating algorithm performance when training was done between rats. The radial basis function kernel was used with 2 principal components from the original data. Different ROC curves represent the number of seizures (n) used to train the algorithm. The dashed line is the line of no discrimination.

The algorithm's performance was not as good when seizures from different rats were used in training (FIG. 23). Although better than a random predictor, a much higher false positive rate is required to have nearly perfect sensitivity. In contrast to the within rat paradigm, the number of training seizures seemed to have little effect on the algorithm performance.

SVM Algorithm Classification of Brain State

These results summarize the ability of a support vector machine algorithm to classify a preictal state from an interictal state based on neuronal firing rate and spike field coherence patterns. SVMs were an ideal classifier choice because 1) they have a simple mathematical formalism, 2) they are not affected by the curse of dimensionality, and 3) nonlinear transformations of the data may be optionally investigated. When seizures from a subject were used to predict seizures from the same subject (within rat), this algorithm was able to predict 100% of seizures with a false positive rate of 30%. This is an important statistic for applications that require every seizure to be predicted, however if this constraint was relaxed for other applications, lower false positive rates were obtainable by allowing a lower true positive rate.

Optimization of the SVM seemed to have little effect on algorithm performance, and importantly, the performance of the linear kernel did not seem to be systematically different from the nonlinear kernels. This indicates that the classification of this data is robust and may be accomplished with a simple linear classifier. Similarly, increasing the number of principal components did not have any apparent effect on performance, suggesting that most of the information needed to classify the neuronal patterns could be found in the first one or two principle components.

The effect of the number of seizures used to train the algorithm was apparent for the within rat paradigm, but not for the between rat paradigm. One explanation may be that the common preictal patterns between rats are not so specific to seizure, but are robust. Whereas, the preictal patterns within the same rat may be more similarly time-locked to ictal spiking onset, revealing subtler differences from interictal patterns as more seizures are used in training. In general it is not an unexpected result that seizures from a rat would be better predicted when seizures from the same rat are used to train the algorithm, and this is an important consideration when implementing this system in practice.

The performance statistics presented here suggest that this algorithm is more appropriate for use with a responsive electrical stimulation therapy than an early warning system. An early warning system, which would notify the subject when a seizure is imminent, requires a very specific predictor since it loses its effectiveness when warnings are given frequently. A 30% false positive rate would not be useful here since warnings would be given far too frequently to have some meaning Conversely, responsive neurostimulation, currently in clinical trials at NeuroPace Inc., does not give an early warning but delivers an imperceptible stimulation when a seizure is detected (after it has started). Recent clinical studies show that this therapy reduces seizures in 37% of patients (Morrell, 2011, Neurology 77:1295-1304), but this may be improved by stimulating before the seizure instead of after detection. The reported average false positive rates are 6.6/hour (Kossoff, et al., 2004, Epilepsia 45:1560-1567), which is approximately equal to 22% false positive rate by the convention of the present study. The 30% false positive rate reported herein is comparable with this number, suggesting that without greatly increasing the frequency of false positive stimulations, implementing this algorithm to predict seizures could make stimulation more effective by delivering it before the seizure has started.

Example 5

Derivation of the Bias Correction

The PS-SFC estimation method requires that the variance (power) must be estimated for each frequency component in the STA. However, this derivation requires the assumption that the power of a signal can be measured exactly. Fortunately, the bias correction is a robust procedure in that this assumption does not have to be met for the correction to perform well. This is demonstrated in the results presented herein, where the bias is reduced when the power is only estimated. Although this derivation is based on the variance of the STA, it applies equally well to the FB-SFC definition of coherence, since ideally the filtered STA has variance equal to the peak amplitude squared.

The variance in an STA can be thought of as coming from two independent sources: the variance of the signal that is time-locked to the spikes, and the variance of the uncorrelated or random noise present in the LFP. For a given frequency, the j-th LFP segment in an STA can be represented as $$s_j = x + y_j \quad (9)$$

where x is the coherent signal component and y is the uncorrelated noise component. A stationary coherence is assumed, in that the coherent component of each LFP segment is the same. The parameter to be estimated is the asymptotic coherence, c. In this formalism, asymptotic coherence can be defined as the fraction of variance in the time-locked signal, x, contained in the variance of the total signal, x+y.

$$c = \frac{\sigma_x^2}{\sigma_s^2} = \frac{\sigma_x^2}{\sigma_{x+y}^2} \quad (10)$$

Since the relative contributions from these components are generally unknown, averaging is relied upon to reduce the noise component and reveal the signal component. The definition of the SFC estimator is given by the variance of the STA divided by the variance of the LFP.

$$\hat{c} = \frac{\sigma_A^2}{\sigma_s^2} \quad (11)$$

The spike triggered average, A, constructed from n spikes is defined as $$A = \frac{1}{n}\sum_{j=1}^{n} s_j = x + \frac{1}{n} \quad (12)$$

The variance of the STA can now be substituted into equation 11. The bias in this estimator becomes apparent as the terms are expanded. x and y are independent variables by definition so the variance of their sum is equal to the sum of their variances.

$$\hat{c} = \frac{\sigma_A^2}{\sigma_s^2} = \frac{\sigma_x^2}{\sigma_{x+y}^2} + \frac{\sigma}{\sigma_x^2} \quad (13)$$

The estimator is equal to the asymptotic coherence plus an additional term. Here it is helpful to think about the numerator of the second term in equation 13 as the variance of a sampling distribution of means. Since y has no dependence on the spike times, $y_1, y_2, \ldots, y_n$ are independent. Therefore $$\sigma_{\bar{y}}^2 = \frac{\sigma_{y_1}^2 + \sigma_{y_2}^2 + \ldots}{n^2} \quad (14)$$

$$\hat{c} = c + \frac{\sigma_{\bar{y}}^2}{n\sigma_{x+y}^2} \quad (15)$$

From equation 10 it is known that the second term in equation 15 can be expressed in terms of c.

$$\frac{\sigma_y^2}{\sigma_{x+y}^2} = 1 - c \quad 16$$

Making this substitution into equation 15, $$\hat{c} = c + \frac{1-c}{n} \qquad 17$$

And solving for c gives the final form of the bias correction.

$$c = \frac{n\hat{c} - 1}{n - 1} \qquad 18$$

When the assumptions of this model are met, this is the relationship that can be expected between the SFC estimated from n spikes, and the asymptotic coherence. Of course, in a practical application of this estimation method, there are inevitable deviations from the assumptions. This causes variability between the estimated and asymptotic coherence. However, results presented herein demonstrate that when coherence is estimated over multiple trials, the trial-averaged estimate satisfies this relationship well, indicating a reduction in bias.

Example 6

Single Neuron Synchrony with Local Field Oscillations

Figure 24A:
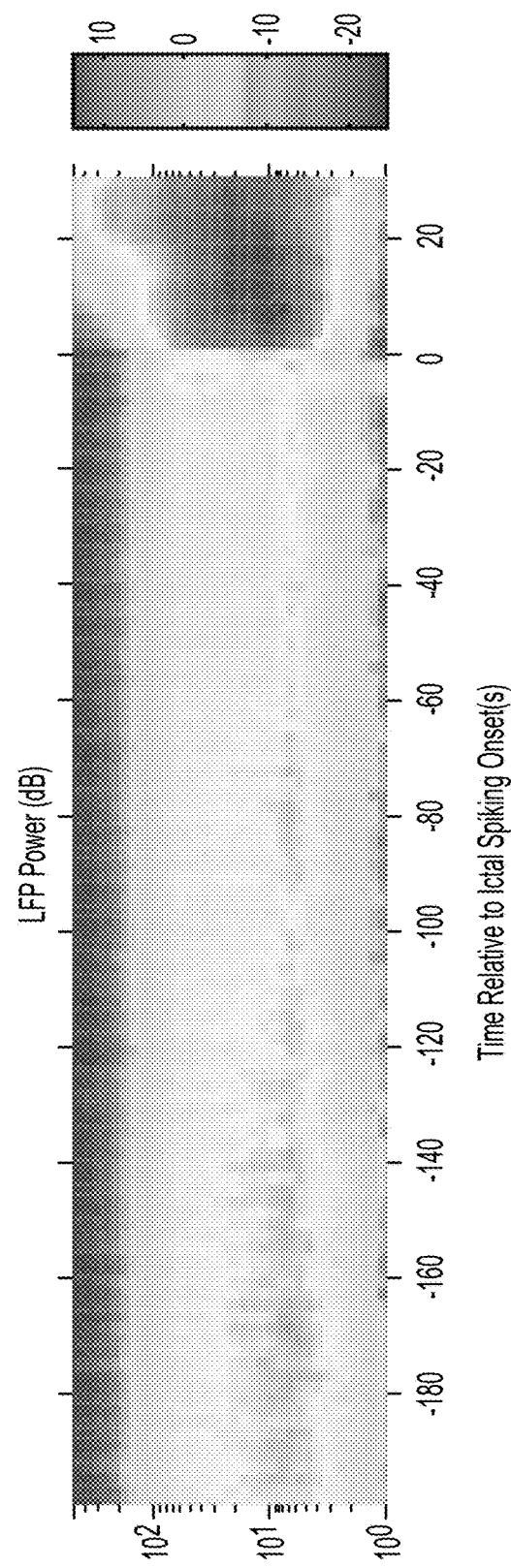
FIGS. 24A-24C, is a set of graphs illustrating average LFP power and SFC with respect to ictal spiking onset.
Figure 24B:
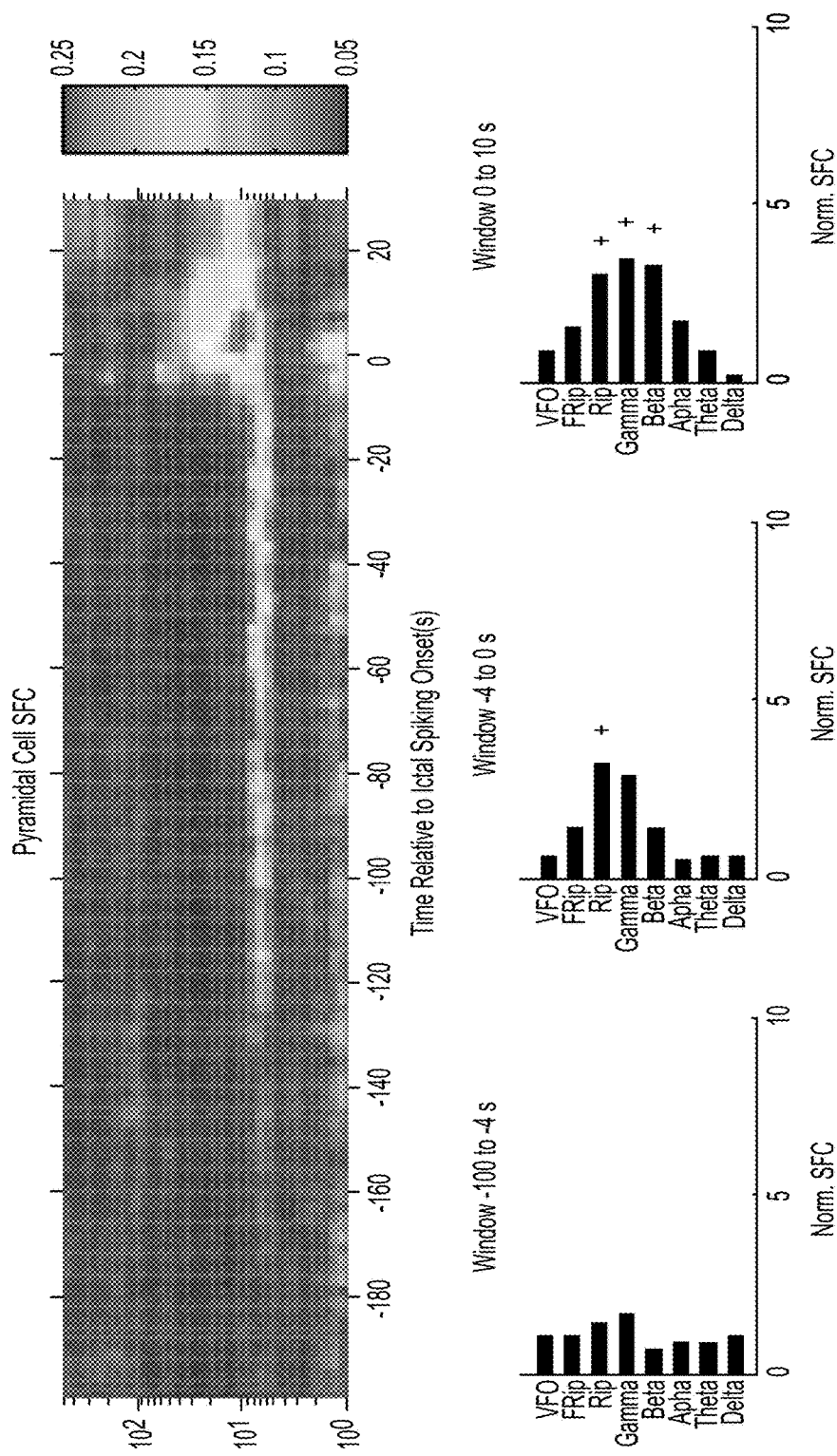
Figure 24C:
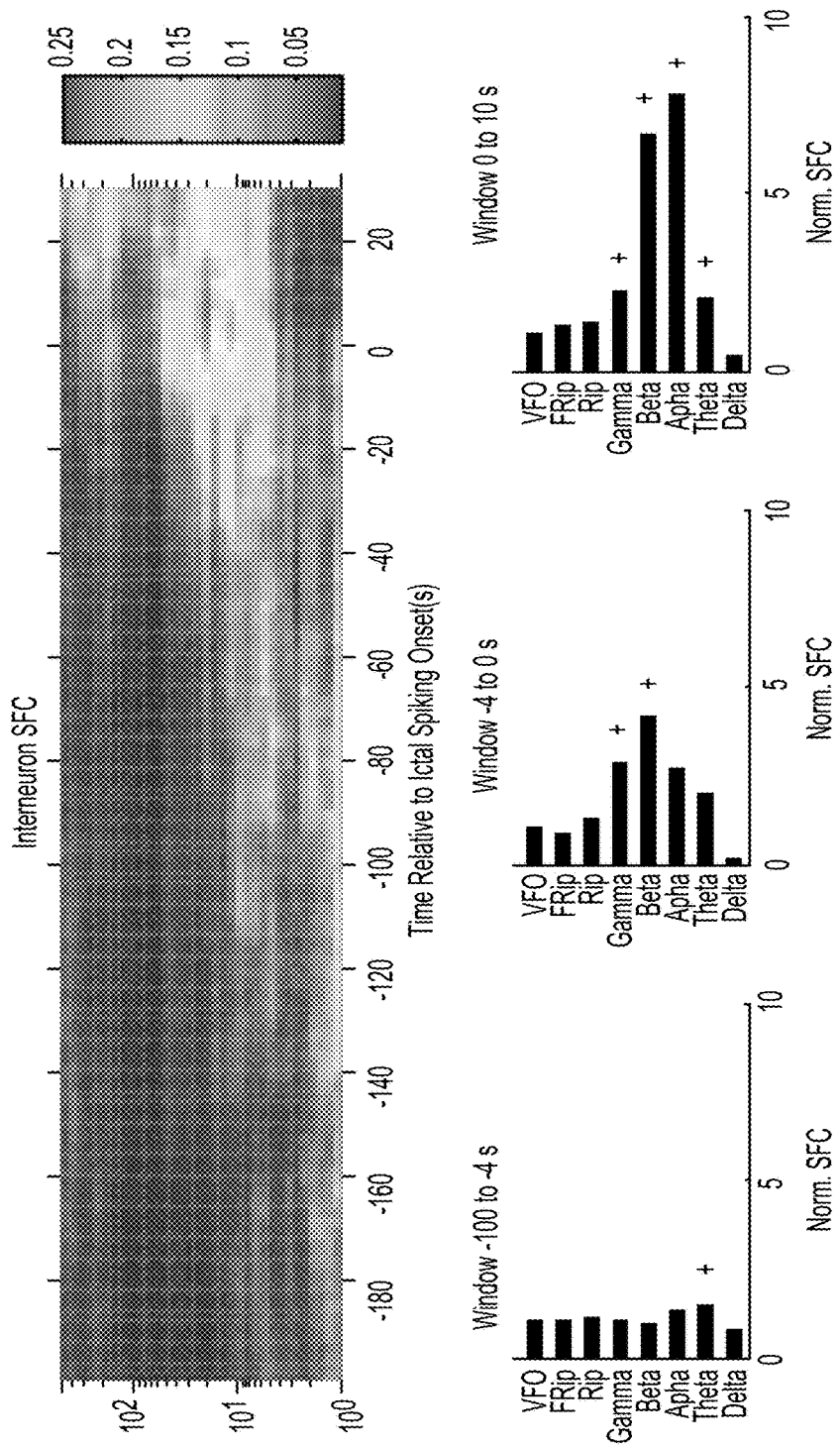

To fix the bias and variance of the estimate, the filter bank SFC was initially estimated for each neuron at a specified time by using a fixed number of action potentials (10 for pyramidal cells; 20 for interneurons) occurring around that time. In this way, a synchrony spectrogram was created for each neuron, aligned to the ictal spiking onset, and spectrograms were averaged by cell type, similar to the process of creating firing rate PETHs (FIG. 24).

This method was not sensitive to changes in SFC caused by a variable number of spikes, and was therefore useful for identifying real changes in SFC within an approximate time window. However, it is important to note that for a fixed number of spikes, the temporal resolution of this method is related to the firing rate of the neurons. For this reason, this method was not appropriate for statistical quantification of changes in precise time windows. Therefore, utilizing the bias correction, a second SFC method was employed after choosing appropriate frequency bands and time windows, based on the SFC spectrogram.

From these population-averaged SFC spectrograms, a number of trends were apparent in the time leading up to, and following the ictal spiking onset. Pyramidal cells and interneurons displayed a number of similar changes around seizure onset, with some subtle differences. Interneurons were coherent with theta oscillations in the period of −100 to −4 seconds before ictal spiking onset. Although this increase was significant from background, the magnitude of the increase was not especially high. In the 4 second period just before the ictal spiking onset, SFC was increased in an additional number of frequency bands. Pyramidal cells only significant coherence increase during this time was in the gamma band; although the ripple band was also well above the mean background level. Interneurons increased significantly in the beta and gamma bands, which was generally a lower frequency spectrum than pyramidal cell increases. Overall, the largest increases to SFC, especially for interneurons, came in the first 10 seconds after the ictal spiking onset. From the SFC spectrograms, it is clear that there was some overlap between pyramidal cells and interneurons in terms of the frequencies with increased coherence. The beta band in particular was one of the highest increased bands for both cell types. This is, incidentally, the band implicated in LVF activity in some in vitro models. We also see the same pattern of interneurons having a coherence spectrum of lower frequency than pyramidal cells. One last observation of note is that the period of highest rhythmic synchrony for both cell types (0 to 10 s) begins during the peak of interneuron activity, and ends during the peak of pyramidal cell activity.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

The invention claimed is:

1. A method for preventing a seizure in a subject, comprising:
   recording single interneuron activity for a plurality of interneurons;
   recording local field potential (LFP);
   measuring interneuron synchrony;
   detecting a specific pattern of interneuron activity and interneuron synchrony comprising:
      increased synchrony between interneuron action potentials and theta-wave LFP oscillations, followed by
      increased synchrony between interneuron action potentials and gamma-wave LFP oscillations;
   wherein detection of the specific pattern of interneuron activity and interneuron synchrony signifies an increased likelihood of a seizure;
   wherein detecting the specific pattern of interneuron activity and interneuron synchrony is performed by a system comprising an algorithm; and
   wherein the parameters of the algorithm are automatically generated without a human observer; and
   administering a therapeutically effective intervention to the subject to prevent the onset of a seizure in response to the detection of the specific pattern.

2. The method of claim 1, wherein detecting the specific pattern of interneuron activity and interneuron synchrony comprises detecting the correlation of interneuron-interneuron pairs.

3. The method of claim 1, wherein the specific pattern of interneuron activity and interneuron synchrony further comprises increased firing rate.

4. The method of claim 1, wherein the specific pattern further comprises increased coherence between interneuron action potentials and theta wave LFP oscillations occurring between 1 and 10 minutes prior to a predicted seizure.

5. The method of claim 1, wherein the specific pattern further comprises increased coherence between interneuron action potentials and gamma wave LFP oscillations occurring between 5 and 30 seconds prior to a predicted seizure.

6. The method of claim 1, further comprising recording single neuron activity for a plurality of excitatory neurons.

7. The method of claim 6, wherein the excitatory neurons are pyramidal cell neurons.

8. The method of claim 1, wherein the single neuron activity is measured in the hippocampus of the subject.

9. The method of claim 1, wherein the therapeutically effective intervention comprises an electrical stimulation.

10. The method of claim 1, wherein the therapeutically effective intervention comprises the delivery of a drug.

* * * * *